US011896202B2

(12) United States Patent
Beckman et al.

(10) Patent No.: US 11,896,202 B2
(45) Date of Patent: Feb. 13, 2024

(54) ARTICULATION MECHANISMS FOR ROBOTIC SURGICAL TOOLS

(71) Applicant: Cilag GmbH International, Zug (CH)

(72) Inventors: Andrew T. Beckman, Cincinnati, OH (US); Charles J. Scheib, Loveland, OH (US); Neil Markwardt, Redwood City, CA (US)

(73) Assignee: Cilag GmbH International, Zug (CH)

( * ) Notice: Subject to any disclaimer, the term of this patent is extended or adjusted under 35 U.S.C. 154(b) by 600 days.

(21) Appl. No.: 16/946,363

(22) Filed: Jun. 18, 2020

(65) Prior Publication Data

US 2021/0393340 A1 Dec. 23, 2021

(51) Int. Cl.
*A61B 1/00* (2006.01)
*A61B 34/30* (2016.01)
(Continued)

(52) U.S. Cl.
CPC ...... *A61B 1/00149* (2013.01); *A61B 1/00009* (2013.01); *A61B 17/00234* (2013.01); *A61B 17/072* (2013.01); *A61B 17/1285* (2013.01); *A61B 17/29* (2013.01); *A61B 17/3201* (2013.01); *A61B 18/1442* (2013.01); *A61B 34/20* (2016.02); *A61B 34/30* (2016.02); *A61B 90/50* (2016.02); *B25J 9/102* (2013.01); *B25J 15/0019* (2013.01); *B25J 17/0241* (2013.01); *F16H 1/20* (2013.01); *F16H 25/186* (2013.01); *F16H 25/20* (2013.01); *F16H 57/0025* (2013.01); *A61B 2018/0063* (2013.01); *A61B 2018/126* (2013.01); *A61B 2034/2051* (2016.02); *A61B 2034/301* (2016.02);
(Continued)

(58) Field of Classification Search
CPC .............. A61B 34/70; A61B 2034/301; A61B 2034/302; A61B 2034/303; A61B 2034/305; A61B 34/35
See application file for complete search history.

(56) References Cited

U.S. PATENT DOCUMENTS

| 5,807,378 A | 9/1998 | Jensen |
| 2018/0116738 A1 | 5/2018 | Bajo |

(Continued)

FOREIGN PATENT DOCUMENTS

WO    WO 2019/191396    * 10/2019

OTHER PUBLICATIONS

ISR-WO for related matter PCT/EP2021/066691 dated Dec. 9, 2021.

*Primary Examiner* — Thomas McEvoy
(74) *Attorney, Agent, or Firm* — Vorys, Sater, Seymour and Pease LLP

(57) ABSTRACT

A robotic surgical tool includes a drive housing having a first end and a second end, at least one spline extending between the first and second ends and including a drive gear that rotates with rotation of the spline, and a carriage movably mounted to the spline. An elongate shaft extends from the carriage and through the first end, an end effector is arranged at a distal end of the elongate shaft, and a wrist interposes the end effector and the distal end of the shaft. An activating mechanism is housed in the carriage and operatively coupled to the drive gear such that rotation of the drive gear correspondingly actuates the activating mechanism and thereby causes the wrist to articulate the end effector in at least one plane.

11 Claims, 39 Drawing Sheets

(51) Int. Cl.
*A61B 34/20* (2016.01)
*A61B 17/072* (2006.01)
*A61B 17/29* (2006.01)
*A61B 17/3201* (2006.01)
*A61B 17/128* (2006.01)
*A61B 18/14* (2006.01)
*A61B 17/00* (2006.01)
*F16H 57/00* (2012.01)
*F16H 1/20* (2006.01)
*F16H 25/20* (2006.01)
*F16H 25/18* (2006.01)
*B25J 15/00* (2006.01)
*B25J 17/02* (2006.01)
*B25J 9/10* (2006.01)
*A61B 90/50* (2016.01)
*A61B 18/00* (2006.01)
*A61B 18/12* (2006.01)

(52) U.S. Cl.
CPC ... *A61B 2034/302* (2016.02); *A61B 2217/005* (2013.01); *A61B 2217/007* (2013.01); *F16H 2025/2059* (2013.01); *F16H 2025/2081* (2013.01)

(56) References Cited

U.S. PATENT DOCUMENTS

2020/0093549 A1 3/2020 Chin
2021/0015572 A1 1/2021 Gomez et al.
2021/0022815 A1 1/2021 Abbott

* cited by examiner

ARTICULATION MECHANISMS FOR ROBOTIC SURGICAL TOOLS

TECHNICAL FIELD

The systems and methods disclosed herein are directed to robotic surgical tools and, more particularly to, robotic surgical tools including a carriage movably mounted to a lead screw and one or more splines actuatable to operate various functions of the robotic surgical tool.

BACKGROUND

Minimally invasive surgical (MIS) instruments are often preferred over traditional open surgical devices due to the reduced post-operative recovery time and minimal scarring. The most common MIS procedure may be endoscopy, and the most common form of endoscopy is laparoscopy, in which one or more small incisions are formed in the abdomen of a patient and a trocar is inserted through the incision to form a pathway that provides access to the abdominal cavity. The cannula and sealing system of the trocar are used to introduce various instruments and tools into the abdominal cavity, as well as to provide insufflation to elevate the abdominal wall above the organs. The instruments can be used to engage and/or treat tissue in a number of ways to achieve a diagnostic or therapeutic effect.

Each surgical tool typically includes an end effector arranged at its distal end. Example end effectors include clamps, graspers, scissors, staplers, suction irrigators, blades (i.e., RF), and needle holders, and are similar to those used in conventional (open) surgery except that the end effector of each tool is separated from its handle by an approximately 12-inch long shaft. A camera or image capture device, such as an endoscope, is also commonly introduced into the abdominal cavity to enable the surgeon to view the surgical field and the operation of the end effectors during operation. The surgeon is able to view the procedure in real-time by means of a visual display in communication with the image capture device.

Various robotic systems have recently been developed to assist in MIS procedures. Robotic systems can allow for more intuitive hand movements by maintaining natural eye-hand axis. Robotic systems can also allow for more degrees of freedom in movement by including a "wrist" joint that creates a more natural hand-like articulation and allows for access to hard to reach spaces. The instrument's end effector can be articulated (moved) using motors and actuators forming part of a computerized motion system. A user (e.g., a surgeon) is able to remotely operate an instrument's end effector by grasping and manipulating in space one or more controllers that communicate with an instrument driver coupled to the surgical instrument. User inputs are processed by a computer system incorporated into the robotic surgical system and the instrument driver responds by actuating the motors and actuators of the motion system. Moving the drive cables and/or other mechanical mechanisms manipulates the end effector to desired positions and configurations.

Improvements to robotically-enabled medical systems will provide physicians with the ability to perform endoscopic and laparoscopic procedures more effectively and with improved ease.

SUMMARY OF DISCLOSURE

Various details of the present disclosure are hereinafter summarized to provide a basic understanding. This summary is not an extensive overview of the disclosure and is neither intended to identify certain elements of the disclosure, nor to delineate the scope thereof. Rather, the primary purpose of this summary is to present some concepts of the disclosure in a simplified form prior to the more detailed description that is presented hereinafter.

Embodiments disclosed herein include a robotic surgical tool that includes a drive housing having a first end and a second end, at least one spline extending between the first and second ends and including a drive gear that rotates with rotation of the at least one spline, and a carriage movably mounted to the at least one spline. An elongate shaft extends from the carriage and through the first end, and an end effector is arranged at a distal end of the elongate shaft. A wrist interposes the end effector and the distal end of the shaft, and an activating mechanism is housed in the carriage and operatively coupled to the drive gear such that rotation of the drive gear correspondingly actuates the activating mechanism and thereby causes the wrist to articulate the end effector in at least one plane. In a further embodiment, the robotic surgical tool further includes a drive input arranged at the first end and operatively coupled to the at least one spline such that rotation of the drive input correspondingly rotates the at least one spline and the drive gear, and wherein the robotic surgical tool is capable of engaging an instrument driver arranged at an end of a robotic arm and matable with the drive housing at the first end, the instrument driver providing a drive output matable with the drive input such that rotation of the drive output correspondingly rotates the drive input and thereby actuates the activating mechanism. In another further embodiment, the shaft extends through the instrument driver via a central aperture defined longitudinally through the instrument driver. In another further embodiment, the carriage comprises at least a first layer and a second layer arranged in series, and wherein the drive gear is arranged between portions of the first and second layers and slidably disposed about the at least one second spline. In another further embodiment, the activating mechanism comprises a first carrier extending at least partially about the shaft and operatively coupled to a first drive member that extends to the wrist, and a second carrier extending at least partially about the shaft and operatively coupled to a second drive member that extends to the wrist, wherein actuation of the activating mechanism causes the first carrier and the first drive member to move along the shaft in a first axial direction and further causes the second carrier and the second drive member to move along the shaft in a second axial direction, wherein the first and second axial directions are equal and opposite. In another further embodiment, distal ends of the first and second drive members antagonistically operate at the end effector to articulate the end effector in the at least one plane. In another further embodiment, the activating mechanism further comprises a first transfer gear extending about the shaft and defining internal threads, the first carrier radially interposing the shaft and the first transfer gear and defining external threads matable with the internal threads of the first transfer gear, and a second transfer gear extending about the shaft and defining internal threads, the second carrier radially interposing the shaft and the second transfer gear and defining external threads matable with the internal threads of the second transfer gear, wherein the first and second transfer gears are matable with the drive gear such that rotation of the drive gear simultaneously rotates the first and second transfer gears, and wherein the internal threads of the first and second transfer gears are threaded in opposite directions such that rotating the first and second transfer gears causes the first and second carriers to move in equal but opposite axial directions along the shaft. In another further embodiment, a gap is provided between the first and second carriers to allow the first and second carriers to move toward and away from each other during actuation of the activating mechanism. In another further embodiment, the activating mechanism further comprises an articulation barrel rotatably disposed about the shaft, the driven gear being provided on the articulation barrel and the first and second carriers radially interposing the shaft and the articulation barrel, first and second cam profiles defined in the articulation barrel and extending about a circumference of the articulation barrel at equal but opposite angles, a first follower pin extending through the first cam profile and coupled to the first carrier, and a second follower pin extending through the second cam profile and coupled to the second carrier, wherein as the articulation barrel is rotated by the drive gear, the first and second follower pins are urged to traverse the first and second cam profiles, respectively, and thereby urge the first and second carriers in equal but opposite axial directions. In another further embodiment, the activating mechanism further comprises a first articulation torque bar secured to the carriage and defining a first slot that receives a head of the first follower pin, and a second articulation torque bar secured to the carriage and defining a second slot that receives a head of the second follower pin. In another further embodiment, each follower pin includes a first bearing that bears against an inner wall of the first or second cam profile as the articulation barrel rotates, and a second bearing capable of bearing against an inner wall of the first or second slot as the articulation barrel rotates. In another further embodiment, at least one of the first and second cam profiles provides an inflection point along a path of the first and second cam profiles. In another further embodiment, the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

Embodiments disclosed herein may further include a method that includes locating a robotic surgical tool adjacent a patient, the robotic surgical tool comprising a drive housing having a first end and a second end, at least one spline extending between the first and second ends and including a drive gear that rotates with rotation of the at least one spline, a carriage movably mounted to the at least one spline, an elongate shaft extending from the carriage and penetrating the first end, an end effector arranged at a distal end of the elongate shaft, a wrist that interposes the end effector and the distal end of the shaft, and an activating mechanism housed in the carriage and operatively coupled to the drive gear. The method may further include rotating the at least one spline and the drive gear by actuating a drive input arranged at the first end and operatively coupled to the at least one spline, and actuating the activating mechanism as the drive gear rotates and thereby articulating the end effector in at least one plane at the wrist. In a further embodiment, the method also includes mating an instrument driver with the drive housing at the first end, the instrument driver being arranged at an end of a robotic arm, mating a drive output of the instrument driver with the drive input as the instrument driver is mated to the drive housing, and actuating the drive output to rotate the drive input and thereby actuate the activating mechanism. In a further embodiment, mating the instrument driver with the drive housing at the first end comprises extending the shaft, the end effector, and the wrist through a central aperture defined longitudinally through the instrument driver. In a further embodiment, the activating mechanism includes a first carrier extending at least partially about the shaft and operatively coupled to a first drive member that extends to the wrist, and a second carrier extending at least partially about the shaft and operatively coupled to a second drive member that extends to the wrist, and wherein actuating the activating comprises causing the first carrier and the first drive member to move along the shaft in a first axial direction, and causing the second carrier and the second drive member to move along the shaft in a second axial direction, where the first and second axial directions are equal and opposite. In a further embodiment, the method also includes antagonistically operating distal ends of the first and second drive members at the end effector and thereby articulating the end effector in the at least one plane. In a further embodiment, the activating mechanism further includes a first transfer gear extending about the shaft and defining internal threads, the first carrier radially interposing the shaft and the first transfer gear and defining external threads matable with the internal threads of the first transfer gear, and a second transfer gear extending about the shaft and defining internal threads, the second carrier radially interposing the shaft and the second transfer gear and defining external threads matable with the internal threads of the second transfer gear, the method further comprising mating the drive gear with the first and second transfer gears, rotating the drive gear and thereby simultaneously rotating the first and second transfer gears, wherein the internal threads of the first and second transfer gears are threaded in opposite directions, and causing the first and second carriers to move in equal but opposite axial directions along the shaft as the first and second transfer gears rotate. In a further embodiment, the activating mechanism further includes, an articulation barrel rotatably disposed about the shaft, the driven gear being provided on the articulation barrel and the first and second carriers radially interposing the shaft and the articulation barrel, first and second cam profiles defined in the articulation barrel and extending about a circumference of the articulation barrel at equal but opposite angles, a first follower pin extending through the first cam profile and coupled to the first carrier, and a second follower pin extending through the second cam profile and coupled to the second carrier, the method further comprising rotating the articulation barrel with the drive gear, urging the first and second follower pins to traverse the first and second cam profiles, respectively, as the articulation barrel rotates, and urging the first and second carriers to move in equal but opposite axial directions along the shaft as the first and second follower pins traverse the first and second cam profiles.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive (e.g., laparoscopy) and non-invasive (e.g., endoscopy) procedures. Among endoscopy procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
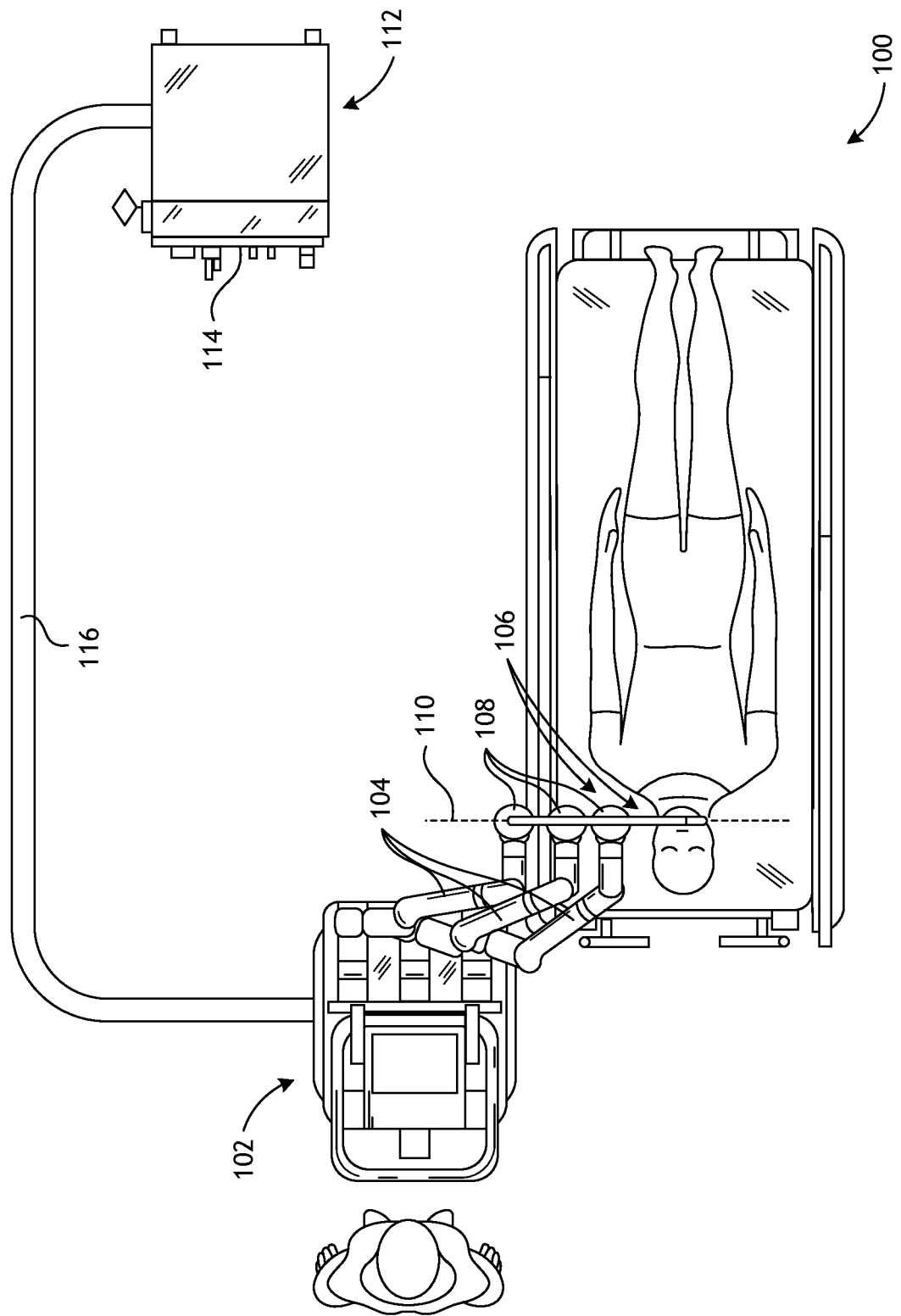
FIG. 1 illustrates an embodiment of a cart-based robotic system arranged for diagnostic and/or therapeutic bronchoscopy procedure(s).

The robotically-enabled medical system may be configured in a variety of ways depending on the particular procedure. FIG. 1 illustrates an embodiment of a cart-based robotically-enabled system 100 arranged for a diagnostic and/or therapeutic bronchoscopy procedure. For a bronchoscopy procedure, the robotic system 100 may include a cart 102 having one or more robotic arms 104 (three shown) to deliver a medical instrument (alternately referred to as a "surgical tool"), such as a steerable endoscope 106 (e.g., a procedure-specific bronchoscope for bronchoscopy), to a natural orifice access point (i.e., the mouth of the patient) to deliver diagnostic and/or therapeutic tools. As shown, the cart 102 may be positioned proximate to the patient's upper torso in order to provide access to the access point. Similarly, the robotic arms 104 may be actuated to position the bronchoscope relative to the access point. The arrangement in FIG. 1 may also be utilized when performing a gastro-intestinal (GI) procedure with a gastroscope, a specialized endoscope for GI procedures.

Once the cart 102 is properly positioned adjacent the patient, the robotic arms 104 are operated to insert the steerable endoscope 106 into the patient robotically, manually, or a combination thereof. The steerable endoscope 106 may comprise at least two telescoping parts, such as an inner leader portion and an outer sheath portion, where each portion is coupled to a separate instrument driver of a set of instrument drivers 108. As illustrated, each instrument driver 108 is coupled to the distal end of a corresponding one of the robotic arms 104. This linear arrangement of the instrument drivers 108, which facilitates coaxially aligning the leader portion with the sheath portion, creates a "virtual rail" 110 that may be repositioned in space by manipulating the robotic arms 104 into different angles and/or positions. Translation of the instrument drivers 108 along the virtual rail 110 telescopes the inner leader portion relative to the outer sheath portion, thus effectively advancing or retracting the endoscope 106 relative to the patient.

As illustrated, the virtual rail 110 (and other virtual rails described herein) is depicted in the drawings using dashed lines, thus not constituting any physical structure of the system 100. The angle of the virtual rail 110 may be adjusted, translated, and pivoted based on clinical application or physician preference. For example, in bronchoscopy, the angle and position of the virtual rail 110 as shown represents a compromise between providing physician access to the endoscope 106 while minimizing friction that results from bending the endoscope 106 into the patient's mouth.

After insertion into the patient's mouth, the endoscope 106 may be directed down the patient's trachea and lungs using precise commands from the robotic system 100 until reaching a target destination or operative site. In order to enhance navigation through the patient's lung network and/or reach the desired target, the endoscope 106 may be manipulated to telescopically extend the inner leader portion from the outer sheath portion to obtain enhanced articulation and greater bend radius. The use of separate instrument drivers 108 also allows the leader portion and sheath portion to be driven independent of each other.

For example, the endoscope 106 may be directed to deliver a biopsy needle to a target, such as, for example, a lesion or nodule within the lungs of a patient. The needle may be deployed down a working channel that runs the length of the endoscope 106 to obtain a tissue sample to be analyzed by a pathologist. Depending on the pathology results, additional tools may be deployed down the working channel of the endoscope for additional biopsies. After identifying a tissue sample to be malignant, the endoscope 106 may endoscopically deliver tools to resect the potentially cancerous tissue. In some instances, diagnostic and therapeutic treatments can be delivered in separate procedures. In those circumstances, the endoscope 106 may also be used to deliver a fiducial marker to "mark" the location of a target nodule as well. In other instances, diagnostic and therapeutic treatments may be delivered during the same procedure.

The system 100 may also include a movable tower 112, which may be connected via support cables to the cart 102 to provide support for controls, electronics, fluidics, optics, sensors, and/or power to the cart 102. Placing such functionality in the tower 112 allows for a smaller form factor cart 102 that may be more easily adjusted and/or re-positioned by an operating physician and his/her staff. Additionally, the division of functionality between the cart/table and the support tower 112 reduces operating room clutter and facilitates improving clinical workflow. While the cart 102 may be positioned close to the patient, the tower 112 may alternatively be stowed in a remote location to stay out of the way during a procedure.

In support of the robotic systems described above, the tower 112 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 112 or the cart 102, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, motors in the joints of the robotic arms 104 may position the arms into a certain posture or angular orientation.

The tower 112 may also include one or more of a pump, flow meter, valve control, and/or fluid access in order to provide controlled irrigation and aspiration capabilities to the system 100 that may be deployed through the endoscope 106. These components may also be controlled using the computer system of the tower 112. In some embodiments, irrigation and aspiration capabilities may be delivered directly to the endoscope 106 through separate cable(s).

The tower 112 may include a voltage and surge protector designed to provide filtered and protected electrical power to the cart 102, thereby avoiding placement of a power transformer and other auxiliary power components in the cart 102, resulting in a smaller, more moveable cart 102.

The tower 112 may also include support equipment for sensors deployed throughout the robotic system 100. For example, the tower 112 may include opto-electronics equipment for detecting, receiving, and processing data received from optical sensors or cameras throughout the robotic system 100. In combination with the control system, such opto-electronics equipment may be used to generate real-time images for display in any number of consoles deployed throughout the system, including in the tower 112. Similarly, the tower 112 may also include an electronic subsystem for receiving and processing signals received from deployed electromagnetic (EM) sensors. The tower 112 may also be used to house and position an EM field generator for detection by EM sensors in or on the medical instrument.

The tower 112 may also include a console 114 in addition to other consoles available in the rest of the system, e.g., a console mounted to the cart 102. The console 114 may include a user interface and a display screen (e.g., a touchscreen) for the physician operator. Consoles in the system 100 are generally designed to provide both robotic controls as well as pre-operative and real-time information of the procedure, such as navigational and localization information of the endoscope 106. When the console 114 is not the only console available to the physician, it may be used by a second operator, such as a nurse, to monitor the health or vitals of the patient and the operation of system, as well as provide procedure-specific data, such as navigational and localization information. In other embodiments, the console 114 may be housed in a body separate from the tower 112.

The tower 112 may be coupled to the cart 102 and endoscope 106 through one or more cables 116 connections. In some embodiments, support functionality from the tower 112 may be provided through a single cable 116 extending to the cart 102, thus simplifying and de-cluttering the operating room. In other embodiments, specific functionality may be coupled in separate cabling and connections. For example, while power may be provided through a single power cable to the cart 102, support for controls, optics, fluidics, and/or navigation may be provided through one or more separate cables.

Figure 2:
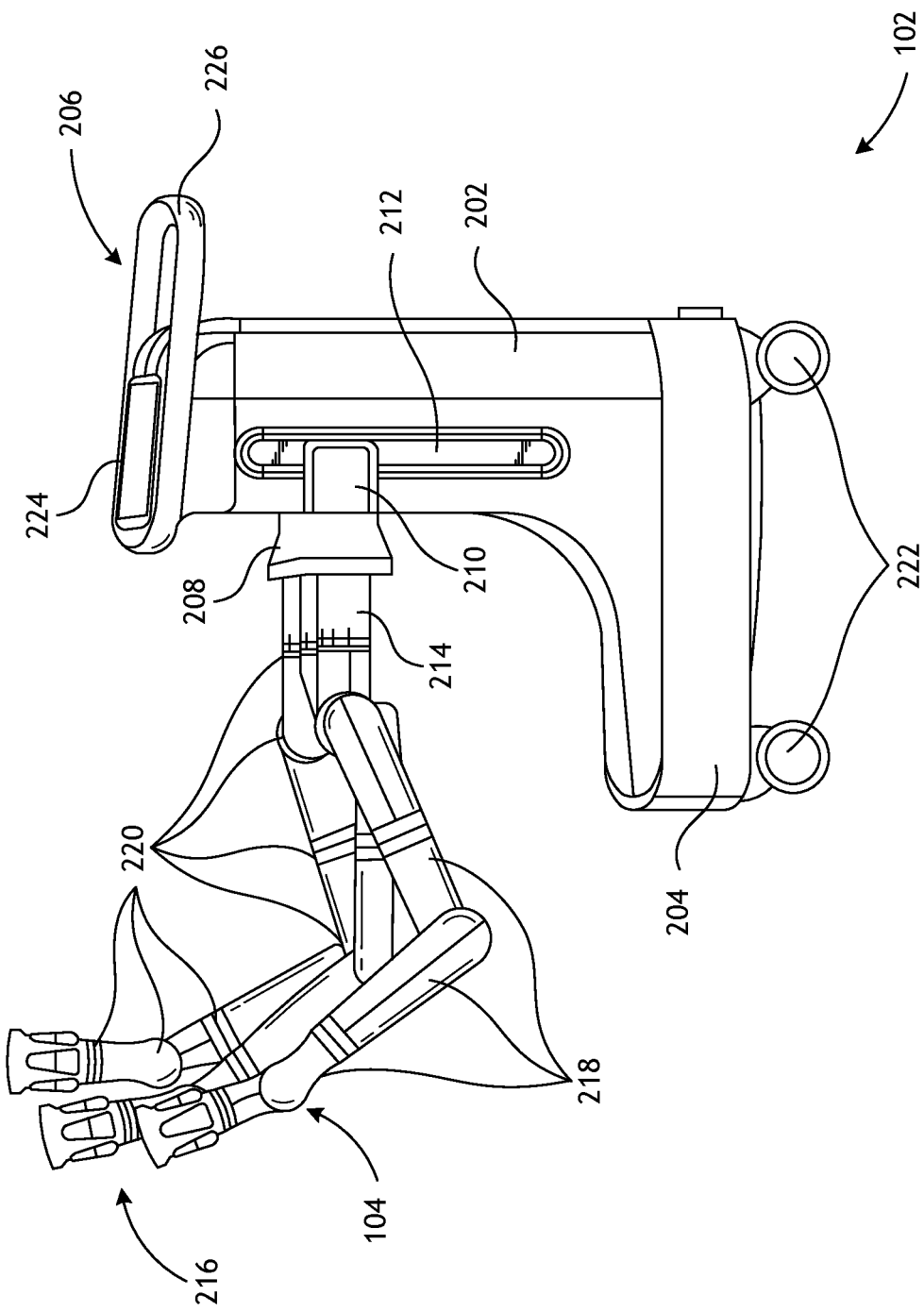
FIG. 2 depicts further aspects of the robotic system of FIG. 1.

FIG. 2 provides a detailed illustration of an embodiment of the cart 102 from the cart-based robotically-enabled system 100 of FIG. 1. The cart 102 generally includes an elongated support structure 202 (also referred to as a "column"), a cart base 204, and a console 206 at the top of the column 202. The column 202 may include one or more carriages, such as a carriage 208 (alternatively "arm support") for supporting the deployment of the robotic arms 104. The carriage 208 may include individually configurable arm mounts that rotate along a perpendicular axis to adjust the base 214 of the robotic arms 104 for better positioning relative to the patient. The carriage 208 also includes a carriage interface 210 that allows the carriage 208 to vertically translate along the column 202.

The carriage interface 210 is connected to the column 202 through slots, such as slot 212, that are positioned on opposite sides of the column 202 to guide the vertical translation of the carriage 208. The slot 212 contains a vertical translation interface to position and hold the carriage 208 at various vertical heights relative to the cart base 204. Vertical translation of the carriage 208 allows the cart 102 to adjust the reach of the robotic arms 104 to meet a variety of table heights, patient sizes, and physician preferences. Similarly, the individually configurable arm mounts on the carriage 208 allow a base 214 of the robotic arms 104 to be angled in a variety of configurations.

In some embodiments, the slot 212 may be supplemented with slot covers (not shown) that are flush and parallel to the slot surface to prevent dirt and fluid ingress into the internal chambers of the column 202 and the vertical translation interface as the carriage 208 vertically translates. The slot covers may be deployed through pairs of spring spools positioned near the vertical top and bottom of the slot 212. The covers are coiled within the spools until deployed to extend and retract from their coiled state as the carriage 208 vertically translates up and down. The spring-loading of the spools provides force to retract the cover into a spool when carriage 208 translates towards the spool, while also maintaining a tight seal when the carriage 208 translates away from the spool. The covers may be connected to the carriage 208 using, for example, brackets in the carriage interface 210 to ensure proper extension and retraction of the cover as the carriage 208 translates.

The column 202 may internally comprise mechanisms, such as gears and motors, that are designed to use a vertically aligned lead screw to translate the carriage 208 in a mechanized fashion in response to control signals generated in response to user inputs, e.g., inputs from the console 206.

The robotic arms 104 may generally comprise robotic arm bases 214 and end effectors 216 (three shown), separated by a series of linkages 218 connected by a corresponding series of joints 220, each joint 220 including an independent actuator, and each actuator including an independently controllable motor. Each independently controllable joint 220 represents an independent degree of freedom available to the corresponding robotic arm 104. In the illustrated embodiment, each arm 104 has seven joints 220, thus providing seven degrees of freedom. A multitude of joints 220 result in a multitude of degrees of freedom, allowing for "redundant" degrees of freedom. Redundant degrees of freedom allow the robotic arms 104 to position their respective end effectors 216 at a specific position, orientation, and trajectory in space using different linkage positions and joint angles. This allows for the system 100 to position and direct a medical instrument from a desired point in space while allowing the physician to move the arm joints 220 into a clinically advantageous position away from the patient to create greater access, while avoiding arm collisions.

The cart base 204 balances the weight of the column 202, carriage 208, and arms 104 over the floor. Accordingly, the cart base 204 houses heavier components, such as electronics, motors, power supply, as well as components that either enable movement and/or immobilize the cart. For example, the cart base 204 includes rolling casters 222 that allow for the cart to easily move around the room prior to a procedure.

After reaching an appropriate position, the casters 222 may be immobilized using wheel locks to hold the cart 102 in place during the procedure.

Positioned at the vertical end of the column 202, the console 206 allows for both a user interface for receiving user input and a display screen (or a dual-purpose device such as, for example, a touchscreen 224) to provide the physician user with both pre-operative and intra-operative data. Potential pre-operative data on the touchscreen 224 may include pre-operative plans, navigation and mapping data derived from pre-operative computerized tomography (CT) scans, and/or notes from pre-operative patient interviews. Intra-operative data on the touchscreen 224 may include optical information provided from the tool, sensor and coordinate information from sensors, as well as vital patient statistics, such as respiration, heart rate, and/or pulse. The console 206 may be positioned and tilted to allow a physician to access the console from the side of the column 202 opposite carriage 208. From this position, the physician may view the console 206, the robotic arms 104, and the patient while operating the console 206 from behind the cart 102. As shown, the console 206 also includes a handle 226 to assist with maneuvering and stabilizing cart 102.

Figure 3A:
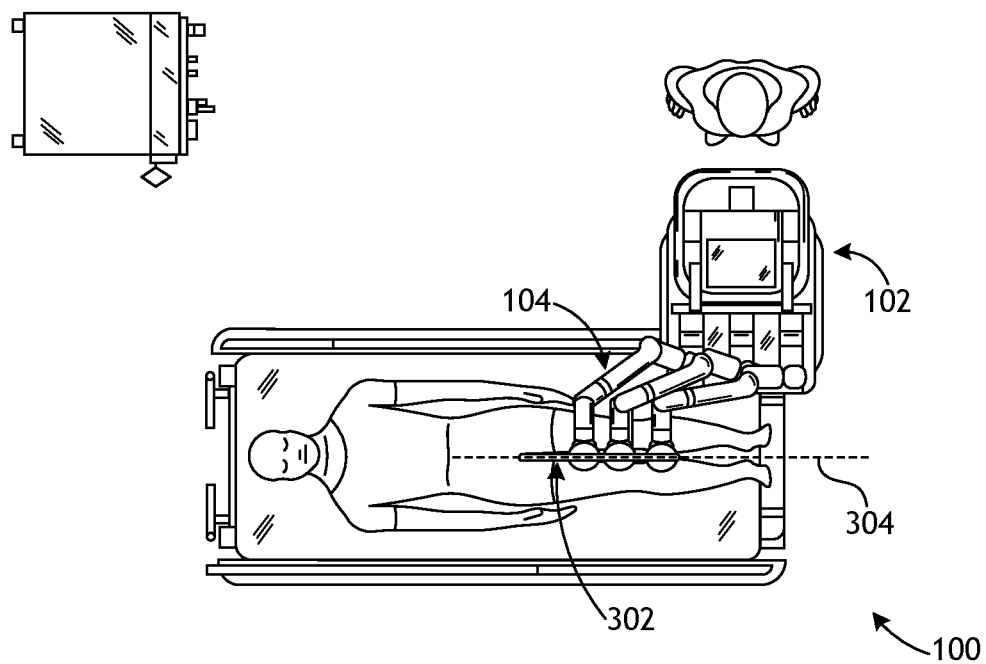
FIG. 3A illustrates an embodiment of the robotic system of FIG. 1 arranged for ureteroscopy.

FIG. 3A illustrates an embodiment of the system 100 of FIG. 1 arranged for ureteroscopy. In a ureteroscopic procedure, the cart 102 may be positioned to deliver a ureteroscope 302, a procedure-specific endoscope designed to traverse a patient's urethra and ureter, to the lower abdominal area of the patient. In ureteroscopy, it may be desirable for the ureteroscope 302 to be directly aligned with the patient's urethra to reduce friction and forces on the sensitive anatomy. As shown, the cart 102 may be aligned at the foot of the table to allow the robotic arms 104 to position the ureteroscope 302 for direct linear access to the patient's urethra. From the foot of the table, the robotic arms 104 may insert the ureteroscope 302 along a virtual rail 304 directly into the patient's lower abdomen through the urethra.

After insertion into the urethra, using similar control techniques as in bronchoscopy, the ureteroscope 302 may be navigated into the bladder, ureters, and/or kidneys for diagnostic and/or therapeutic applications. For example, the ureteroscope 302 may be directed into the ureter and kidneys to break up kidney stone build-up using a laser or ultrasonic lithotripsy device deployed down a working channel of the ureteroscope 302. After lithotripsy is complete, the resulting stone fragments may be removed using baskets deployed down the working channel of the ureteroscope 302.

Figure 3B:
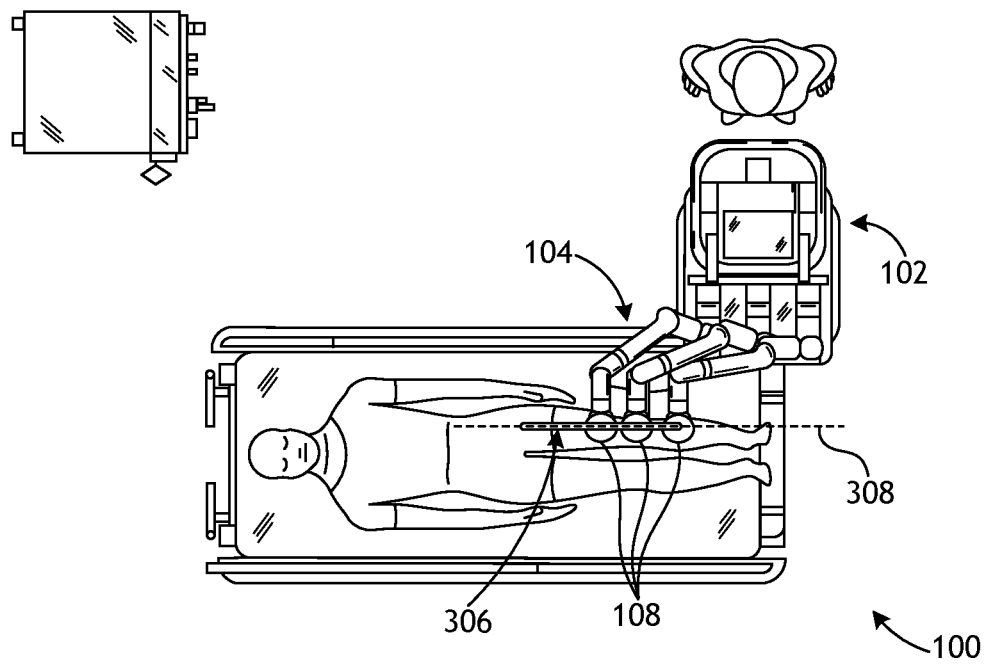
FIG. 3B illustrates an embodiment of the robotic system of FIG. 1 arranged for a vascular procedure.

FIG. 3B illustrates another embodiment of the system 100 of FIG. 1 arranged for a vascular procedure. In a vascular procedure, the system 100 may be configured such that the cart 102 may deliver a medical instrument 306, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 102 may be positioned towards the patient's legs and lower abdomen to allow the robotic arms 104 to provide a virtual rail 308 with direct linear access to the femoral artery access point in the patient's thigh/hip region. After insertion into the artery, the medical instrument 306 may be directed and advanced by translating the instrument drivers 108. Alternatively, the cart 102 may be positioned around the patient's upper abdomen in order to reach alternative vascular access points, such as, for example, the carotid and brachial arteries near the patient's shoulder and wrist.

B. Robotic System—Table.

Figure 4:
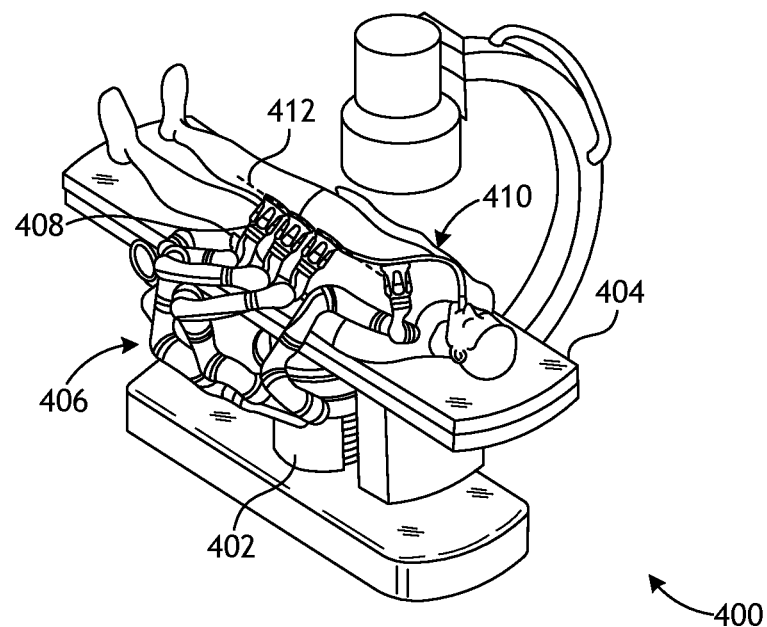
FIG. 4 illustrates an embodiment of a table-based robotic system arranged for a bronchoscopy procedure.

Embodiments of the robotically-enabled medical system may also incorporate the patient's table. Incorporation of the table reduces the amount of capital equipment within the operating room by removing the cart, which allows greater access to the patient. FIG. 4 illustrates an embodiment of such a robotically-enabled system 400 arranged for a bronchoscopy procedure. As illustrated, the system 400 includes a support structure or column 402 for supporting platform 404 (shown as a "table" or "bed") over the floor. Much like in the cart-based systems, the end effectors of the robotic arms 406 of the system 400 comprise instrument drivers 408 that are designed to manipulate an elongated medical instrument, such as a bronchoscope 410, through or along a virtual rail 412 formed from the linear alignment of the instrument drivers 408. In practice, a C-arm for providing fluoroscopic imaging may be positioned over the patient's upper abdominal area by placing the emitter and detector around the table 404.

Figure 5:
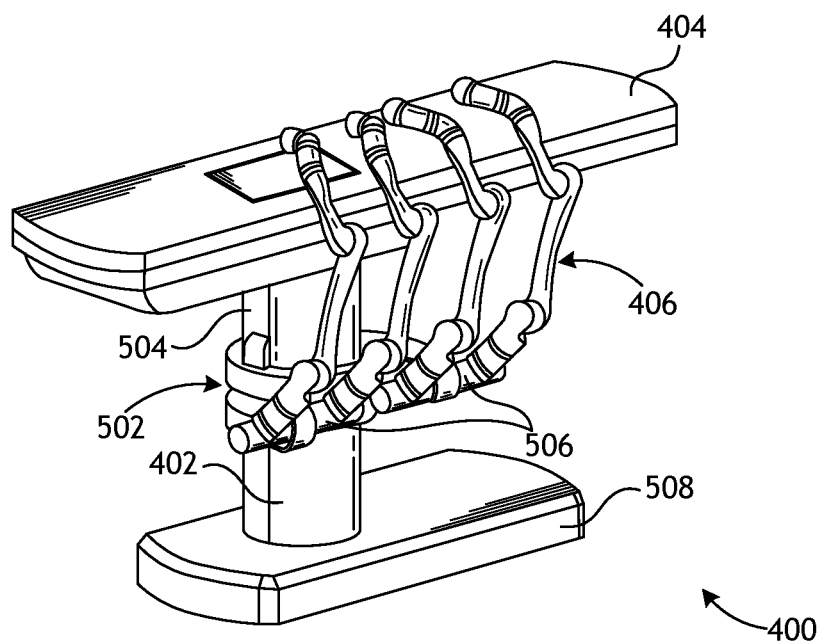
FIG. 5 provides an alternative view of the robotic system of FIG. 4.

FIG. 5 provides an alternative view of the system 400 without the patient and medical instrument for discussion purposes. As shown, the column 402 may include one or more carriages 502 shown as ring-shaped in the system 400, from which the one or more robotic arms 406 may be based. The carriages 502 may translate along a vertical column interface 504 that runs the length (height) of the column 402 to provide different vantage points from which the robotic arms 406 may be positioned to reach the patient. The carriage(s) 502 may rotate around the column 402 using a mechanical motor positioned within the column 402 to allow the robotic arms 406 to have access to multiples sides of the table 404, such as, for example, both sides of the patient. In embodiments with multiple carriages 502, the carriages 502 may be individually positioned on the column 402 and may translate and/or rotate independent of the other carriages 502. While carriages 502 need not surround the column 402 or even be circular, the ring-shape as shown facilitates rotation of the carriages 502 around the column 402 while maintaining structural balance. Rotation and translation of the carriages 502 allows the system 400 to align medical instruments, such as endoscopes and laparoscopes, into different access points on the patient.

In other embodiments (discussed in greater detail below with respect to FIG. 9A), the system 400 can include a patient table or bed with adjustable arm supports in the form of bars or rails extending alongside it. One or more robotic arms 406 (e.g., via a shoulder with an elbow joint) can be attached to the adjustable arm supports, which can be vertically adjusted. By providing vertical adjustment, the robotic arms 406 are advantageously capable of being stowed compactly beneath the patient table or bed, and subsequently raised during a procedure.

The arms 406 may be mounted on the carriages 502 through a set of arm mounts 506 comprising a series of joints that may individually rotate and/or telescopically extend to provide additional configurability to the robotic arms 406. Additionally, the arm mounts 506 may be positioned on the carriages 502 such that when the carriages 502 are appropriately rotated, the arm mounts 506 may be positioned on either the same side of the table 404 (as shown in FIG. 5), on opposite sides of table 404 (as shown in FIG. 7B), or on adjacent sides of the table 404 (not shown).

The column 402 structurally provides support for the table 404, and a path for vertical translation of the carriages 502. Internally, the column 402 may be equipped with lead screws for guiding vertical translation of the carriages, and motors to mechanize the translation of said carriages based the lead screws. The column 402 may also convey power and control signals to the carriage 502 and robotic arms 406 mounted thereon.

A table base 508 serves a similar function as the cart base 204 of the cart 102 shown in FIG. 2, housing heavier components to balance the table/bed 404, the column 402, the carriages 502, and the robotic arms 406. The table base 508 may also incorporate rigid casters to provide stability during procedures. Deployed from the bottom of the table base 508, the casters may extend in opposite directions on both sides of the base 508 and retract when the system 400 needs to be moved.

In some embodiments, the system 400 may also include a tower (not shown) that divides the functionality of system 400 between table and tower to reduce the form factor and bulk of the table 404. As in earlier disclosed embodiments, the tower may provide a variety of support functionalities to the table 404, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 508 for potential stowage of the robotic arms 406. The tower may also include a master controller or console that provides both a user interface for user input, such as keyboard and/or pendant, as well as a display screen (or touchscreen) for pre-operative and intra-operative information, such as real-time imaging, navigation, and tracking information. In some embodiments, the tower may also contain holders for gas tanks to be used for insufflation.

Figure 6:
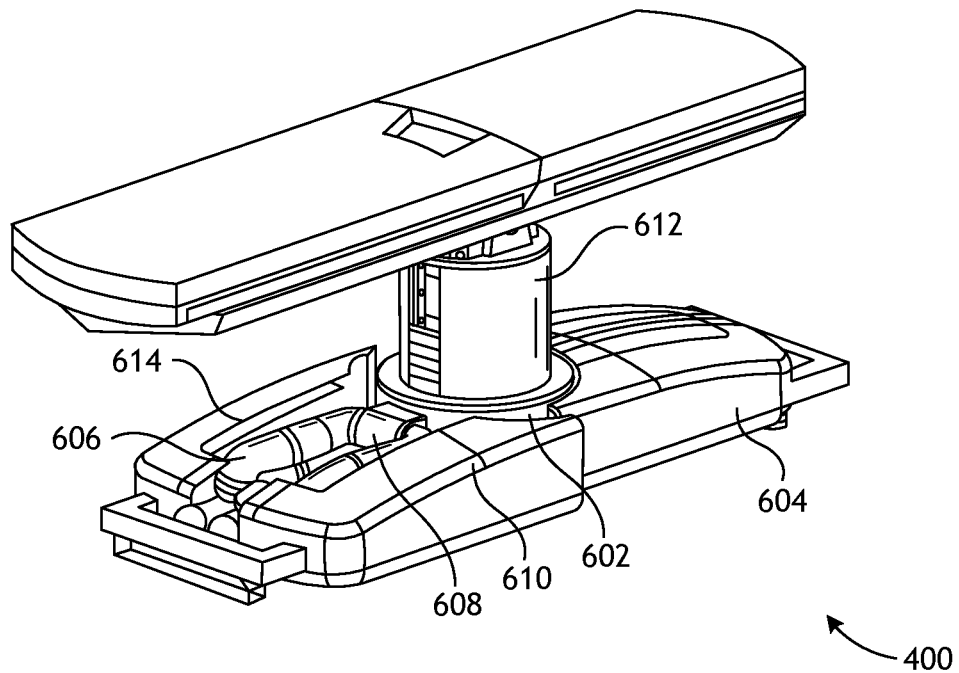
FIG. 6 illustrates an example system configured to stow robotic arm(s).

In some embodiments, a table base may stow and store the robotic arms when not in use. FIG. 6 illustrates an embodiment of the system 400 that is configured to stow robotic arms in an embodiment of the table-based system. In the system 400, one or more carriages 602 (one shown) may be vertically translated into a base 604 to stow one or more robotic arms 606, one or more arm mounts 608, and the carriages 602 within the base 604. Base covers 610 may be translated and retracted open to deploy the carriages 602, the arm mounts 608, and the arms 606 around the column 612, and closed to stow and protect them when not in use. The base covers 610 may be sealed with a membrane 614 along the edges of its opening to prevent dirt and fluid ingress when closed.

Figure 7A:
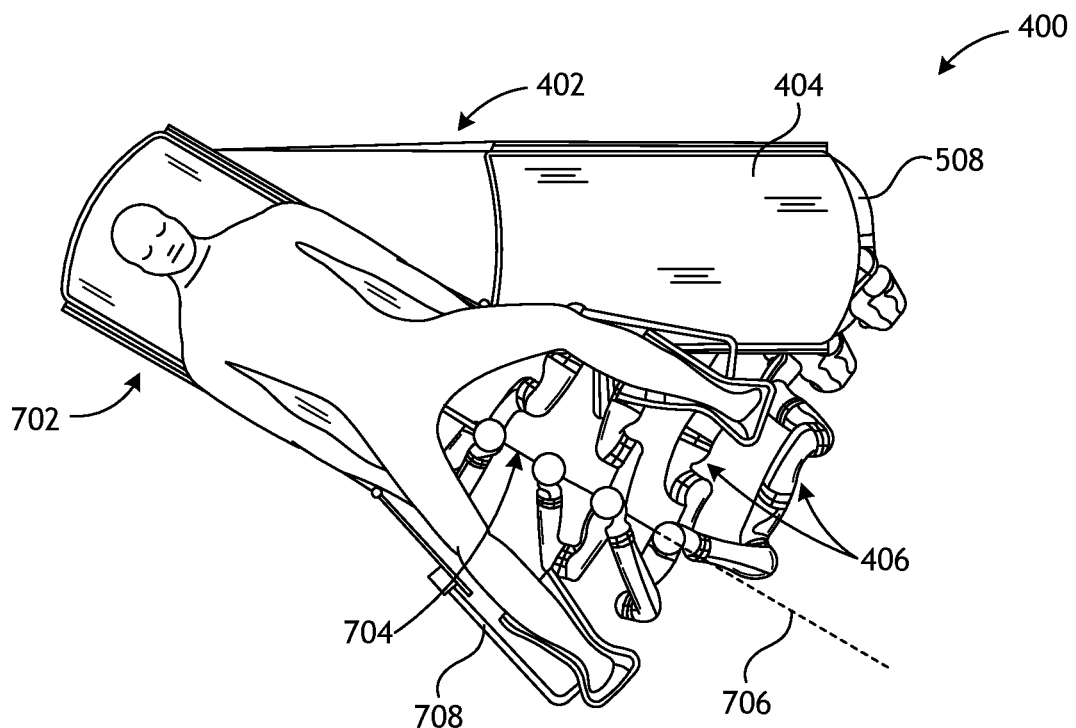
FIG. 7A illustrates an embodiment of a table-based robotic system configured for a ureteroscopy procedure.
Figure 7B:
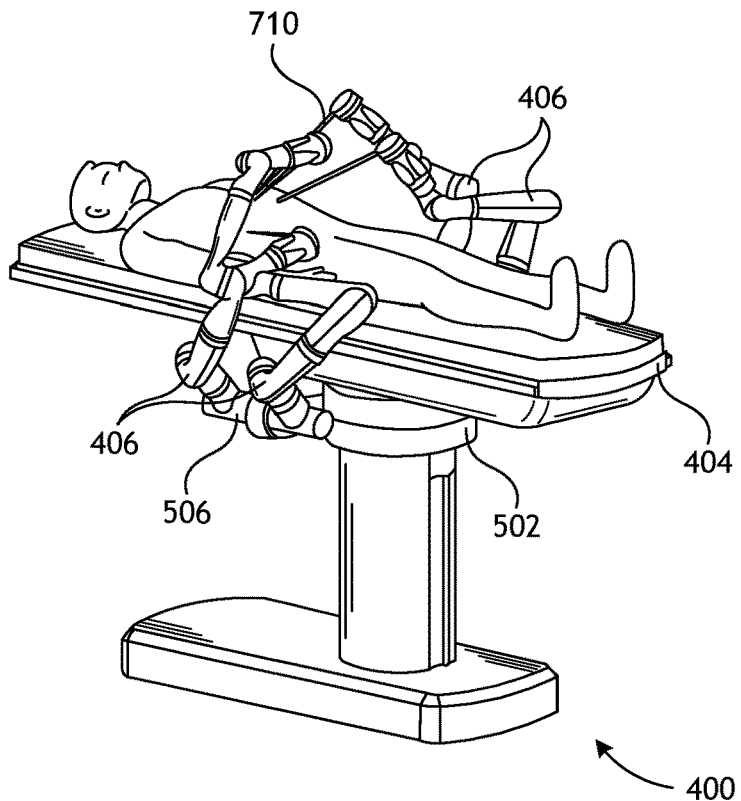
FIG. 7B illustrates an embodiment of a table-based robotic system configured for a laparoscopic procedure.

FIG. 7A illustrates an embodiment of the robotically-enabled table-based system 400 configured for a ureteroscopy procedure. In ureteroscopy, the table 404 may include a swivel portion 702 for positioning a patient off-angle from the column 402 and the table base 508. The swivel portion 702 may rotate or pivot around a pivot point (e.g., located below the patient's head) in order to position the bottom portion of the swivel portion 702 away from the column 402. For example, the pivoting of the swivel portion 702 allows a C-arm (not shown) to be positioned over the patient's lower abdomen without competing for space with the column (not shown) below table 404. By rotating the carriage (not shown) around the column 402, the robotic arms 406 may directly insert a ureteroscope 704 along a virtual rail 706 into the patient's groin area to reach the urethra. In ureteroscopy, stirrups 708 may also be fixed to the swivel portion 702 of the table 404 to support the position of the patient's legs during the procedure and allow clear access to the patient's groin area.

FIG. 7B illustrates an embodiment of the system 400 configured for a laparoscopic procedure. In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. As shown in FIG. 7B, the carriages 502 of the system 400 may be rotated and vertically adjusted to position pairs of the robotic arms 406 on opposite sides of the table 404, such that an instrument 710 may be positioned using the arm mounts 506 to be passed through minimal incisions on both sides of the patient to reach his/her abdominal cavity.

Figure 7C:
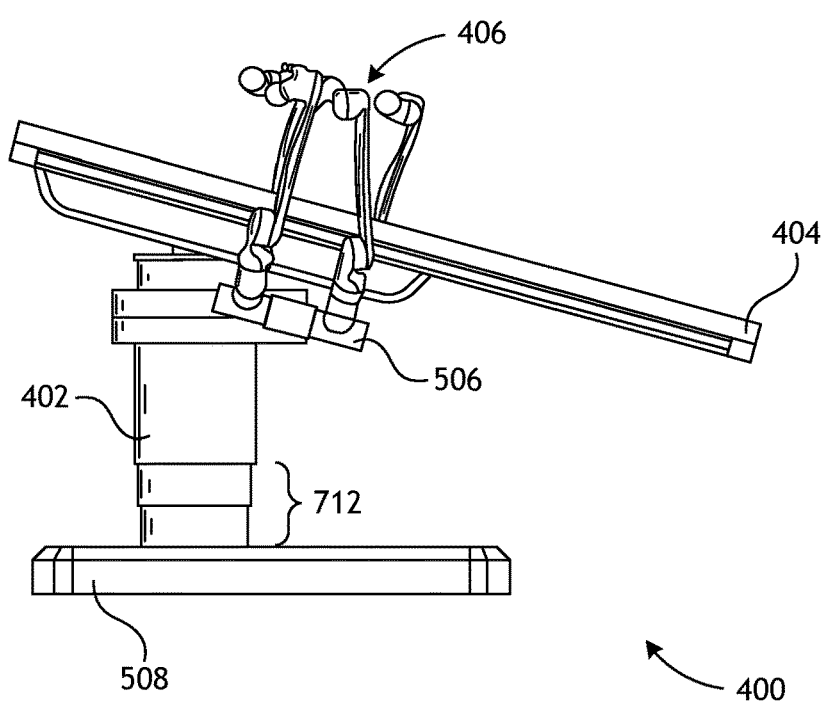
FIG. 7C illustrates an embodiment of the table-based robotic system of FIGS. 4-7B with pitch or tilt adjustment.

To accommodate laparoscopic procedures, the system 400 may also tilt the platform to a desired angle. FIG. 7C illustrates an embodiment of the system 400 with pitch or tilt adjustment. As shown in FIG. 7C, the system 400 may accommodate tilt of the table 404 to position one portion of the table 404 at a greater distance from the floor than the other. Additionally, the arm mounts 506 may rotate to match the tilt such that the arms 406 maintain the same planar relationship with table 404. To accommodate steeper angles, the column 402 may also include telescoping portions 712 that allow vertical extension of the column 402 to keep the table 404 from touching the floor or colliding with the base 508.

Figure 8:
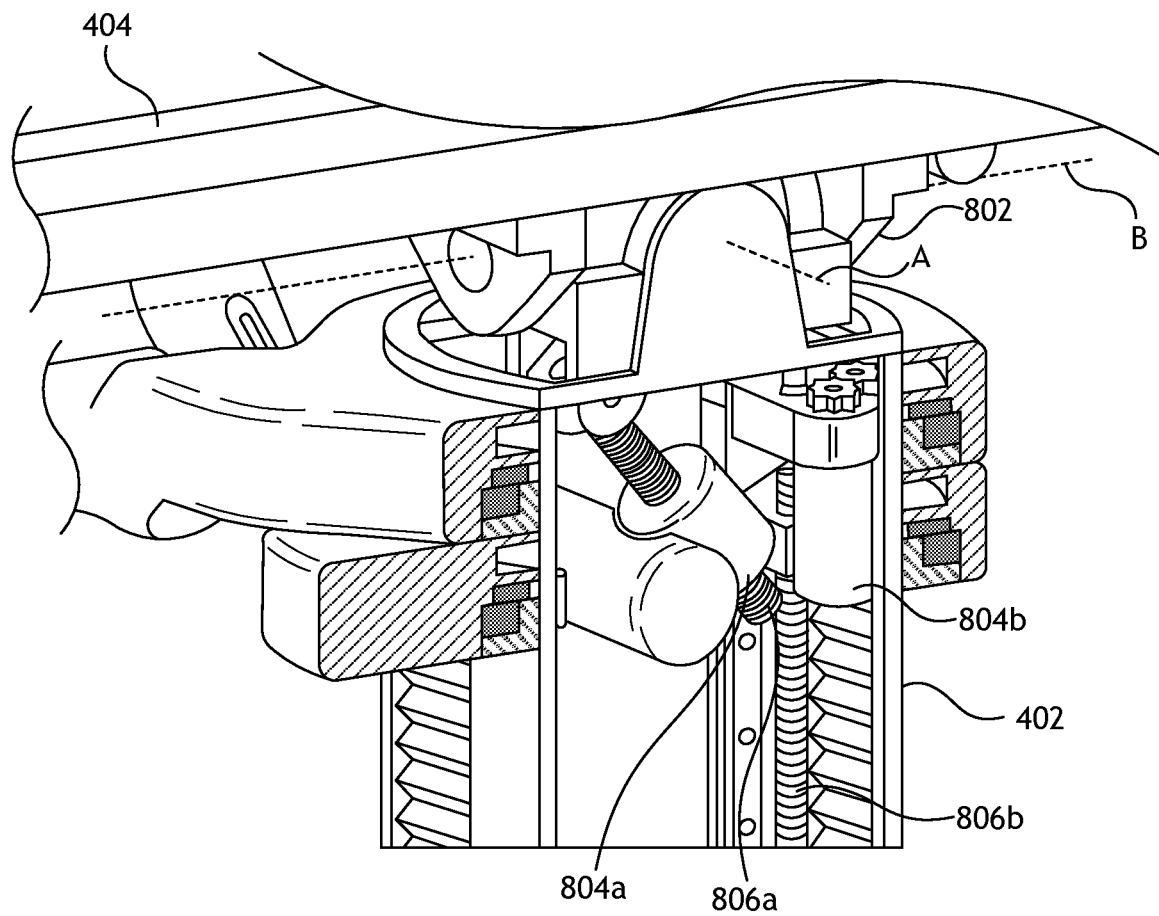
FIG. 8 provides a detailed illustration of the interface between the table and the column of the table-based robotic system of FIGS. 4-7.

FIG. 8 provides a detailed illustration of the interface between the table 404 and the column 402. Pitch rotation mechanism 802 may be configured to alter the pitch angle of the table 404 relative to the column 402 in multiple degrees of freedom. The pitch rotation mechanism 802 may be enabled by the positioning of orthogonal axes A and B at the column-table interface, each axis actuated by a separate motor 804a and 804b responsive to an electrical pitch angle command. Rotation along one screw 806a would enable tilt adjustments in one axis A, while rotation along another screw 806b would enable tilt adjustments along the other axis B. In some embodiments, a ball joint can be used to alter the pitch angle of the table 404 relative to the column 402 in multiple degrees of freedom.

For example, pitch adjustments are particularly useful when trying to position the table in a Trendelenburg position, i.e., position the patient's lower abdomen at a higher position from the floor than the patient's lower abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 9A:
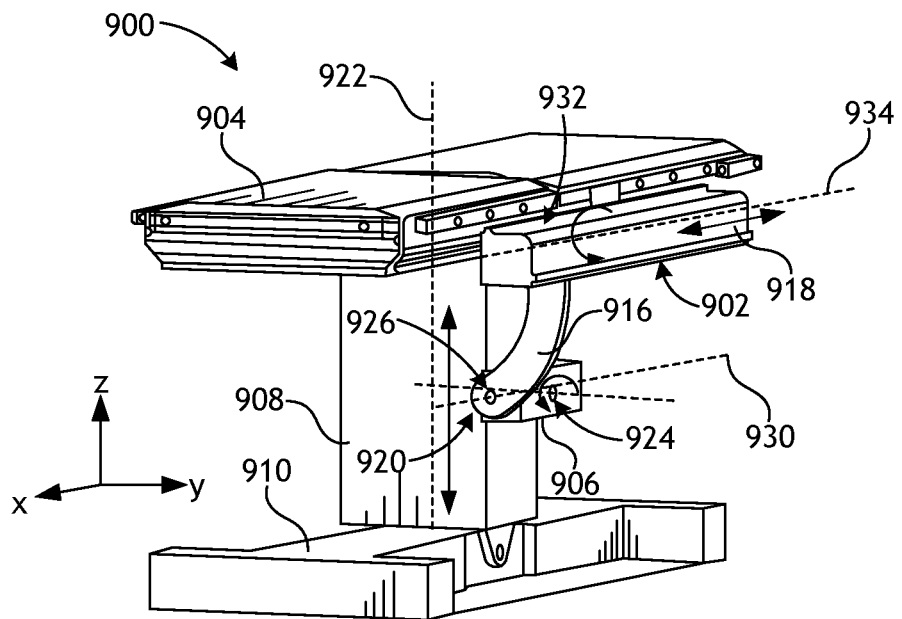
FIG. 9A illustrates an alternative embodiment of a table-based robotic system.
Figure 9B:
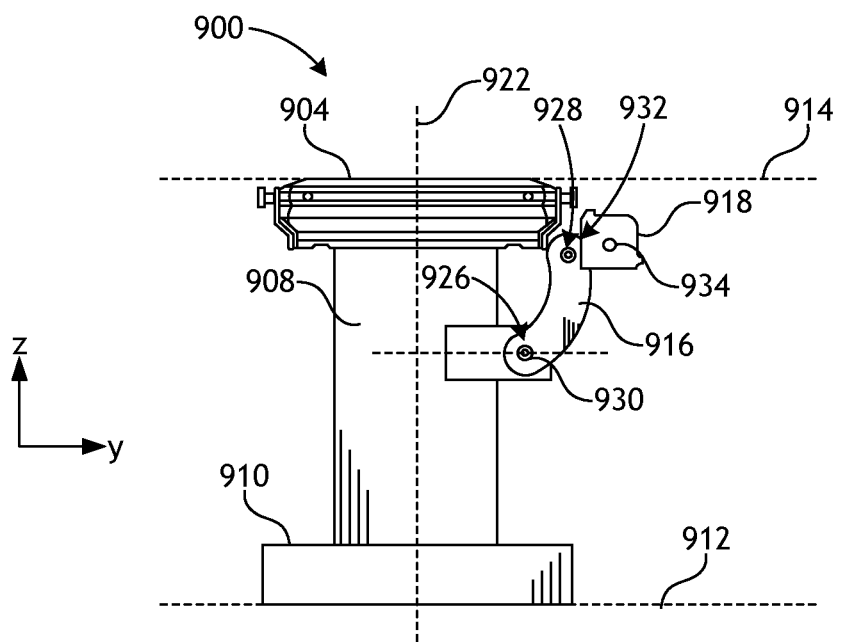
FIG. 9B illustrates an end view of the table-based robotic system of FIG. 9A.

FIGS. 9A and 9B illustrate isometric and end views, respectively, of an alternative embodiment of a table-based surgical robotics system 900. The surgical robotics system 900 includes one or more adjustable arm supports 902 that can be configured to support one or more robotic arms (see, for example, FIG. 9C) relative to a table 904. In the illustrated embodiment, a single adjustable arm support 902 is shown, though an additional arm support can be provided on an opposite side of the table 904. The adjustable arm support 902 can be configured so that it can move relative to the table 904 to adjust and/or vary the position of the adjustable arm support 902 and/or any robotic arms mounted thereto relative to the table 904. For example, the adjustable arm support 902 may be adjusted in one or more degrees of freedom relative to the table 904. The adjustable arm support 902 provides high versatility to the system 900, including the ability to easily stow the one or more adjustable arm supports 902 and any robotics arms attached thereto beneath the table 904. The adjustable arm support 902 can be elevated from the stowed position to a position below an upper surface of the table 904. In other embodiments, the adjustable arm support 902 can be elevated from the stowed position to a position above an upper surface of the table 904.

The adjustable arm support 902 can provide several degrees of freedom, including lift, lateral translation, tilt, etc. In the illustrated embodiment of FIGS. 9A and 9B, the arm support 902 is configured with four degrees of freedom, which are illustrated with arrows in FIG. 9A. A first degree of freedom allows for adjustment of the adjustable arm support 902 in the z-direction ("Z-lift"). For example, the adjustable arm support 902 can include a carriage 906 configured to move up or down along or relative to a column 908 supporting the table 904. A second degree of freedom can allow the adjustable arm support 902 to tilt. For example, the adjustable arm support 902 can include a rotary joint, which can allow the adjustable arm support 902 to be aligned with the bed in a Trendelenburg position. A third degree of freedom can allow the adjustable arm support 902 to "pivot up," which can be used to adjust a distance between a side of the table 904 and the adjustable arm support 902. A fourth degree of freedom can permit translation of the adjustable arm support 902 along a longitudinal length of the table.

The surgical robotics system 900 in FIGS. 9A and 9B can comprise a table 904 supported by a column 908 that is mounted to a base 910. The base 910 and the column 908 support the table 904 relative to a support surface. A floor axis 912 and a support axis 914 are shown in FIG. 9B.

The adjustable arm support 902 can be mounted to the column 908. In other embodiments, the arm support 902 can be mounted to the table 904 or the base 910. The adjustable arm support 902 can include a carriage 906, a bar or rail connector 916 and a bar or rail 918. In some embodiments, one or more robotic arms mounted to the rail 918 can translate and move relative to one another.

The carriage 906 can be attached to the column 908 by a first joint 920, which allows the carriage 906 to move relative to the column 908 (e.g., such as up and down a first or vertical axis 922). The first joint 920 can provide the first degree of freedom ("Z-lift") to the adjustable arm support 902. The adjustable arm support 902 can include a second joint 924, which provides the second degree of freedom (tilt) for the adjustable arm support 902. The adjustable arm support 902 can include a third joint 926, which can provide the third degree of freedom ("pivot up") for the adjustable arm support 902. An additional joint 928 (shown in FIG. 9B) can be provided that mechanically constrains the third joint 926 to maintain an orientation of the rail 918 as the rail connector 916 is rotated about a third axis 930. The adjustable arm support 902 can include a fourth joint 932, which can provide a fourth degree of freedom (translation) for the adjustable arm support 902 along a fourth axis 934.

Figure 9C:
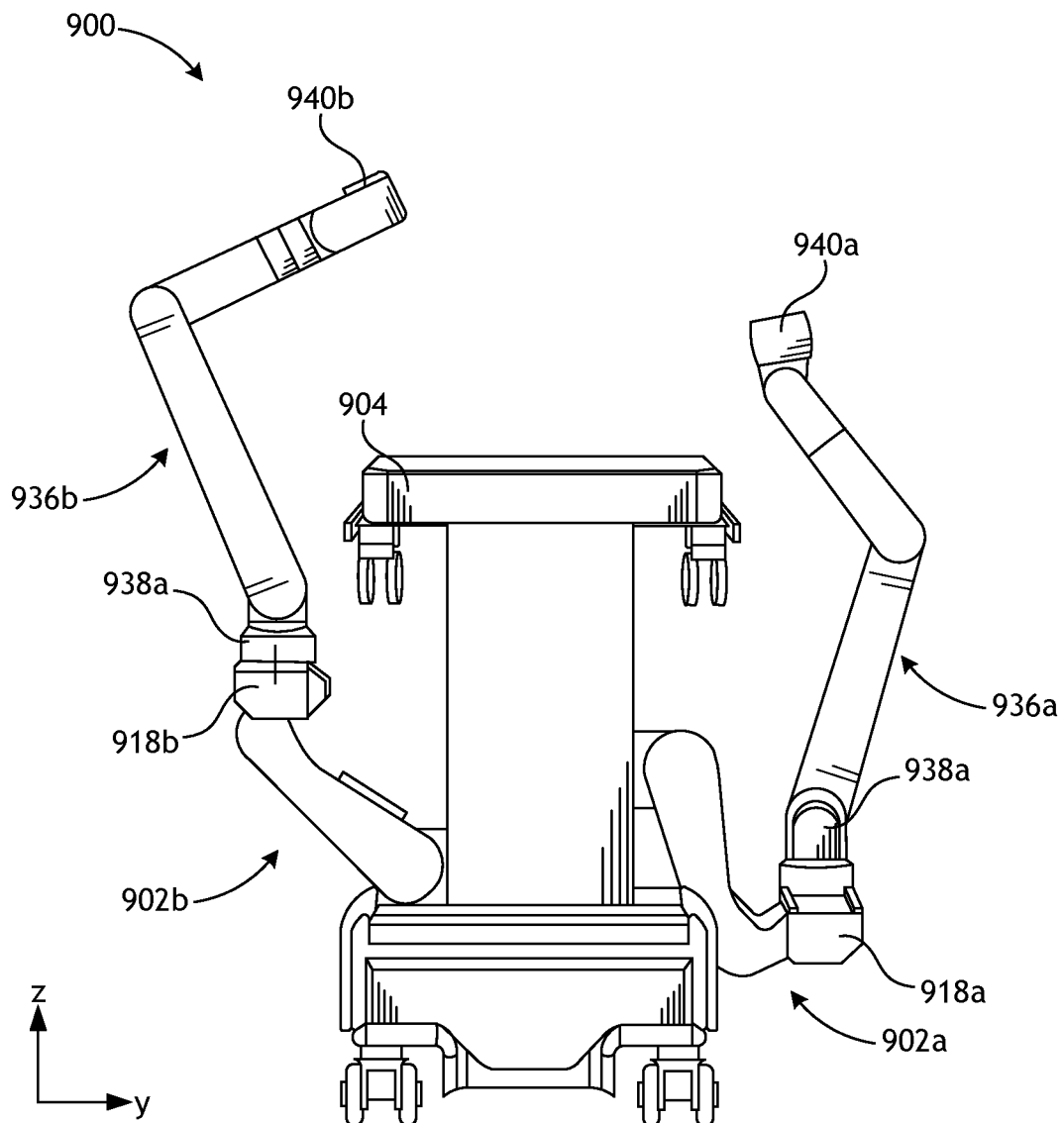
FIG. 9C illustrates an end view of a table-based robotic system with robotic arms attached thereto.

FIG. 9C illustrates an end view of the surgical robotics system 900 with two adjustable arm supports 902a and 902b mounted on opposite sides of the table 904. A first robotic arm 936a is attached to the first bar or rail 918a of the first adjustable arm support 902a. The first robotic arm 936a includes a base 938a attached to the first rail 918a. The distal end of the first robotic arm 936a includes an instrument drive mechanism or input 940a that can attach to one or more robotic medical instruments or tools. Similarly, the second robotic arm 936b includes a base 938a attached to the second rail 918b. The distal end of the second robotic arm 936b includes an instrument drive mechanism or input 940b configured to attach to one or more robotic medical instruments or tools.

In some embodiments, one or more of the robotic arms 936a,b comprises an arm with seven or more degrees of freedom. In some embodiments, one or more of the robotic arms 936a,b can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 938a,b (1-degree of freedom including translation). In some embodiments, the insertion degree of freedom can be provided by the robotic arm 936a,b, while in other embodiments, the instrument itself provides insertion via an instrument-based insertion architecture.

C. Instrument Driver & Interface.

The end effectors of a system's robotic arms comprise (i) an instrument driver (alternatively referred to as "tool driver," "instrument drive mechanism," "instrument device manipulator," and "drive input") that incorporate electro-mechanical means for actuating the medical instrument, and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 10:
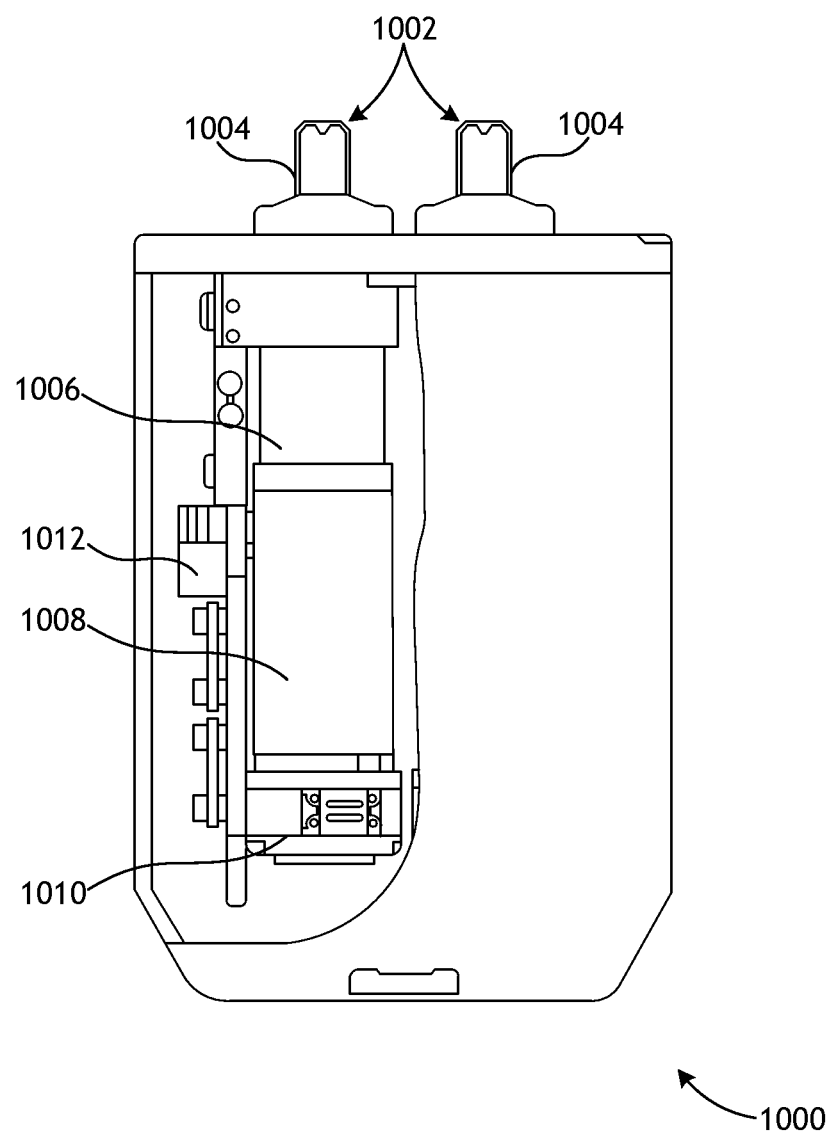
FIG. 10 illustrates an exemplary instrument driver.

FIG. 10 illustrates an example instrument driver 1000, according to one or more embodiments. Positioned at the distal end of a robotic arm, the instrument driver 1000 comprises of one or more drive outputs 1002 arranged with parallel axes to provide controlled torque to a medical instrument via corresponding drive shafts 1004. Each drive output 1002 comprises an individual drive shaft 1004 for interacting with the instrument, a gear head 1006 for converting the motor shaft rotation to a desired torque, a motor 1008 for generating the drive torque, and an encoder 1010 to measure the speed of the motor shaft and provide feedback to control circuitry 1012, which can also be used for receiving control signals and actuating the drive output 1002. Each drive output 1002 being independent controlled and motorized, the instrument driver 1000 may provide multiple (at least two shown in FIG. 10) independent drive outputs to the medical instrument. In operation, the control circuitry 1012 receives a control signal, transmits a motor signal to the motor 1008, compares the resulting motor speed as measured by the encoder 1010 with the desired speed, and modulates the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise of a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 11:
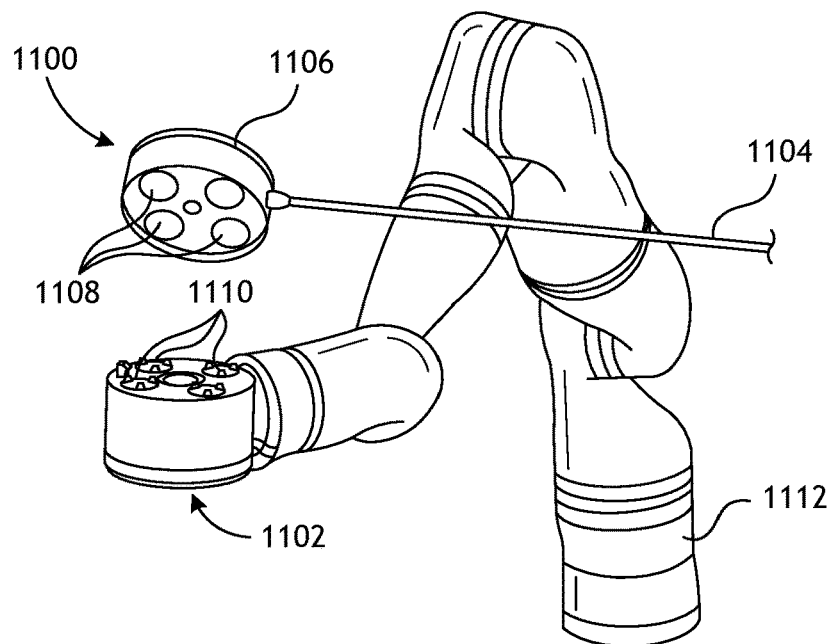
FIG. 11 illustrates an exemplary medical instrument with a paired instrument driver.

FIG. 11 illustrates an example medical instrument 1100 with a paired instrument driver 1102. Like other instruments designed for use with a robotic system, the medical instrument 1100 (alternately referred to as a "surgical tool") comprises an elongated shaft 1104 (or elongate body) and an instrument base 1106. The instrument base 1106, also referred to as an "instrument handle" due to its intended design for manual interaction by the physician, may generally comprise rotatable drive inputs 1108, e.g., receptacles, pulleys or spools, that are designed to be mated with drive outputs 1110 that extend through a drive interface on the instrument driver 1102 at the distal end of a robotic arm 1112. When physically connected, latched, and/or coupled, the mated drive inputs 1108 of the instrument base 1106 may share axes of rotation with the drive outputs 1110 in the instrument driver 1102 to allow the transfer of torque from the drive outputs 1110 to the drive inputs 1108. In some embodiments, the drive outputs 1110 may comprise splines that are designed to mate with receptacles on the drive inputs 1108.

The elongated shaft 1104 is designed to be delivered through either an anatomical opening or lumen, e.g., as in endoscopy, or a minimally invasive incision, e.g., as in laparoscopy. The elongated shaft 1104 may be either flexible (e.g., having properties similar to an endoscope) or rigid (e.g., having properties similar to a laparoscope) or contain a customized combination of both flexible and rigid portions. When designed for laparoscopy, the distal end of the shaft 1104 may be connected to an end effector extending from a jointed wrist formed from a clevis with at least one degree of freedom and a surgical tool or medical instrument, such as, for example, a grasper or scissors, that may be actuated based on force from the tendons as the drive inputs 1008 rotate in response to torque received from the drive outputs 1110 of the instrument driver 1102. When designed for endoscopy, the distal end of the flexible elongated shaft 1104 may include a steerable or controllable bending section that may be articulated and bent based on torque received from the drive outputs 1110 of the instrument driver 1102.

In some embodiments, torque from the instrument driver 1102 is transmitted down the elongated shaft 1104 using tendons along the shaft 1104. These individual tendons, such as pull wires, may be individually anchored to individual drive inputs 1108 within the instrument handle 1106. From the handle 1106, the tendons are directed down one or more pull lumens along the elongated shaft 1104 and anchored at the distal portion of the elongated shaft 1104, or in the wrist at the distal portion of the elongated shaft. During a surgical procedure, such as a laparoscopic, endoscopic, or a hybrid procedure, these tendons may be coupled to a distally mounted end effector, such as a wrist, a grasper, or scissors. Under such an arrangement, torque exerted on the drive inputs 1108 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at distal end of the elongated shaft 1104, where tension from the tendon cause the grasper to close.

In endoscopy, the tendons may be coupled to a bending or articulating section positioned along the elongated shaft 1104 (e.g., at the distal end) via adhesive, control ring, or other mechanical fixation. When fixedly attached to the distal end of a bending section, torque exerted on drive inputs 1108 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing there between may be altered or engineered for specific purposes, wherein tighter spiraling exhibits lesser shaft compression under load forces, while lower amounts of spiraling results in greater shaft compression under load forces, but also exhibits limits bending. On the other end of the spectrum, the pull lumens may be directed parallel to the longitudinal axis of the elongated shaft 1104 to allow for controlled articulation in the desired bending or articulable sections.

In endoscopy, the elongated shaft 1104 houses a number of components to assist with the robotic procedure. The shaft may comprise of a working channel for deploying surgical tools (or medical instruments), irrigation, and/or aspiration to the operative region at the distal end of the shaft 1104. The shaft 1104 may also accommodate wires and/or optical fibers to transfer signals to/from an optical assembly at the distal tip, which may include of an optical camera. The shaft 1104 may also accommodate optical fibers to carry light from proximally-located light sources, such as light emitting diodes, to the distal end of the shaft.

At the distal end of the instrument 1100, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 11, the drive shaft axes, and thus the drive input axes, are orthogonal to the axis of the elongated shaft. This arrangement, however, complicates roll capabilities for the elongated shaft 1104. Rolling the elongated shaft 1104 along its axis while keeping the drive inputs 1108 static results in undesirable tangling of the tendons as they extend off the drive inputs 1108 and enter pull lumens within the elongated shaft 1104. The resulting entanglement of such tendons may disrupt any control algorithms intended to predict movement of the flexible elongated shaft during an endoscopic procedure.

Figure 12:
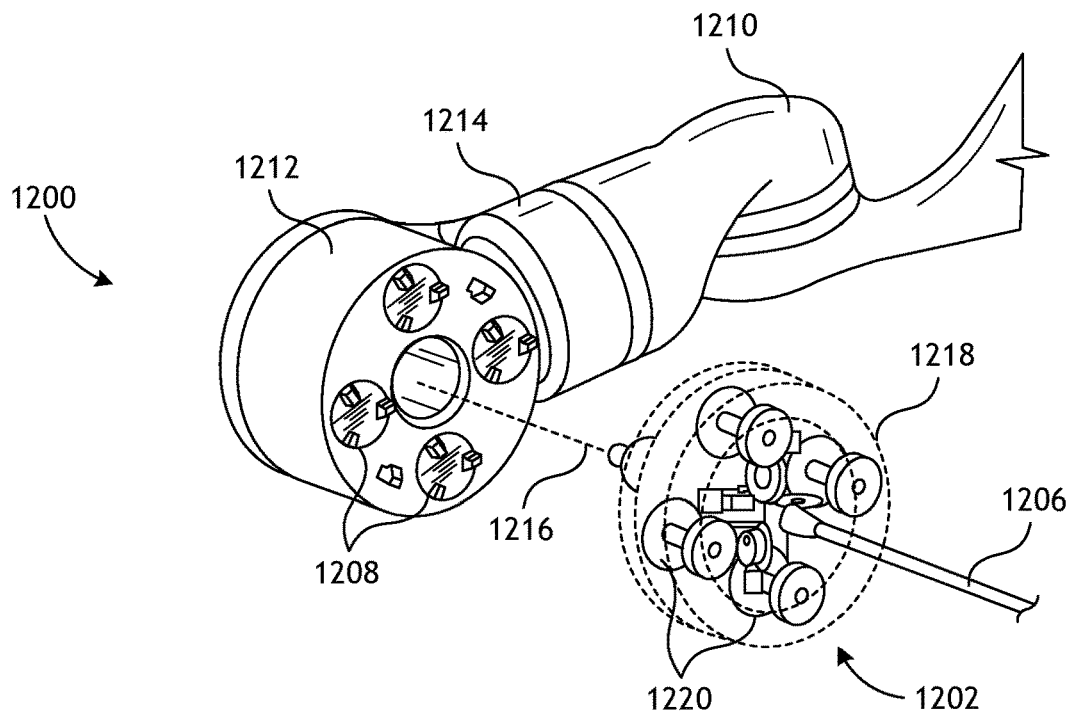
FIG. 12 illustrates an alternative design for an instrument driver and instrument where the axes of the drive units are parallel to the axis of the elongated shaft of the instrument.

FIG. 12 illustrates an alternative design for a circular instrument driver 1200 and corresponding instrument 1202 (alternately referred to as a "surgical tool") where the axes of the drive units are parallel to the axis of the elongated shaft 1206 of the instrument 1202. As shown, the instrument driver 1200 comprises four drive units with corresponding drive outputs 1208 aligned in parallel at the end of a robotic arm 1210. The drive units and their respective drive outputs 1208 are housed in a rotational assembly 1212 of the instrument driver 1200 that is driven by one of the drive units within the assembly 1212. In response to torque provided by the rotational drive unit, the rotational assembly 1212 rotates along a circular bearing that connects the rotational assembly 1212 to a non-rotational portion 1214 of the instrument driver 1200. Power and control signals may be communicated from the non-rotational portion 1214 of the instrument driver 1200 to the rotational assembly 1212 through electrical contacts maintained through rotation by a brushed slip ring connection (not shown). In other embodiments, the rotational assembly 1212 may be responsive to a separate drive unit that is integrated into the non-rotatable portion 1214, and thus not in parallel with the other drive units. The rotational assembly 1212 allows the instrument driver 1200 to rotate the drive units and their respective drive outputs 1208 as a single unit around an instrument driver axis 1216.

Like earlier disclosed embodiments, the instrument 1202 may include an elongated shaft 1206 and an instrument base 1218 (shown in phantom) including a plurality of drive inputs 1220 (such as receptacles, pulleys, and spools) that are configured to mate with the drive outputs 1208 of the instrument driver 1200. Unlike prior disclosed embodiments, the instrument shaft 1206 extends from the center of the instrument base 1218 with an axis substantially parallel to the axes of the drive inputs 1220, rather than orthogonal as in the design of FIG. 11.

When coupled to the rotational assembly 1212 of the instrument driver 1200, the medical instrument 1202, comprising instrument base 1218 and instrument shaft 1206, rotates in combination with the rotational assembly 1212 about the instrument driver axis 1216. Since the instrument shaft 1206 is positioned at the center of the instrument base 1218, the instrument shaft 1206 is coaxial with the instrument driver axis 1216 when attached. Thus, rotation of the rotational assembly 1212 causes the instrument shaft 1206 to rotate about its own longitudinal axis. Moreover, as the instrument base 1218 rotates with the instrument shaft 1206, any tendons connected to the drive inputs 1220 in the instrument base 1218 are not tangled during rotation. Accordingly, the parallelism of the axes of the drive outputs 1208, the drive inputs 1220, and the instrument shaft 1206 allows for the shaft rotation without tangling any control tendons.

Figure 13:
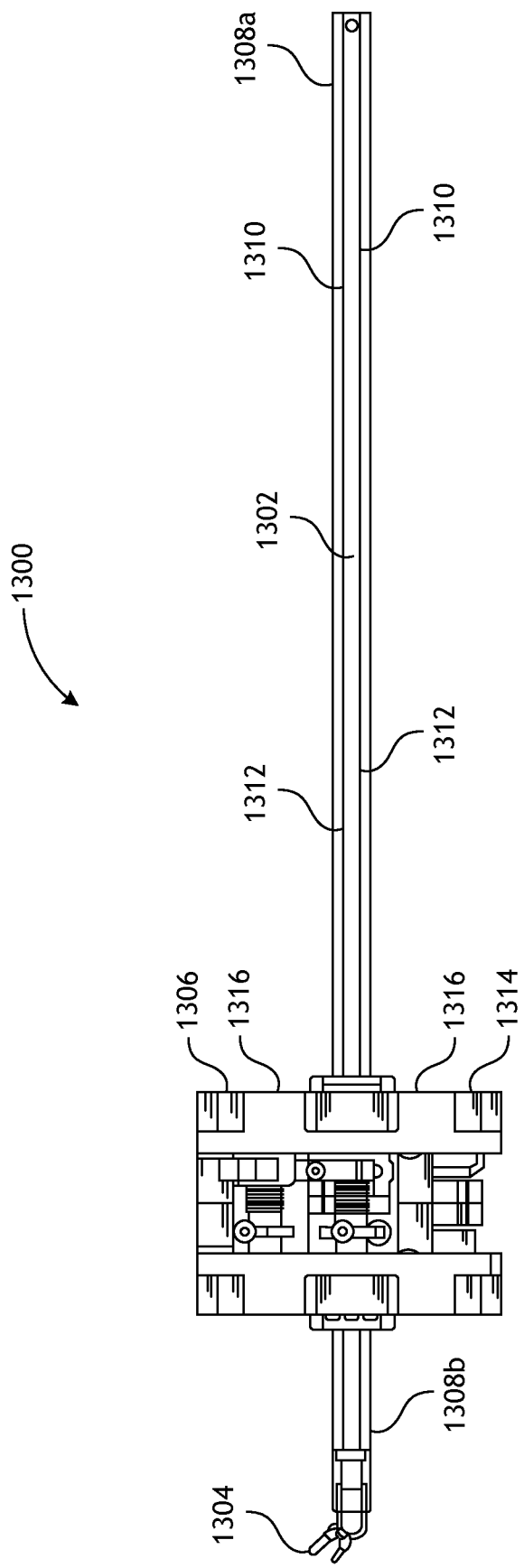
FIG. 13 illustrates an instrument having an instrument-based insertion architecture.

FIG. 13 illustrates a medical instrument 1300 having an instrument based insertion architecture in accordance with some embodiments. The instrument 1300 (alternately referred to as a "surgical tool") can be coupled to any of the instrument drivers discussed herein above and, as illustrated, can include an elongated shaft 1302, an end effector 1304 connected to the shaft 1302, and a handle 1306 coupled to the shaft 1302. The elongated shaft 1302 comprises a tubular member having a proximal portion 1308a and a distal portion 1308b. The elongated shaft 1302 comprises one or more channels or grooves 1310 along its outer surface and configured to receive one or more wires or cables 1312 therethrough. One or more cables 1312 thus run along an outer surface of the elongated shaft 1302. In other embodiments, the cables 1312 can also run through the elongated shaft 1302. Manipulation of the cables 1312 (e.g., via an instrument driver) results in actuation of the end effector 1304.

The instrument handle 1306, which may also be referred to as an instrument base, may generally comprise an attachment interface 1314 having one or more mechanical inputs 1316, e.g., receptacles, pulleys or spools, that are designed to be reciprocally mated with one or more drive outputs on an attachment surface of an instrument driver.

In some embodiments, the instrument 1300 comprises a series of pulleys or cables that enable the elongated shaft 1302 to translate relative to the handle 1306. In other words, the instrument 1300 itself comprises an instrument-based insertion architecture that accommodates insertion of the instrument, thereby minimizing the reliance on a robot arm to provide insertion of the instrument 1300. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 14:
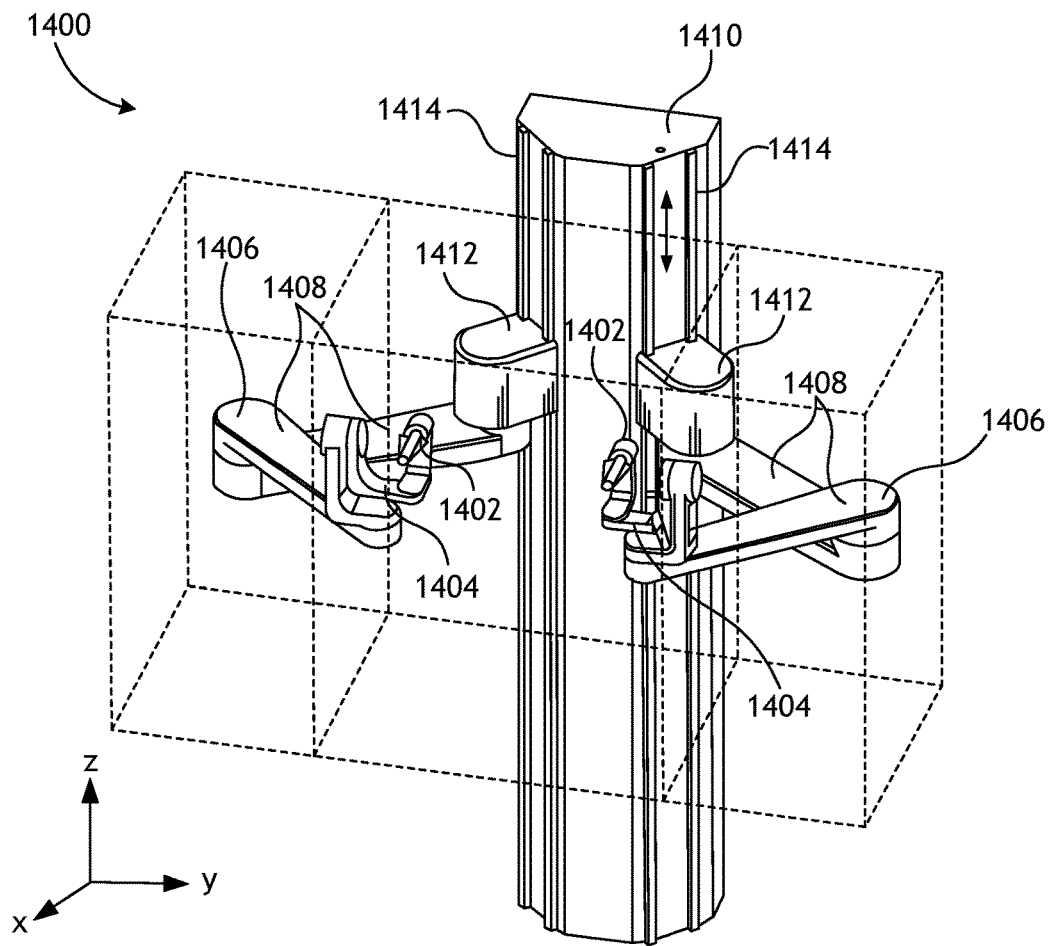
FIG. 14 illustrates an exemplary controller.

FIG. 14 is a perspective view of an embodiment of a controller 1400. In the present embodiment, the controller 1400 comprises a hybrid controller that can have both impedance and admittance control. In other embodiments, the controller 1400 can utilize just impedance or passive control. In other embodiments, the controller 1400 can utilize just admittance control. By being a hybrid controller, the controller 1400 advantageously can have a lower perceived inertia while in use.

In the illustrated embodiment, the controller 1400 is configured to allow manipulation of two medical instruments, and includes two handles 1402. Each of the handles 1402 is connected to a gimbal 1404, and each gimbal 1404 is connected to a positioning platform 1406.

As shown in FIG. 14, each positioning platform 1406 includes a selective compliance assembly robot arm (SCARA) 1408 coupled to a column 1410 by a prismatic joint 1412. The prismatic joints 1412 are configured to translate along the column 1410 (e.g., along rails 1414) to allow each of the handles 1402 to be translated in the z-direction, providing a first degree of freedom. The SCARA arm 1408 is configured to allow motion of the handle 1402 in an x-y plane, providing two additional degrees of freedom.

In some embodiments, one or more load cells are positioned in the controller 1400. For example, in some embodiments, a load cell (not shown) is positioned in the body of each of the gimbals 1404. By providing a load cell, portions of the controller 1400 are capable of operating under admittance control, thereby advantageously reducing the perceived inertia of the controller 1400 while in use. In some embodiments, the positioning platform 1406 is configured for admittance control, while the gimbal 1404 is configured for impedance control. In other embodiments, the gimbal 1404 is configured for admittance control, while the positioning platform 1406 is configured for impedance control. Accordingly, for some embodiments, the translational or positional degrees of freedom of the positioning platform 1406 can rely on admittance control, while the rotational degrees of freedom of the gimbal 1404 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as pre-operative mapping, computer vision, real-time EM tracking, and robot command data may be used individually or in combination to achieve a radiation-free operating environment. In other cases, where radiation-based imaging modalities are still used, the pre-operative mapping, computer vision, real-time EM tracking, and robot command data may be used individually or in combination to improve upon the information obtained solely through radiation-based imaging modalities.

Figure 15:
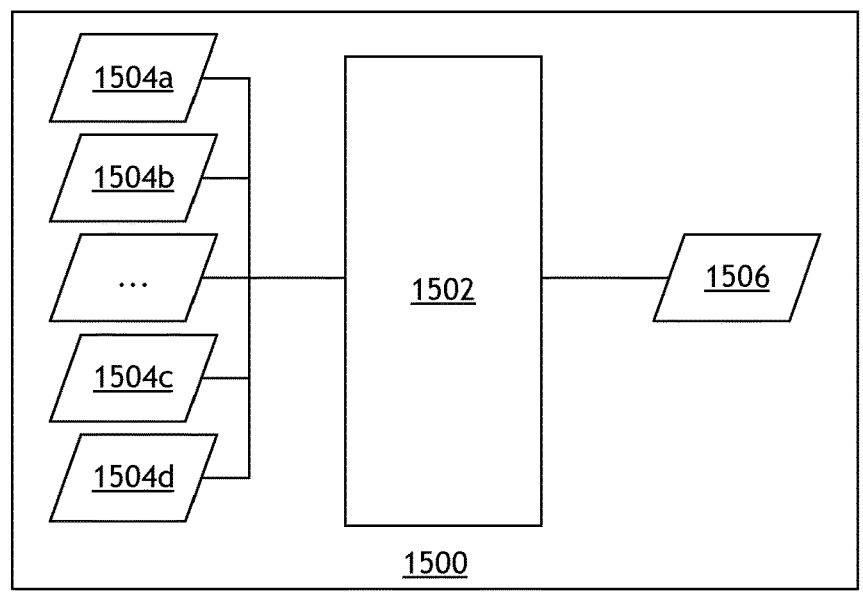
FIG. 15 depicts a block diagram illustrating a localization system that estimates a location of one or more elements of the robotic systems of FIGS. 1-7C, such as the location of the instrument of FIGS. 11-13, in accordance to an example embodiment.

FIG. 15 is a block diagram illustrating a localization system 1500 that estimates a location of one or more elements of the robotic system, such as the location of the instrument, in accordance to an example embodiment. The localization system 1500 may be a set of one or more computer devices configured to execute one or more instructions. The computer devices may be embodied by a processor (or processors) and computer-readable memory in one or more components discussed above. By way of example and not limitation, the computer devices may be in the tower 112 shown in FIG. 1, the cart 102 shown in FIGS. 1-3B, the beds shown in FIGS. 4-9, etc.

As shown in FIG. 15, the localization system 1500 may include a localization module 1502 that processes input data 1504a, 1504b, 1504c, and 1504d to generate location data 1506 for the distal tip of a medical instrument. The location data 1506 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 1504a-d are now described in greater detail. Pre-operative mapping may be accomplished through the use of the collection of low dose CT scans. Pre-operative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as center-line geometry may be determined and approximated from the CT images to develop a three-dimensional volume of the patient's anatomy, referred to as model data 1504a (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data 1504b. The localization module 1502 may process the vision data 1504b to enable one or more vision-based location tracking. For example, the preoperative model data may be used in conjunction with the vision data 1504b to enable computer vision-based tracking of the medical instrument (e.g., an endoscope or an instrument advance through a working channel of the endoscope). For example, using the preoperative model data 1504a, the robotic system may generate a library of expected endoscopic images from the model based on the expected path of travel of the endoscope, each image linked to a location within the model. Intra-operatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 1502 may identify circular geometries in the preoperative model data 1504a that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 1504b to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 1502 may use real-time EM tracking to generate a real-time location of the endoscope in a global coordinate system that may be registered to the patient's anatomy, represented by the preoperative model. In EM tracking, an EM sensor (or tracker) comprising of one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 1504c. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intra-operatively "registered" to the patient anatomy (e.g., the preoperative model) in order to determine the geometric transformation that aligns a single location in the coordinate system with a position in the pre-operative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 1504d may also be used by the localization module 1502 to provide localization data 1506 for the robotic system. Device pitch and yaw resulting from articulation commands may be determined during pre-operative calibration. Intra-operatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 15 shows, a number of other input data can be used by the localization module 1502. For example, although not shown in FIG. 15, an instrument utilizing shape-sensing fiber can provide shape data that the localization module 1502 can use to determine the location and shape of the instrument.

The localization module 1502 may use the input data 1504*a-d* in combination(s). In some cases, such a combination may use a probabilistic approach where the localization module 1502 assigns a confidence weight to the location determined from each of the input data 1504*a-d*. Thus, where the EM data 1504*c* may not be reliable (as may be the case where there is EM interference) the confidence of the location determined by the EM data 1504*c* can be decrease and the localization module 1502 may rely more heavily on the vision data 1504*b* and/or the robotic command and kinematics data 1504*d*.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Introduction.

Embodiments of this disclosure relate to systems and techniques for articulating an end effector for a robotic surgical tool. The robotic surgical tool may include a drive housing having a first end and at least one spline extending from the first end and including a drive gear that rotates with rotation of the spline. A carriage may be movably mounted to the spline for z-axis translation, and an elongate shaft extends from the carriage and through the first end. An end effector may be arranged at a distal end of the elongate shaft, and an articulable wrist interposes the end effector and the distal end of the shaft. An activating mechanism is housed in or otherwise carried by the carriage and is operatively coupled to the drive gear such that rotation of the drive gear correspondingly actuates the activating mechanism. As the activating mechanism actuates, the wrist correspondingly articulates the end effector in at least one plane.

3. Description.

Figure 16:
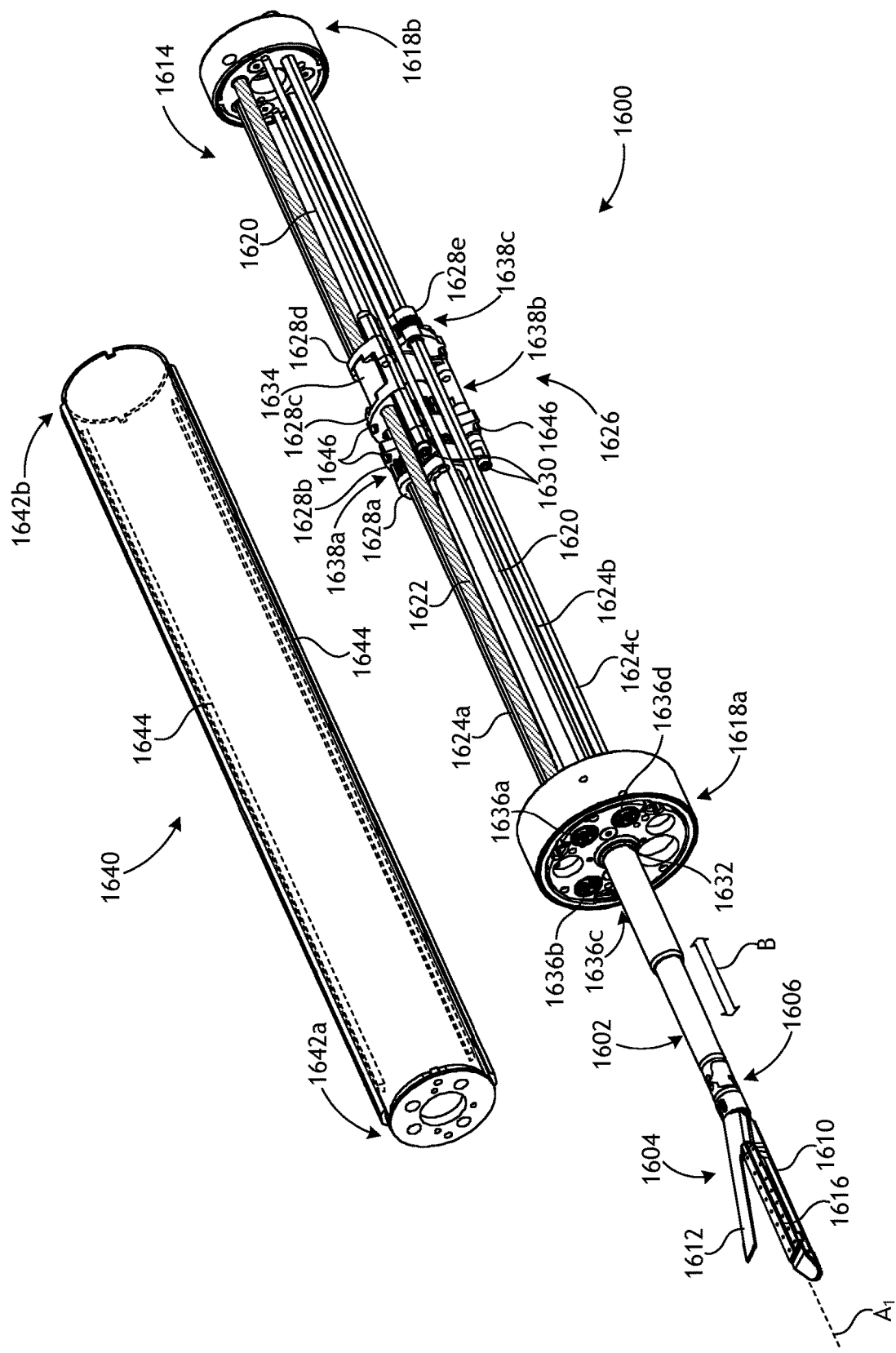
FIG. 16 is an isometric side view of an example surgical tool that may incorporate some or all of the principles of the present disclosure.

FIG. 16 is an isometric side view of an example surgical tool 1600 that may incorporate some or all of the principles of the present disclosure. The surgical tool 1600 may be similar in some respects to any of the medical instruments described above with reference to FIGS. 11-13 and, therefore, may be used in conjunction with a robotic surgical system, such as the robotically-enabled systems 100, 400, and 900 of FIGS. 1-13. As illustrated, the surgical tool 1600 includes an elongated shaft 1602, an end effector 1604 arranged at the distal end of the shaft 1602, and an articulable wrist 1606 (alternately referred to as a "wrist joint") that interposes and couples the end effector 1604 to the distal end of the shaft 1602.

The terms "proximal" and "distal" are defined herein relative to a robotic surgical system having an interface configured to mechanically and electrically couple the surgical tool 1600 to a robotic manipulator. The term "proximal" refers to the position of an element closer to the robotic manipulator and the term "distal" refers to the position of an element closer to the end effector 1604 and thus closer to the patient during operation. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

The surgical tool 1600 can have any of a variety of configurations capable of performing one or more surgical functions. In the illustrated embodiment, the end effector 1604 comprises a surgical stapler, alternately referred to as an "endocutter," configured to cut and staple (fasten) tissue. As illustrated, the end effector 1604 includes opposing jaws 1610, 1612 configured to move (articulate) between open and closed positions. Alternatively, the end effector 1604 may comprise other types of instruments requiring opposing jaws such as, but not limited to, other surgical staplers (e.g., circular and linear staplers), tissue graspers, surgical scissors, advanced energy vessel sealers, clip appliers, needle drivers, a babcock including a pair of opposed grasping jaws, bipolar jaws (e.g., bipolar Maryland grasper, forceps, a fenestrated grasper, etc.), etc. In other embodiments, the end effector 1604 may instead comprise any end effector or instrument capable of being operated in conjunction with the presently disclosed robotic surgical systems and methods. Such end effectors or instruments include, but are not limited to, a suction irrigator, an endoscope (e.g., a camera), or any combination thereof.

One or both of the jaws 1610, 1612 may be configured to pivot to actuate the end effector 1604 between open and closed positions. In the illustrated example, the second jaw 1612 is rotatable (pivotable) relative to the first jaw 1610 to move between an open, unclamped position and a closed, clamped position. In other embodiments, however, the first jaw 1610 may move (rotate) relative to the second jaw 1612, without departing from the scope of the disclosure. In yet other embodiments, both jaws 1610, 1612 may move to actuate the end effector 1604 between open and closed positions.

In the illustrated example, the first jaw 1610 is referred to as a "cartridge" or "channel" jaw, and the second jaw 1612 is referred to as an "anvil" jaw. The first jaw 1610 may include a frame that houses or supports a staple cartridge, and the second jaw 1612 is pivotally supported relative to the first jaw 1610 and defines a surface that operates as an anvil to deform staples ejected from the staple cartridge during operation.

The wrist 1606 enables the end effector 1604 to articulate (pivot) relative to the shaft 1602 and thereby position the end effector 1604 at various desired orientations and locations relative to a surgical site. In the illustrated embodiment, the wrist 1606 is designed to allow the end effector 1604 to pivot (swivel) left and right relative to a longitudinal axis $A_1$ of the shaft 1602. In other embodiments, however, the wrist 1606 may be designed to provide multiple degrees of freedom, including one or more translational variables (i.e., surge, heave, and sway) and/or one or more rotational variables (i.e., Euler angles or roll, pitch, and yaw). The translational and rotational variables describe the position and orientation of a component of a surgical system (e.g., the end effector 1604) with respect to a given reference Cartesian frame. "Surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

In the illustrated embodiment, the pivoting motion at the wrist 1606 is limited to movement in a single plane, e.g., only yaw movement relative to the longitudinal axis $A_1$. The end effector 1604 is depicted in FIG. 16 in the unarticulated position where the longitudinal axis of the end effector 1604 is substantially aligned with the longitudinal axis $A_1$ of the shaft 1602, such that the end effector 1604 is at a substantially zero angle relative to the shaft 1602. In the articulated position, the longitudinal axis of the end effector 1604 would be angularly offset from the longitudinal axis $A_1$ such that the end effector 1604 would be oriented at a non-zero angle relative to the shaft 1602.

Still referring to FIG. 16, the surgical tool 1600 may include a drive housing 1614 that houses an actuation system designed to facilitate articulation of the wrist 1606 and actuation (operation) of the end effector 1604 (e.g., clamping, firing, rotation, articulation, energy delivery, etc.). The drive housing 1614, alternately referred to as a "stage," provides various coupling features that releasably couple the surgical tool 1600 to an instrument driver of a robotic surgical system, as described in more detail below.

The drive housing 1614 includes a plurality of drive members (obscured in FIG. 16) that extend to the wrist 1606 and the end effector 1604. Selective actuation of one or more of the drive members causes the end effector 1604 to articulate (pivot) relative to the shaft 1602 at the wrist 1606. Selective actuation of one or more other drive members causes the end effector 1604 to actuate (operate). Actuating the end effector 1604 may include closing and/or opening the jaws, 1610, 1612, and thereby enabling the end effector 1604 to grasp (clamp) onto tissue. Once tissue is grasped or clamped between the opposing jaws 1610, 1612, actuating the end effector 1604 may further include "firing" the end effector 1604, which may refer to causing a cutting element or knife (not visible) to advance distally within a slot 1616 defined in the first jaw 1610. As it moves distally, the cutting element transects any tissue grasped between the opposing jaws 1610, 1612. Moreover, as the cutting element advances distally, a plurality of staples contained within the staple cartridge (e.g., housed within the first jaw 1610) are urged (cammed) into deforming contact with corresponding anvil surfaces (e.g., pockets) provided on the second jaw 1612. The deployed staples may form multiple rows of staples that seal opposing sides of the transected tissue.

As illustrated, the drive housing 1614 has a first or "distal" end 1618a and a second or "proximal" end 1618b opposite the first end 1618a. The first end 1618a is alternately referred to as a "handle." In some embodiments, one or more struts 1620 (two shown) extend longitudinally between the first and second ends 1618a,b to help fix the distance between the first and second ends 1618a,b, provide advantageous structural stability to the drive housing 1614, and secure the first end 1618a to the second end 1618b. In other embodiments, however, the struts 1620 may be omitted, without departing from the scope of the disclosure.

The drive housing 1614 may also include a lead screw 1622 and one or more splines 1624, which also extend longitudinally between the first and second ends 1618a,b. In the illustrated embodiment, the drive housing 1614 includes a first spline 1624a, a second spline 1624b, and a third spline 1624c. While three splines 1624a-c are depicted in the drive housing 1614, more or less than three may be included, without departing from the scope of the disclosure. Unlike the struts 1620, the lead screw 1622 and the splines 1624a-c are rotatably mounted to the first and second ends 1618a,b. As described in more detail below, selective rotation of the lead screw 1622 and the splines 1624a-c causes various functions of the drive housing 1614 to transpire, such as translating the end effector 1604 along the longitudinal axis $A_1$ (e.g., z-axis translation) causing the end effector 1604 to articulate (pivot) at the wrist 1606, causing the jaws 1610, 1612 to open and close, and causing the end effector 1604 to fire (operate).

The drive housing 1614 further includes a carriage 1626 movably mounted along the lead screw 1622 and the splines 1624a-c and houses various activating mechanisms configured to cause operation of specific functions of the end effector 1604. The carriage 1626 may comprise two or more layers, shown in FIG. 16 as a first layer 1628a, a second layer 1628b, a third layer 1628c, a fourth layer 1628d, and a fifth layer 1628e. The lead screw 1622 and the splines 1624a-c each extend through portions of one or more of the layers 1628a-e to allow the carriage 1626 to translate along the longitudinal axis $A_1$ with respect to the lead screw 1622 and the splines 1624a-c. In some embodiments, the layers 1628a-e may be secured to each other in series using one or more mechanical fasteners 1630 (two visible) extending between the first layer 1628a and the fifth layer 1628e and through coaxially aligned holes defined in some or all of the layers 1628a-e. While five layers 1628a-e are depicted, more or less than five may be included in the carriage 1626, without departing from the scope of the disclosure.

The shaft 1602 is coupled to and extends distally from the carriage 1626 through the first end 1618a of the drive housing 1614. In the illustrated embodiment, for example, the shaft 1602 penetrates the first end 1618a at a central aperture 1632 defined through the first end 1618a. The carriage 1626 is movable between the first and second ends 1618a,b along the longitudinal axis $A_1$ (e.g., z-axis translation) and is thereby able to advance or retract the end effector 1604 relative to the drive housing 1614, as indicated by the arrows B. More specifically, in some embodiments, the carriage 1626 includes a carriage nut 1634 mounted to the lead screw 1622 and secured between the third and fourth layers 1628c,d. The outer surface of the lead screw 1622 defines outer helical threading and the carriage nut 1634 defines corresponding internal helical threading (not shown) matable with the outer helical threading of the lead screw 1622. As a result, rotation of the lead screw 1622 causes the carriage nut 1634 to advance or retract the carriage 1626 along the longitudinal axis $A_1$ and correspondingly advance or retract the end effector 1604 relative to the drive housing 1614.

As indicated above, the lead screw 1622 and the splines 1624a-c are rotatably mounted to the first and second ends 1618a,b. More specifically, the first end 1618a of the drive housing 1614 may include one or more rotatable drive inputs actuatable to independently drive (rotate) the lead screw 1622 and the splines 1624a-c. In the illustrated embodiment, the drive housing 1614 includes a first drive input 1636a, a second drive input 1636b, a third drive input 1636c (occluded by the shaft 1602, see FIG. 17B), and a fourth drive input 1636d. As described below, each drive input 1636a-d may be matable with a corresponding drive output of an instrument driver such that movement (rotation) of a given drive output correspondingly moves (rotates) the associated drive input 1636a-d and thereby rotates the mated lead screw 1622 or spline 1624a-c. While only four drive inputs 1636a-d are depicted, more or less than four may be included in the drive housing 1614, depending on the application.

The first drive input 1636a may be operatively coupled to the lead screw 1622 such that rotation of the first drive input 1636a correspondingly rotates the lead screw 1622, which causes the carriage nut 1634 and the carriage 1626 to advance or retract along the longitudinal axis $A_1$, depending on the rotational direction of the lead screw 1622. As used herein the phrase "operatively coupled" refers to a coupled engagement, either directly or indirectly, where movement of one component causes corresponding movement of another component. With respect to the first drive input 1636a being operatively coupled to the lead screw 1622, such operative coupling may be facilitated through intermeshed gears (not shown) arranged within the second end 1618a, but could alternatively be facilitated through other mechanical means, such as cables, pulleys, drive rods, direct couplings, etc., without departing from the scope of the disclosure.

The second drive input 1636b may be operatively coupled to the first spline 1624a such that rotation of the second drive input 1636b correspondingly rotates the first spline 1624a. In some embodiments, the first spline 1624a may be operatively coupled to a first activating mechanism 1638a of the carriage 1626, and the first activating mechanism 1638a may be operable to open and close the jaws 1610, 1612. Accordingly, rotating the second drive input 1636b will correspondingly actuate the first activating mechanism 1638a and thereby open or close the jaws 1610, 1612, depending on the rotational direction of the first spline 1624a.

The third drive input 1636c may be operatively coupled to the second spline 1624b such that rotation of the third drive input 1636c correspondingly rotates the second spline 1624b. In some embodiments, the second spline 1624b may be operatively coupled to a second activating mechanism 1638b of the carriage 1626, and the second activating mechanism 1638b may be operable to articulate the end effector 1604 at the wrist 1606. Accordingly, rotating the third drive input 1636c will correspondingly actuate the second activating mechanism 1638b and thereby cause the wrist 1606 to articulate in at least one degree of freedom, depending on the rotational direction of the second spline 1624b.

The fourth drive input 1636d may be operatively coupled to the third spline 1624c such that rotation of the fourth drive input 1636d correspondingly rotates the third spline 1624c. In some embodiments, the third spline 1624c may be operatively coupled to a third activating mechanism 1638c of the carriage 1626, and the third activating mechanism 1638c may be operable to fire the cutting element (knife) at the end effector 1604. Accordingly, rotating the fourth drive input 1636d will correspondingly actuate the third activating mechanism 1638c and thereby cause the knife to advance or retract, depending on the rotational direction of the third spline 1624c.

In the illustrated embodiment, and as described in more detail below, the activating mechanisms 1638a-c comprise intermeshed gearing assemblies including one or more drive gears driven by rotation of the corresponding spline 1624a-c and configured to drive one or more corresponding driven gears that cause operation of specific functions of the end effector 1604. It is further contemplated herein, however, that the activating mechanisms 1638a-c may be operated through other types of mechanical cooperation such as, but not limited to, belts or cables.

In some embodiments, the drive housing 1614 may include a shroud 1640 sized to receive and otherwise surround the carriage 1626, the lead screw 1622, and the splines 1624a-c. In the illustrated embodiment, the shroud 1640 comprises a tubular or cylindrical structure having a first end 1642a matable with the first end 1618a of the drive housing 1614, and a second end 1642b matable with the second end 1618b of the drive housing 1614. The carriage 1626, the lead screw 1622, and the splines 1624a-c can all be accommodated within the interior of the shroud 1640, and the carriage 1626 may engage and traverse (ride on) one or more rails 1644 (shown in phantom) fixed to the shroud 1640. The rails 1644 extend longitudinally and parallel to the lead screw 1622 and are sized to be received within corresponding notches 1646 defined on the outer periphery of the carriage 1626 and, more particularly, on the outer periphery of one or more of the carriage layers 1628a-e. As the carriage 1626 translates along the longitudinal axis $A_1$, the rails 1644 help maintain the angular position of the carriage 1626 and assume any torsional loading that might otherwise adversely affect movement or operation of the carriage 1626.

Figure 17A:
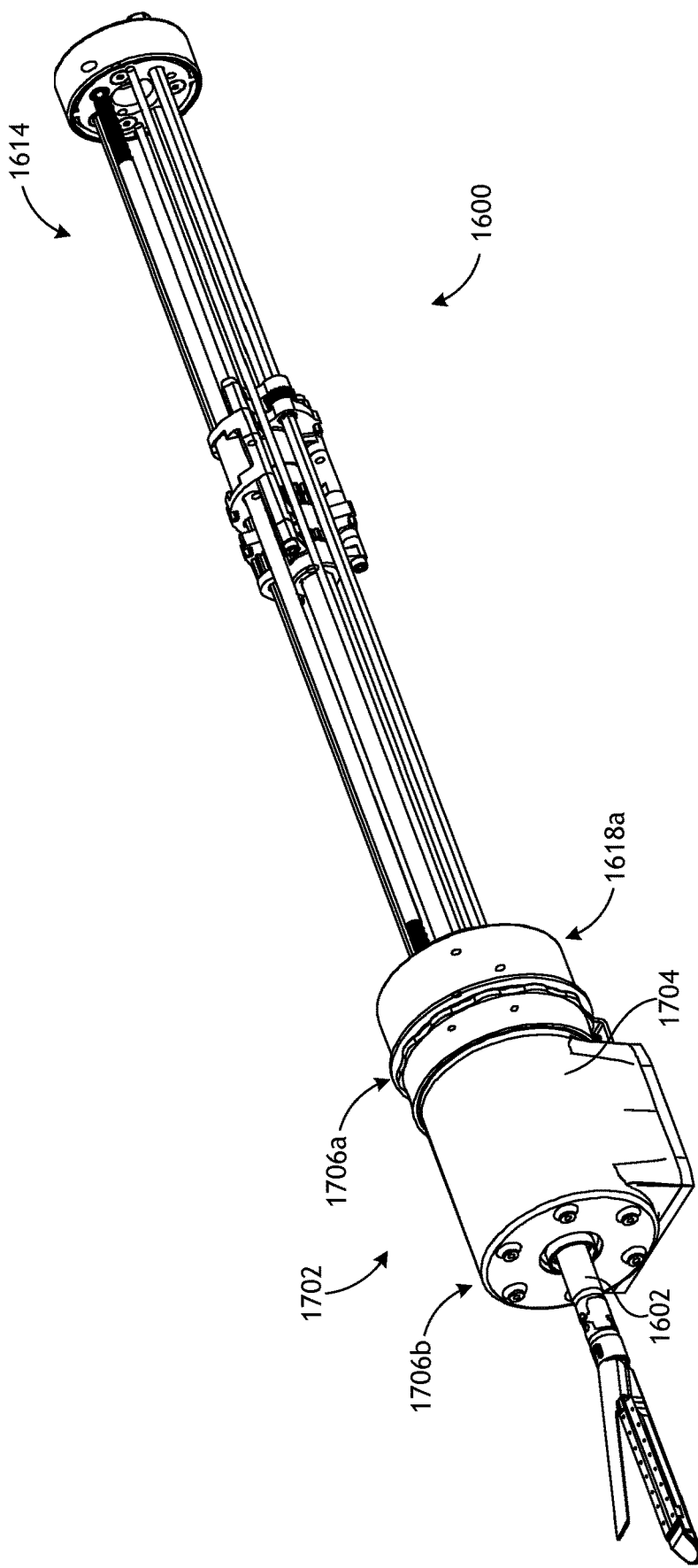
FIG. 17A is an isometric view of the surgical tool of FIG. 16 releasably coupled to an example instrument driver, according to one or more embodiments.

FIG. 17A is an isometric view of the surgical tool 1600 of FIG. 16 releasably coupled to an example instrument driver 1702, according to one or more embodiments. The instrument driver 1702 may be similar in some respects to the instrument drivers 1102, 1200 of FIGS. 11 and 12, respectively, and therefore may be best understood with reference thereto. Similar to the instrument drivers 1102, 1200, for example, the instrument driver 1702 may be mounted to or otherwise positioned at the end of a robotic arm (not shown) and is designed to provide the motive forces required to operate the surgical tool 1600. Unlike the instrument drivers 1102, 1200, however, the shaft 1602 of the surgical tool 1600 extends through and penetrates the instrument driver 1702.

The instrument driver 1702 has a body 1704 having a first or "proximal" end 1706a and a second or "distal" end 1706b opposite the first end 1706a. In the illustrated embodiment, the first end 1706a of the instrument driver 1702 is matable with and releasably coupled to the first end 1618a of the drive housing 1614, and the shaft 1602 of the surgical tool 1600 extends through the body 1704 and distally from the second end 1706b.

Figure 17B:
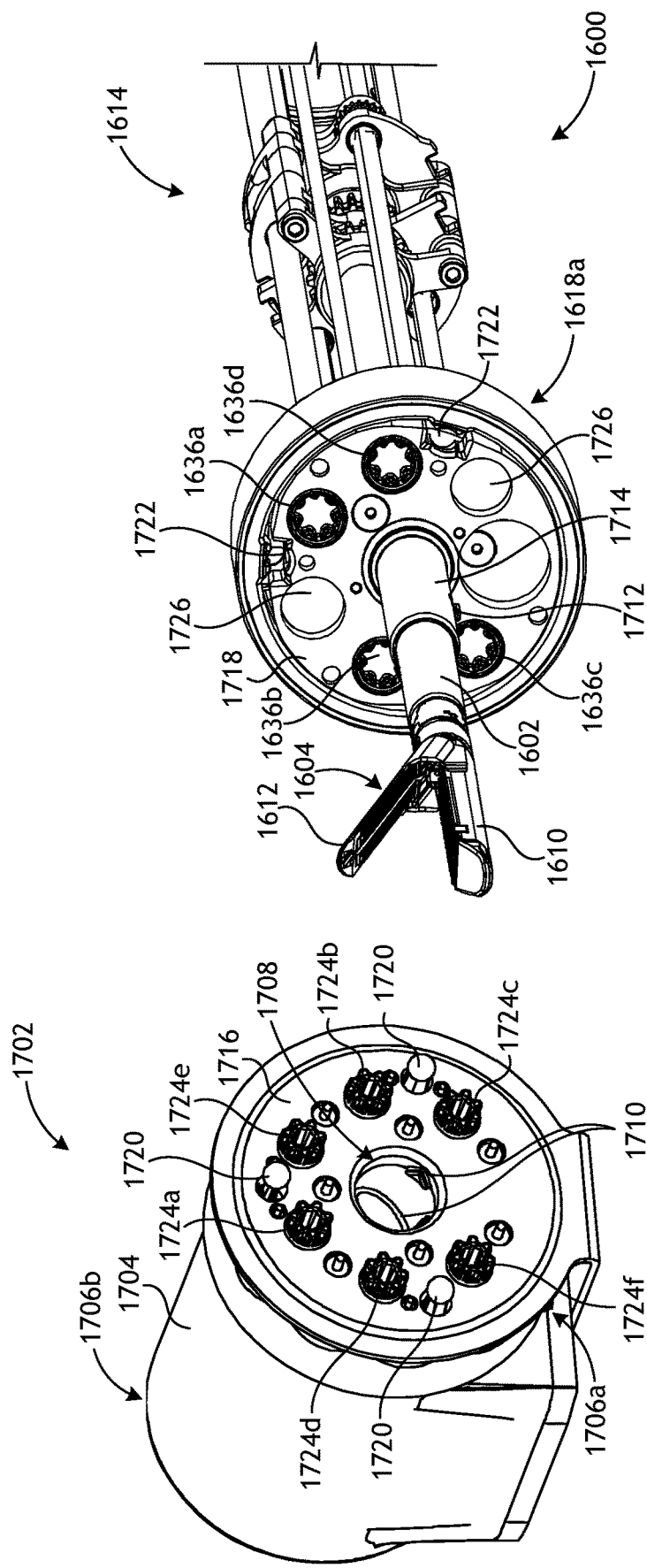
FIG. 17B provides separated isometric end views of the instrument driver and the surgical tool of FIG. 17A.

FIG. 17B depicts separated isometric end views of the instrument driver 1702 and the surgical tool 1600 of FIG. 17A. With the jaws 1610, 1612 closed, the shaft 1602 and the end effector 1604 can penetrate the instrument driver 1702 by extending through a central aperture 1708 defined longitudinally through the body 1704 between the first and second ends 1706a,b. To align the surgical tool 1600 with the instrument driver 1702 in a proper angular orientation, one or more alignment guides 1710 may be provided or otherwise defined within the central aperture 1708 and configured to engage one or more corresponding alignment features 1712 provided on the surgical tool 1600. In the illustrated embodiment, the alignment feature 1712 comprises a protrusion or projection defined on or otherwise provided by an alignment nozzle 1714 extending distally from the first end 1618a of the drive housing 1614. In one or more embodiments, the alignment guide 1710 may comprise a curved or arcuate shoulder or lip configured to receive and guide the alignment feature 1712 as the alignment nozzle 1714 enters the central aperture 1708. As a result, the surgical tool 1600 is oriented to a proper angular alignment with the instrument driver 1702 as the alignment nozzle 1714 is advanced distally through the central aperture 1708. In other embodiments, the alignment nozzle 1714 may be omitted and the alignment feature 1712 may alternatively be provided on the shaft 1602, without departing from the scope of the disclosure.

As illustrated, a drive interface 1716 is provided at the first end 1706a of the instrument driver 1702, and a driven interface 1718 is provided at the first end 1618a of the drive housing 1614. The drive and driven interfaces 1716, 1718 may be configured to mechanically, magnetically, and/or electrically couple the drive housing 1614 to the instrument driver 1702. To accomplish this, the drive and driven interfaces 1716, 1718 may provide one or more matable locating features configured to secure the drive housing 1614 to the instrument driver 1702. In the illustrated embodiment, for example, the drive interface 1716 provides one or more interlocking features 1720 (three shown) configured to locate and mate with one or more complementary-shaped pockets 1722 (two shown, one occluded) provided on the driven interface 1718. In some embodiments, the features 1720 may be configured to align and mate with the pockets 1722 via an interference or snap fit engagement, for example.

The instrument driver 1702 also includes one or more drive outputs that extend through the drive interface 1716 to mate with the drive inputs 1636*a-d* provided at the first end 1618*a* of the drive housing 1614. More specifically, the instrument driver 1702 includes a first drive output 1724*a* matable with the first drive input 1636*a*, a second drive output 1724*b* matable with the second drive input 1636*b*, a third drive output 1724*b* matable with the third drive input 1636*c*, and a fourth drive output 1724*d* matable with the fourth drive input 1636*d*. In some embodiments, as illustrated, the drive outputs 1724*a-d* may define splines or features designed to mate with corresponding splined receptacles of the drive inputs 1636*a-d*. Once properly mated, the drive inputs 1636*a-d* will share axes of rotation with the corresponding drive outputs 1724*a-d* to allow the transfer of rotational torque from the drive outputs 1724*a-d* to the corresponding drive inputs 1636*a-d*. In some embodiments, each drive output 1724*a-d* may be spring loaded and otherwise biased to spring outwards away from the drive interface 1716. Each drive output 1724*a-d* may be capable of partially or fully retracting into the drive interface 1716.

In some embodiments, the instrument driver 1702 may include additional drive outputs, depicted in FIG. 17B as a fifth drive output 1724*e* and a sixth drive output 1724*f*. The fifth and sixth drive outputs 1724*e,f* may be configured to mate with additional drive inputs (not shown) of the drive housing 1614 to help undertake one or more additional functions of the surgical tool 1600. In the illustrated embodiment, however, the drive housing 1614 does not include additional drive inputs matable with the fifth and sixth drive outputs 1724*e,f*. Instead, the driven interface 1718 defines corresponding recesses 1726 configured to receive the fifth and sixth drive outputs 1724*e,f*. In other applications, however, fifth and/or sixth drive inputs (not shown) could be included in the drive housing 1614 to mate with the fifth and sixth drive outputs 1724*e,f*, or the surgical tool 1600 might be replaced with another surgical tool having fifth and/or sixth drive inputs, which would be driven by the fifth and/or sixth drive outputs 1724*e,f*.

While not shown, in some embodiments, an instrument sterile adapter (ISA) may be placed at the interface between the instrument driver 1702 and the surgical tool 1600. In such applications, the interlocking features 1720 may operate as alignment features and possible latches for the ISA to be placed, stabilized, and secured. Stability of the ISA may be accomplished by a nose cone feature provided by the ISA and extending into the central aperture 1708 of the instrument driver 1702. Latching can occur either with the interlocking features 1720 or at other locations at the interface. In some cases, the ISA will provide the means to help align and facilitate the latching of the surgical tool 1600 to the ISA and simultaneously to the instrument driver 1702.

Articulation Mechanisms

Figure 18A:
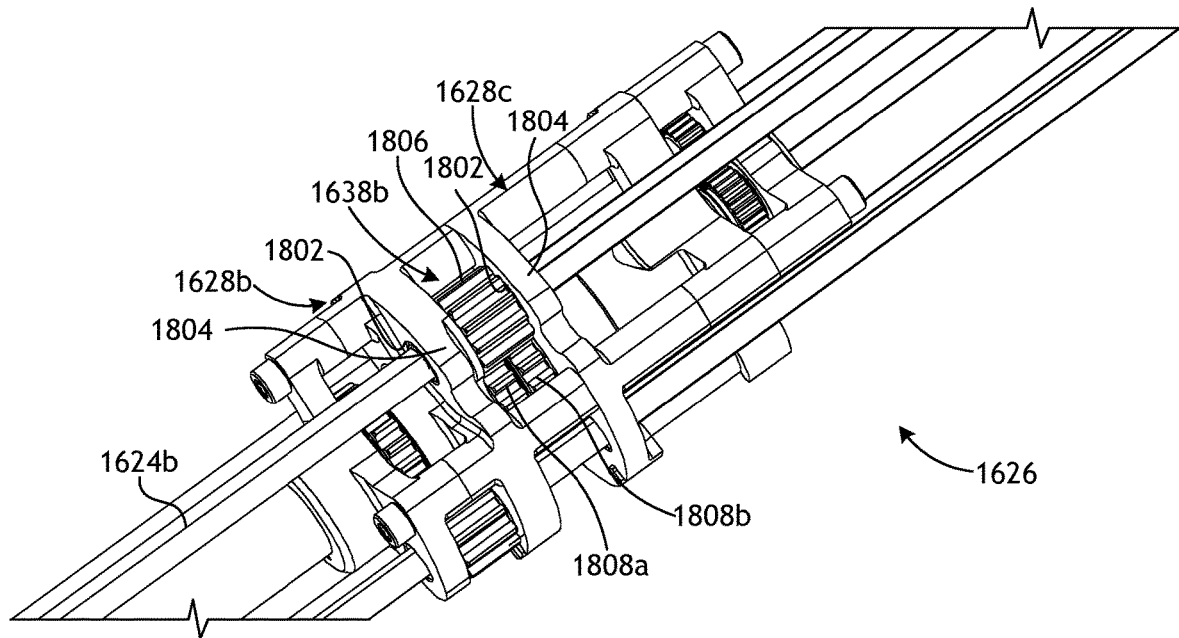
FIGS. 18A and 18B are enlarged isometric and side views, respectively, of the carriage and the second activating mechanism of FIG. 16.

FIG. 18A is an enlarged isometric view of an embodiment of the carriage 1626 and the second activating mechanism 1638*b*. As mentioned above, the second spline 1624*b* can be operatively coupled to the second activating mechanism 1638*b* such that rotating the second spline 1624*b* (via rotation of the third drive input 1636*c* of FIGS. 16 and 17B) will correspondingly actuate the second activating mechanism 1638*b* and thereby cause the wrist 1606 (FIG. 16) to articulate. As illustrated, the second spline 1624*b* extends longitudinally through coaxially aligned apertures 1802 defined in the second and third layers 1628*b,c* of the carriage 1626. In some embodiments, for example, each aperture 1802 may be defined in a corresponding lobe 1804 provided by each of the second and third layers 1628*b,c*.

A drive gear 1806 may be included with the second spline 1624*b* and located between the second and third layers 1628*b,c* and, more particularly, between the lobes 1804 of each layer 1628*b,c*. The second spline 1624*b* may exhibit a cross-sectional shape matable with the drive gear 1806 such that rotation of the second spline 1624*b* correspondingly drives the drive gear 1806 in rotation. In some embodiments, the drive gear 1806 may comprise a separate component part slidably disposed about the second spline 1624*b*. In such embodiments, as the carriage 1626 moves along the longitudinal axis $A_1$ (FIG. 16), the drive gear 1806 will move along the length of the second spline 1624*b* as captured between the second and third layers 1628*b,c*. In other embodiments, however, the second spline 1624*b* may be shaped and otherwise configured to operate as the drive gear 1806 to advantageously reduce the number of component parts.

The drive gear 1806 may be positioned on the carriage 1626 to simultaneously intermesh with a first or "distal" transfer gear 1808*a* and a second or "proximal" transfer gear 1808*b*. Accordingly, as the spline 1624*b* is rotated, the drive gear 1806 drives the first and second transfer gears 1808*a,b* simultaneously.

Figure 18B:
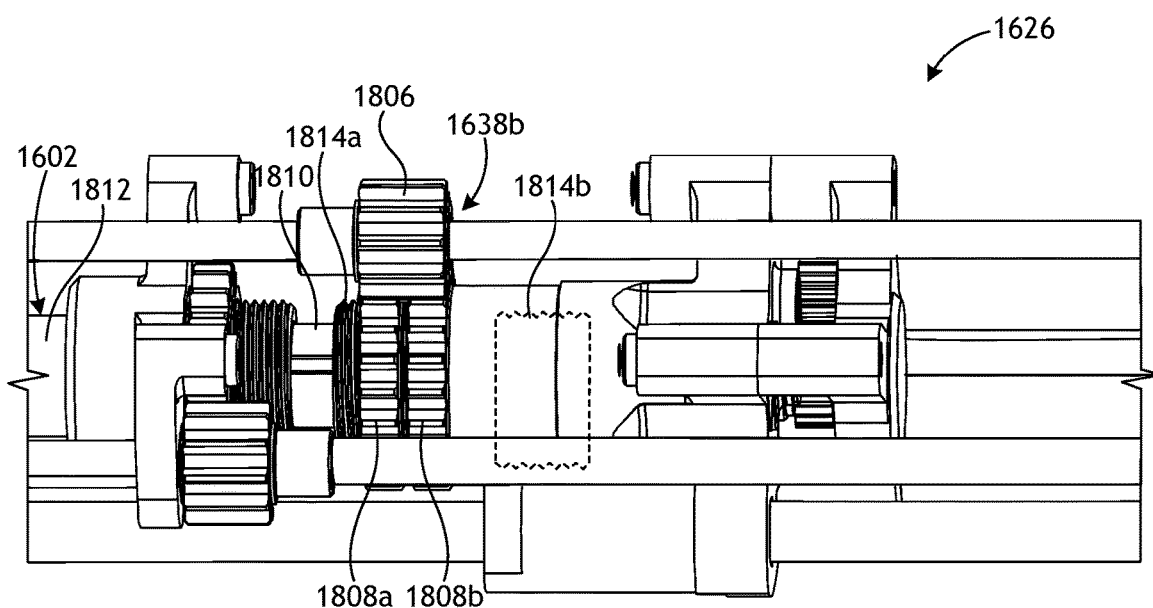

FIG. 18B is an enlarged side view of the carriage 1626 and the second activating mechanism 1638*b*. The second and third layers 1626*b,c* (FIG. 18A) of the carriage 1626 are omitted in FIG. 18B to enable a more full view of the second activating mechanism 1638*b*. The first and second transfer gears 1808*a,b* may comprise annular structures that extend about the shaft 1602 and, more particularly, about an inner grounding member or shaft 1810 that forms part of the shaft 1602. The inner grounding shaft 1810 extends concentrically within an outer portion of the shaft 1602, referred to herein as a closure tube 1812.

The second activating mechanism 1638*b* may further include a first or "distal" carrier 1814*a* (partially visible) and a second or "proximal" carrier 1814*b* (shown in dashed lines). The first carrier 1814*a* radially interposes the inner grounding shaft 1810 and at least a portion of the first transfer gear 1808*a*, and the second carrier 1814*b* radially interposes the inner grounding shaft 1810 and at least a portion of the second transfer gear 1808*b*. The first and second transfer gears 1808*a,b* are internally threaded in opposite directions (i.e., one left-handed and the other right-handed), and the first transfer gear 1808*a* may threadably engage external threads defined by the first carrier 1814*a* while the second transfer gear 1808*b* may threadably engage external threads defined by the second carrier 1814*b*.

Figure 18C:
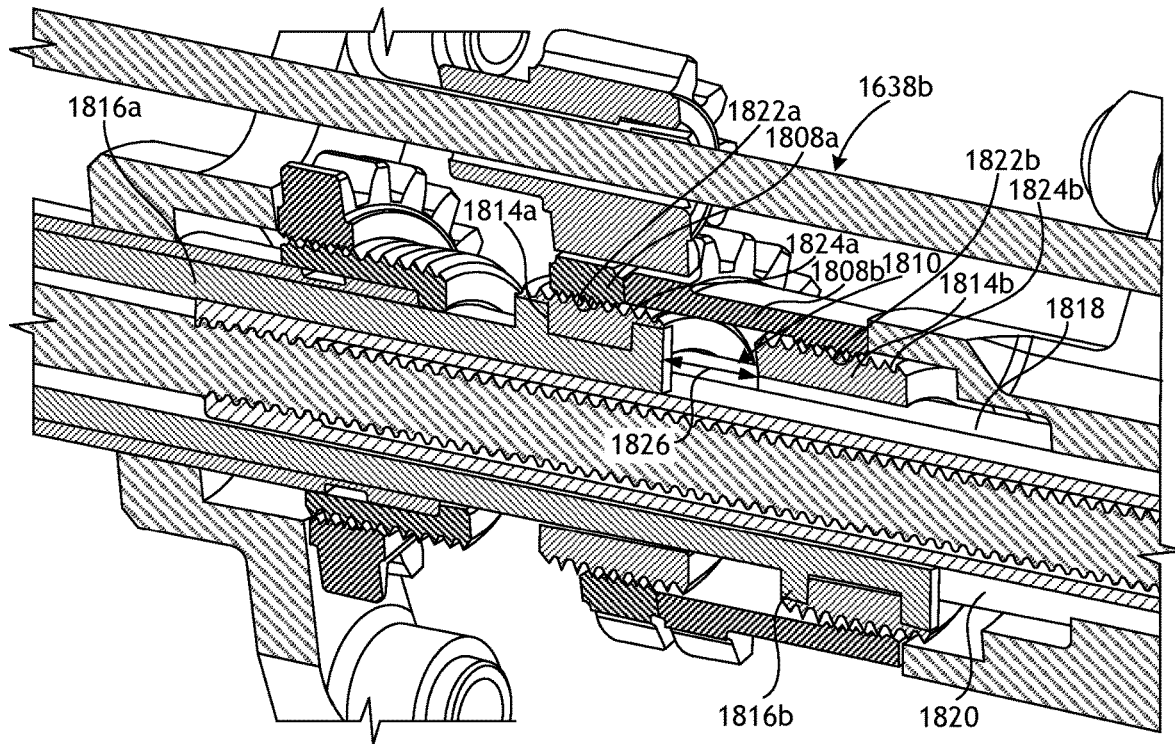
FIG. 18C is an isometric, cross-sectional side view of the second activating mechanism of FIG. 16, according to one or more embodiments.

FIG. 18C is an isometric, cross-sectional side view of the second activating mechanism 1638*b*, according to one or more embodiments. As illustrated, the first and second carriers 1814*a,b* radially interpose the inner grounding shaft 1810 and the first and second transfer gears 1808*a,b*, respectively, as mentioned above. Moreover, the first carrier 1814*a* may be operatively coupled to or otherwise mate with a first drive member 1816a, which extends distally to the wrist 1606 (FIG. 16). As illustrated, the first drive member 1816a is arranged within a corresponding slot 1818 defined in the inner grounding shaft 1810, which guides the first drive member 1816a as it extends to the wrist 1606. Similarly, the second carrier 1814b may be operatively coupled to or otherwise mate with a second drive member 1816b, which extends distally to the wrist 1606. The second drive member 1816b is also arranged within a corresponding slot 1820 defined in the inner grounding shaft 1810, which guides the second drive member 1816b as it extends to the wrist 1606.

The first transfer gear 1808a defines internal threading 1822a matable with external threading 1824a defined on the outer surface of the first carrier 1814a, and the second transfer gear 1808b similarly defines internal threading 1822b matable with external threading 1824b defined on the outer surface of the second carrier 1814b. The internal threadings 1822a,b are oppositely threaded; i.e., one comprises left-handed threads and the other comprises right-handed threads. Consequently, as the drive gear 1806 rotates, it simultaneously drives both transfer gears 1808a,b in rotation, which, in turn, simultaneously drives the corresponding carriers 1814a,b in equal but opposite axial directions because of the oppositely threaded engagement of the internal threadings 1822a,b. Depending on the rotation direction of the drive gear 1806, the carriers 1814a,b may be drawn axially toward each other or moved axially away from each other.

Opposite axial movement of the first and second carriers 1814a,b relative to the inner grounding shaft 1810 and along the longitudinal axis $A_1$ (FIG. 16) correspondingly moves the drive members 1816a,b in the same opposite axial directions and, thereby, articulates the end effector 1604 (FIGS. 16 and 17B). In at least one embodiment, the first and second carriers 1814a,b antagonistically operate such that one of the carriers 1814a,b pulls one of the drive members 1816a,b proximally while the other carrier 1814a,b simultaneously pushes the other drive member 1816a,b distally. A gap 1826 provided between the carriers 1814a,b along the inner grounding shaft 1810 allows the carriers 1814a,b to move toward and away from one another, and thereby provides clearance to facilitate clockwise and counter-clockwise articulation. As the carriers 1814a,b are drawn axially toward each other, the end effector 1604 will articulate in a first direction, and as the carriers 1814a,b are moved axially away from each other, the end effector 1604 will articulate in a second direction opposite the first direction.

Figure 19:
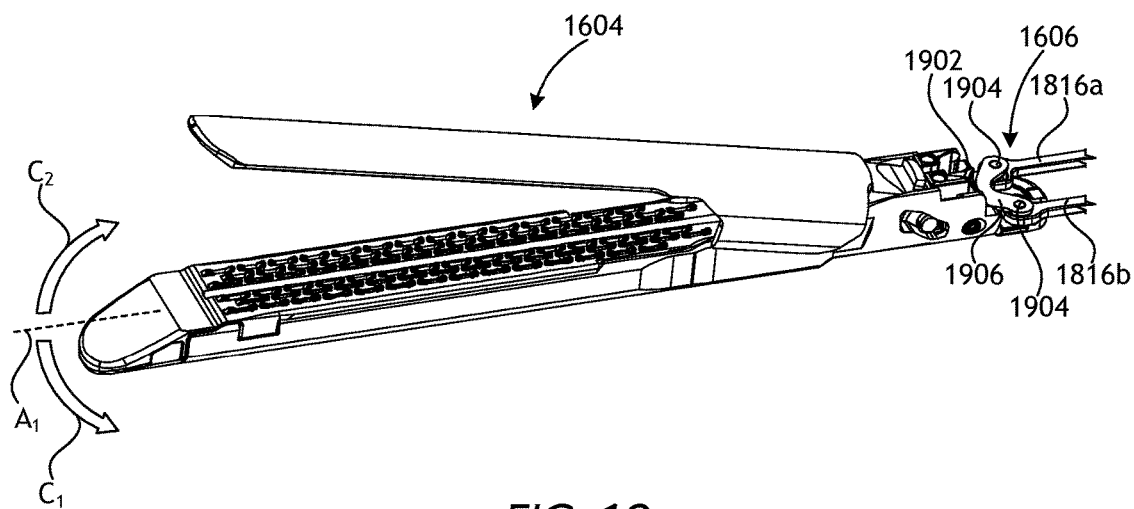
FIG. 19 is an enlarged view of the end effector of FIG. 16 and an exposed view of the wrist of FIG. 16, according to one or more embodiments.

Referring to FIG. 19, with continued reference to FIG. 18C, depicted is an enlarged view of the end effector 1604 and an exposed view of the wrist 1606, according to one or more embodiments. In FIG. 19, the inner grounding shaft 1810 (FIGS. 18B-18C) has been removed to enable viewing of how the drive members 1816a,b interconnect with or are otherwise operatively connected to the end effector 1604. In the illustrated embodiment, the end effector 1604 is mounted to an end effector mount 1902 that defines or otherwise provides two articulation pins 1904, and the distal end of each drive member 1816a,b is rotatably mounted to a corresponding one of the articulation pins 1904. The drive members 1816a,b are also interconnected at the distal ends via a distal link 1906, which together comprise a linkage configured to help articulate end effector mount 1902, and therefore the end effector 1604, in a plane parallel to the longitudinal axis $A_1$.

In this configuration, the drive members 1816a,b translate antagonistically and parallel along the longitudinal axis $A_1$, such that as the first drive member 1816a moves distally the second drive member 1816b moves proximally, and vice versa. Moreover, distal movement of the first drive member 1816a and simultaneous proximal movement of the second drive member 1816b cooperatively act on the end effector mount 1902 to cause the end effector 1604 to rotate counterclockwise, as indicated by the arrow $C_1$. In contrast, proximal movement of the first drive member 1816a and simultaneous distal movement of the second drive member 1816b cooperatively act on the end effector mount 1902 to cause the end effector 1604 to rotate clockwise, as indicated by the arrow $C_2$.

Figure 20:
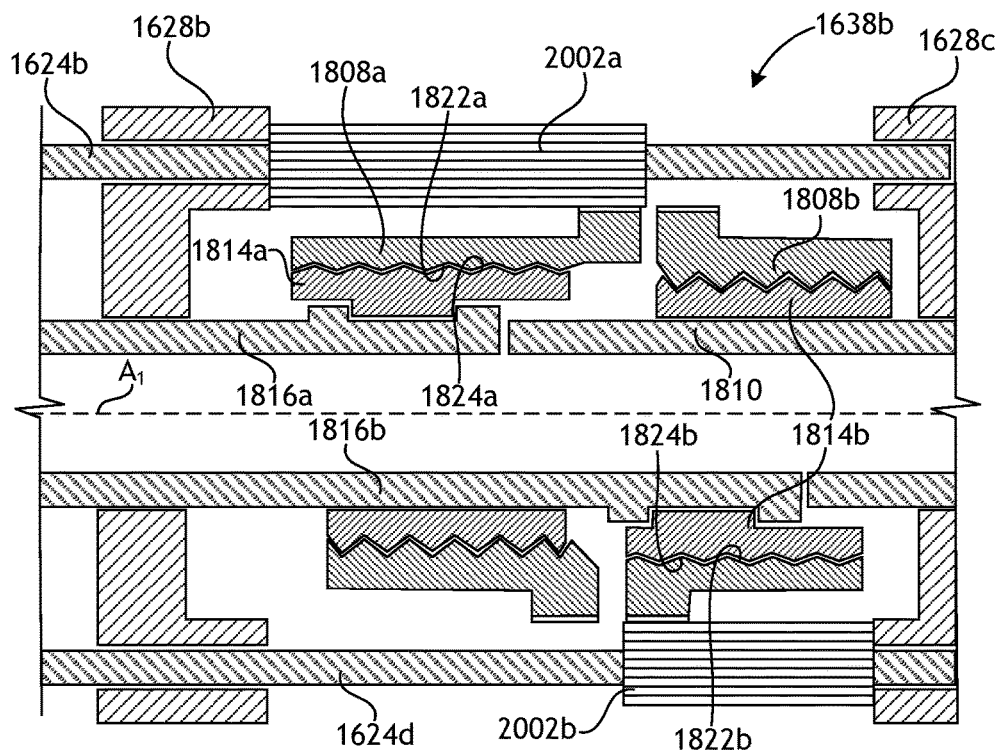
FIG. 20 is an enlarged cross-sectional side view of another embodiment of the second activating mechanism of FIGS. 18A-18C.

FIG. 20 is an enlarged cross-sectional side view of another embodiment of the second activating mechanism 1638b. The embodiment shown in FIG. 20 is similar in some respects to the embodiment of the second activating mechanism 1638b of FIGS. 18A-18C and, therefore, may be best understood with reference thereto. Similar to the embodiment of FIGS. 18A-18C, for example, the second activating mechanism 1638b of FIG. 20 includes the first and second carriers 1814a,b radially interposing the inner grounding shaft 1810 and the first and second transfer gears 1808a,b, respectively. Moreover, the first carrier 1814a is operatively coupled to or otherwise mates with the first drive member 1816a, and the second carrier 1814b operatively couples to or otherwise mates with the second drive member 1816b, and the drive members 1816a,b extend distally to the wrist 1606 (FIGS. 16 and 19). The internal threading 1822a of the first transfer gear 1808a mates with the external threading 1824a of the first carrier 1814a, and the internal threading 1822b of the second transfer gear 1808b similarly mates with the external threading 1824b of the second carrier 1814b, and the internal threadings 1822a,b are again oppositely threaded.

Unlike the embodiment of the second activating mechanism 1638b of FIGS. 18A-18C, however, the embodiment of FIG. 20 includes two splines and two corresponding drive gears. More specifically, a first drive gear 2002a may be included with the second spline 1624b such that rotation of the second spline 1624b correspondingly rotates the first drive gear 2002a, and a second drive gear 2002b may be included with a fourth spline 1624d such that rotation of the fourth spline 1624d correspondingly rotates the second drive gear 2002b. As mentioned above, the third drive output 1724b (FIG. 17B) may drive the third drive input 1636c (FIGS. 16 and 17B) to rotate the second spline 1624b. In one or more embodiments, the fourth spline 1624d may be operatively coupled to a fifth drive input (not shown) at the first end 1618a of the drive housing 1614 (FIGS. 16 and 17B) and driven by one of the fifth or sixth drive outputs 1724e,f (FIG. 17B). In such embodiments, actuation of the fifth or sixth drive output 1724e,f will correspondingly cause the fourth spline 1624d to rotate and thereby rotate the second drive gear 2002b.

Both drive gears 2002a,b may be located between the second and third layers 1628b,c. The first drive gear 2002a may be positioned to intermesh with the first transfer gear 1808a, and the second drive gear 2002b may be positioned to intermesh with the second transfer gear 1808b. As the first drive gear 2002a rotates, the first transfer gear 1808a is correspondingly rotated and drives the first carrier 1814a axially along the longitudinal axis $A_1$ because of the threaded engagement of the intermeshed internal and external threadings 1822a, 1824a. Similarly, as the second drive gear 2002b rotates, the second transfer gear 1808b correspondingly rotates and drives the second carrier 1814b axially along the longitudinal axis $A_1$ because of the threaded engagement of the intermeshed internal and external threadings 1822b, 1824b. Depending on the rotation direction of the drive gears 2002a,b, the carriers 1814a,b may be moved axially toward or away from each other.

Axial movement of the first and second carriers 1814a,b along the longitudinal axis $A_1$ cooperatively actuates the drive members 1816a,b, and thereby articulates the end effector 1604 (FIGS. 16 and 19). In at least one embodiment, the first and second carriers 1814a,b protagonistically operate such that one of the carriers 1814a,b pulls one of the drive members 1816a,b proximally while the other carrier 1814a,b pushes the other drive member 1816a,b distally. In some embodiments, however, the first and second carriers 1814a,b may be operated independently without the other being operated (affected), thus operating antagonistically where one reduces the force effect of the other. In antagonistic operation, one of the carriers 1814a,b pulls (or pushes) the drive member 1816a,b associated therewith proximally (or distally) with a first force while the other one of the carriers 1814a,b pulls (or pushes) the drive member 1816a,b associated therewith proximally (or distally) with a second force, where the first force is larger than the second force such that the first force can overcome the second force, as well as the internal losses of the device (i.e., friction) and loads imparted on the end effector 1604 via the external environment. As will be appreciated, this ensures that the carrier 1814a,b providing the first force moves proximally (or distally) while the carrier 1815a,b providing the second force moves distally (or proximally).

Software stored on a computer system may be configured to control the drive outputs 1724b and 1724e or 1724f (FIG. 17B) that drive rotation of the second and fourth splines 1624b,d, respectively, to thereby synchronize actuation (movement) of the carriers 1814a,b and the corresponding drive members 1816a,b. In some embodiments, the software may further be configured to reduce lag or slop (slack) in movement of the carriers 1814a,b, which correspondingly reduces lag or slop (slack) in articulation of the end effector 1604. In the embodiment of FIG. 20, for example, one drive output 1724b or 1724e,f may turn counter-clockwise while the other drive output 1724b or 1724e,f compensates by turning clockwise. Moreover, one drive output 1724b or 1724e,f may lag or precede the other, depending on the mechanism lag or slop. Accordingly, such control algorithms may be used to compensate, reduce lag, and reduce slack for one or more of the drive inputs 1636a-d (FIGS. 16 and 17B).

Referring again to FIG. 19, with continued reference to FIG. 20, to articulate the end effector 1604 clockwise $C_2$, the first drive member 1816a is moved proximally and the second drive member 1816b is moved distally. In such operation, the first drive member 1816a may be moved proximally a greater distance than the second drive member 1816b is moved distally, which allows the second drive member 1816b to maintain pull tension as it travels less than the first drive member 1816a, which helps reduce lag and/or slop. To articulate the end effector 1604 counter clockwise $C_1$, the second drive member 1816b is moved proximally and the first drive member 1816a is moved distally. In such operation, the second drive member 1816b is moved proximally a greater distance than the first drive member 1816a is moved distally, which allows the first drive member 1816a to maintain pull tension as it travels less than the second drive member 1816b, which also helps reduce lag and/or slop.

Figure 21A:
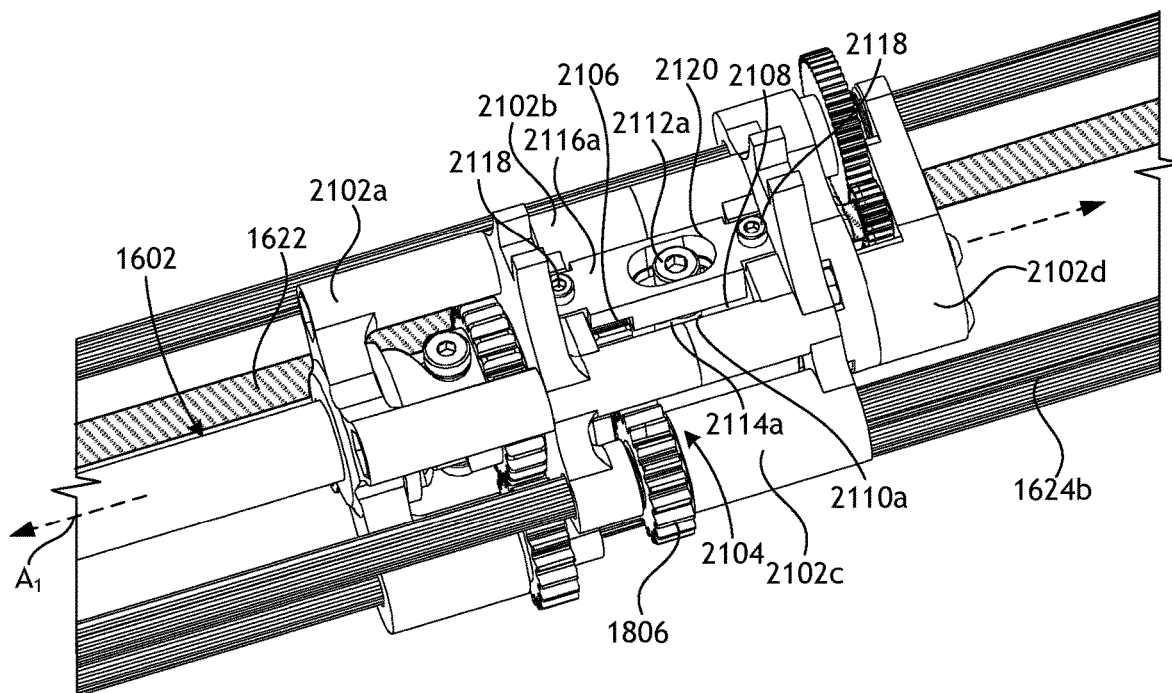
FIGS. 21A and 21B are enlarged isometric top and bottom views, respectively, of an example carriage, according to one or more embodiments.
Figure 21B:
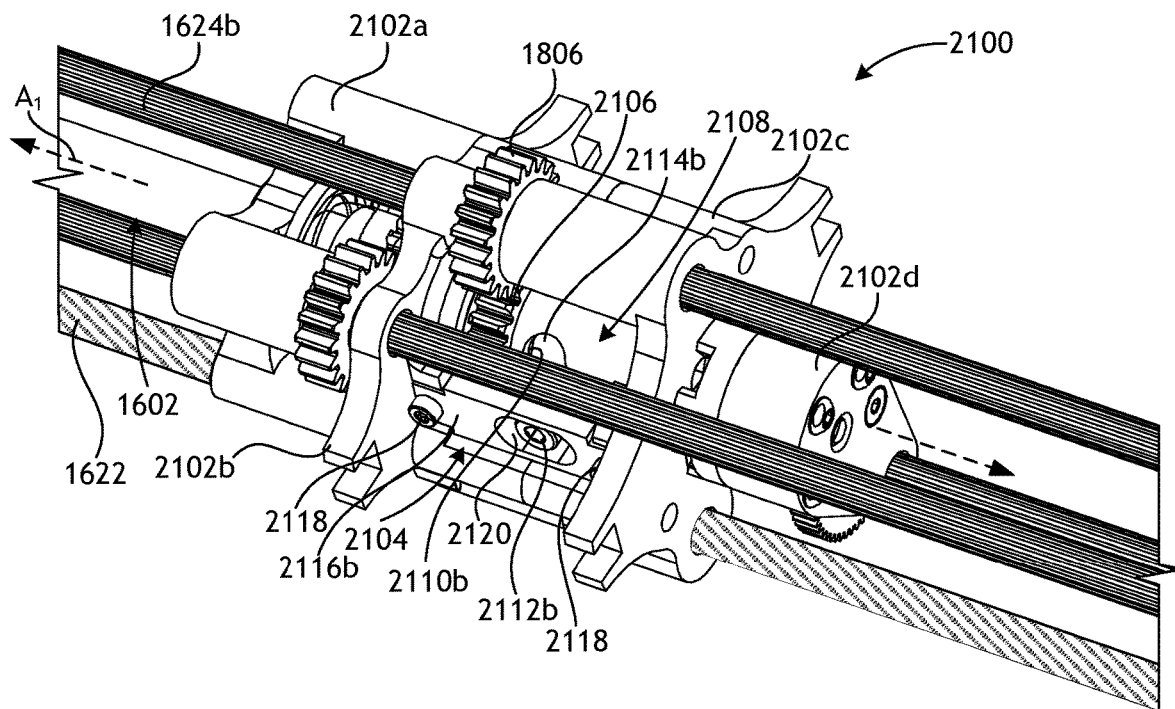

FIGS. 21A and 21B are enlarged isometric top and bottom views, respectively, of an example carriage 2100, according to one or more embodiments. The carriage 2100 may be similar in some respects to the carriage 1626 of FIGS. 16 and 18A-18C and therefore may be best understood with reference thereto. In some applications, the carriage 2100 may replace the carriage 1626 in the drive housing 1614 of FIG. 16. As illustrated, the carriage may comprise two or more layers, shown in FIGS. 21A-21B as a first layer 2102a, a second layer 2102b, a third layer 2102c, and a fourth layer 2102d. While four layers 2102a-e are depicted, more or less than four may be included in the carriage 2100, without departing from the scope of the disclosure. The shaft 1602 is coupled to and extends distally from the carriage 2100, and the carriage 2100 is able to translate along the longitudinal axis $A_1$ by moving up and down (traversing) the lead screw 1622, as generally described above with reference to FIG. 16. As the carriage 2100 moves along the longitudinal axis $A_1$, the end effector 1604 (FIG. 16) correspondingly advances or retracts.

In the illustrated embodiment, the carriage 2100 includes an activating mechanism 2104 operable to articulate the end effector 1604 at the wrist 1606 (FIGS. 16 and 19). The activating mechanism 2104 may be similar in some respects to the second activating mechanism 1638b (FIGS. 16 and 18A-18C) and may be actuated through rotation of the second spline 1624b. In the illustrated embodiment, the second spline 1624b is operatively coupled to the activating mechanism 2104 such that rotating the second spline 1624b (e.g., via rotation of the third drive input 1636c of FIGS. 16 and 17B) correspondingly actuates the activating mechanism 2104 and thereby causes the wrist 1606 to articulate. More specifically, the drive gear 1806 is included with the second spline 1624b and positioned to intermesh with a driven gear 2106 coupled to or otherwise forming part of an articulation barrel 2108. As the spline 1624b is rotated, the drive gear 1806 drives the driven gear 2106 and correspondingly rotates the articulation barrel 2108 about the longitudinal axis $A_1$.

The articulation barrel 2108 defines or otherwise provides one or more cam slots or profiles, partially shown in FIGS. 21A-21B as a first cam profile 2110a (FIG. 21A) and a second cam profile 2110b (FIG. 21B). The activating mechanism 2104 further includes a first follower pin 2112a (FIG. 21A) and a second follower pin 2112b (FIG. 21B). The first follower pin 2112a extends through the first cam profile 2110a and is coupled to a first carrier 2114a (FIG. 21A), and the second follower pin 2112b extends through the second cam profile 2110b and is coupled to a second carrier 2114b (FIG. 21B). Each cam profile 2110a,b extends about the circumference of the articulation barrel 2108 (e.g., in a helical pattern), but the profiles are defined at opposite angles.

As the drive gear 1806 drives the driven gear 2106, the articulation barrel 2108 correspondingly rotates about the longitudinal axis $A_1$, thus urging the follower pins 2112a,b to traverse the oppositely-angled cam profiles 2110a,b, respectively. As the follower pins 2112a,b traverse the cam profiles 2110a,b, the underlying carriers 2114a,b are urged in equal but opposite axial directions along the longitudinal axis $A_1$. Depending on the rotation direction of the drive gear 1806, the carriers 1814a,b may be drawn axially toward each other or moved axially away from each other.

In some embodiments, as illustrated, the activating mechanism 2104 may further include a first articulation torque bar 2116a (FIG. 21A) and a second articulation torque bar 2116b (FIG. 21B). The articulation torque bars 2116a,b may be secured to the carriage 2100 using one or more mechanical fasteners 2118 (e.g., screws, bolts, etc.). In the illustrated embodiment, the articulation bars 2116a,b extend between the second and third layers 2102b,c and may be secured to each layer 2102b,c at each end. Each torque articulation bar 2116a,b may define a slot 2120 sized to receive the head of the corresponding follower pin 2112a,b. During actuation/operation of the activating mechanism 2104, the articulation torque bars 2116a,b may help maintain an axial position of the corresponding follower pin 2112a,b. More specifically, as the articulation barrel 2108 rotates, the follower pins 2112a,b will have a tendency to also rotate as they traverse the corresponding cam profiles 2110a,b. Receiving the head of each follower pin 2112a,b within the slots 2120 of each stationary articulation torque bar 2116a,b will help prevent the follower pins 2112a,b from rotating but instead maintain their axial position.

Figure 22A:
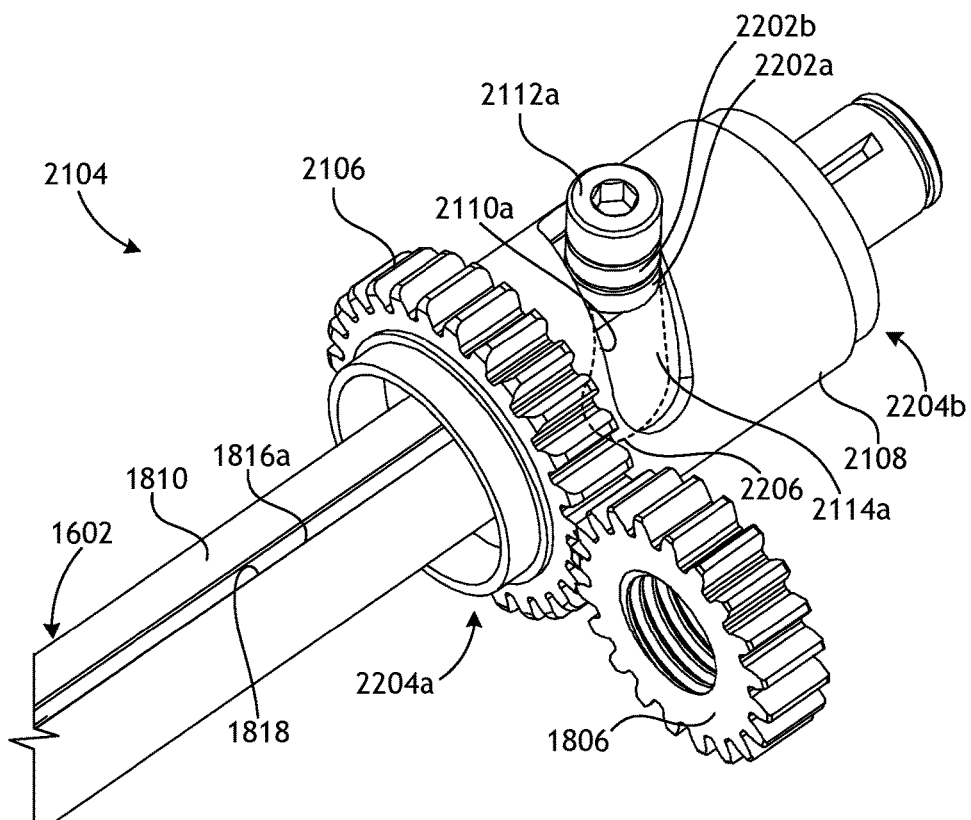
FIGS. 22A and 22B are isometric top and bottom views, respectively, of a portion of the activation mechanism of FIGS. 21A-21B, according to one or more embodiments.
Figure 22B:
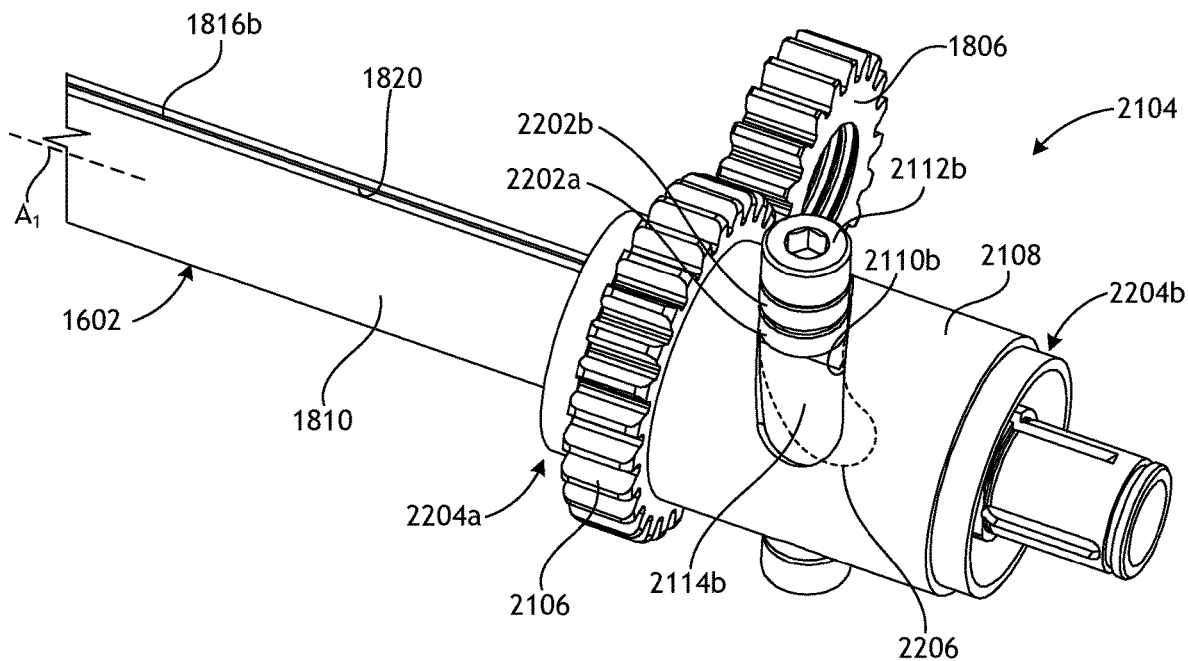

FIGS. 22A and 22B are isometric top and bottom views, respectively, of a portion of the activation mechanism 2104, according to one or more embodiments. Many component parts of the carriage 2100 are omitted in FIGS. 22A-22B to enable a fuller view of various parts of the activation mechanism 2104. As illustrated, the articulation barrel 2108 may comprise a generally cylindrical structure that extends about the shaft 1602 and, more particularly, about the inner grounding shaft 1810. The first and second carriers 2114a,b interpose the inner grounding shaft 1810 and the articulation barrel 2108 and are independently movable along the longitudinal axis $A_1$. The first carrier 2114a may be operatively coupled to the first drive member 1816a (FIG. 22A), which extends distally to the wrist 1606 (FIG. 16) at least partially within the slot 1818 defined in the inner grounding shaft 1810. Moreover, the second carrier 2114b may be operatively coupled to the second drive member 1816b (FIG. 22B), which extends distally to the wrist 1606 at least partially within the slot 1820 defined in the inner grounding shaft 1810.

The follower pins 2112a,b extend through the corresponding cam profiles 2110a,b and are coupled to the associated carriers 2114a,b, respectively. In some embodiments, one or both of the follower pins 2112a,b may be made of or coated with a lubricious material configured to bear against the inner walls of the cam profiles 2110a,b as the articulation barrel 2108 rotates, thus reducing friction. In other embodiments, however, and as illustrated, one or both of the follower pins 2112a,b may including one or more bearings, shown as a first bearing 2202a and a second bearing 2202b. In the illustrated embodiment, the first and second bearings 2202a,b are stacked on top of each other and the shaft of each follower pin 2112a,b extends through the first and second bearings 2202a,b. The first bearings 2202a may be configured to bear against the inner walls of the cam profiles 2110a,b as the articulation barrel 2108 rotates and the follower pins 2112a,b are urged to traverse the cam profiles 2110a,b, respectively, thus reducing friction. The second bearings 2202b may be configured to bear against the inner walls of the slot 2120 (FIGS. 21A-21B) defined in the corresponding torque articulation bar 2116a,b (FIGS. 21A-21B) to prevent rotational movement of the follower pins 2112a,b as the articulation barrel 2108 rotates.

The articulation barrel 2108 has a first end 2204a and a second end 2204b, and the driven gear 2106 may be defined or otherwise provided at or near the first end 2204a, but could alternatively be provided at or near the second end 2204b or at any other another location between the first and second ends 2204a,b. While actuating the activation mechanism 2104, the drive gear 1806 drives the driven gear 2106 and thereby rotates the articulation barrel 2108 about the longitudinal axis $A_1$. As the articulation barrel 2108 rotates, the follower pins 2112a,b are urged to traverse the cam profiles 2110a,b, respectively, and the interconnected carriers 2114a,b are correspondingly urged in equal but opposite axial directions along the longitudinal axis $A_1$. As the carriers 2114a,b move axially, the interconnected drive members 1816a,b simultaneously move in the same direction and thereby cause the end effector 1604 (FIGS. 16 and 19) to articulate, as described above.

In some embodiments, the cam profiles 2110a,b may comprise straight slots extending at a constant angle about the circumference of the articulation barrel 2108, but at opposite angular directions. If the first cam profile 2110a extends at a positive angle relative to the longitudinal axis $A_1$ (e.g., 15° or 75°), for example, then the second cam profile 2110b would extend at an equal but opposite negative angle relative to the longitudinal axis $A_1$ (e.g., −15° or −75°). In embodiments where the cam profiles 2110a,b are straight, the movement and force applied to the carriers 2114a,b and drive members 1816a,b will be constant during articulation of the end effector 1604 (FIGS. 16 and 19). In such embodiments, the cam profiles 2110a,b may be characterized as helical cam slots and the follower pins 2112a,b may be characterized as linear cam followers.

In other embodiments, however, one or both of the cam profiles 2110a,b may not be entirely straight but may alternatively diverge at one or more inflection points along the length (path) of the cam profile 2110a,b. More specifically, the cam profiles 2110a,b may diverge from straight and define a more or less aggressive path 2206 (shown in dashed lines), depending on the direction at the inflection point. Higher or lower angles of the cam profiles 2110a,b will alter the mechanical advantage obtained as the follower pins 2112a,b traverse the cam profiles 2110a,b and act on the interconnected carriers 2114a,b, respectively. This may also prove advantageous in making the system easier to back-drive and put the end effector 1604 (FIGS. 16 and 19) back in line with the longitudinal axis $A_1$ in the event of a power failure.

In some embodiments, the ends of the cam profiles 2110a,b may be characterized or otherwise operate as physical stops detectable by various input torque sensors associated with the instrument driver 1702 (FIGS. 17A-17B). In other embodiments, the ends of the cam profiles 2110a,b may be position controlled, which would provide extra travel distance to compensate for tolerances, and thus minimize mechanism damage if over shot slightly (e.g., no build up of loads).

Figure 23:
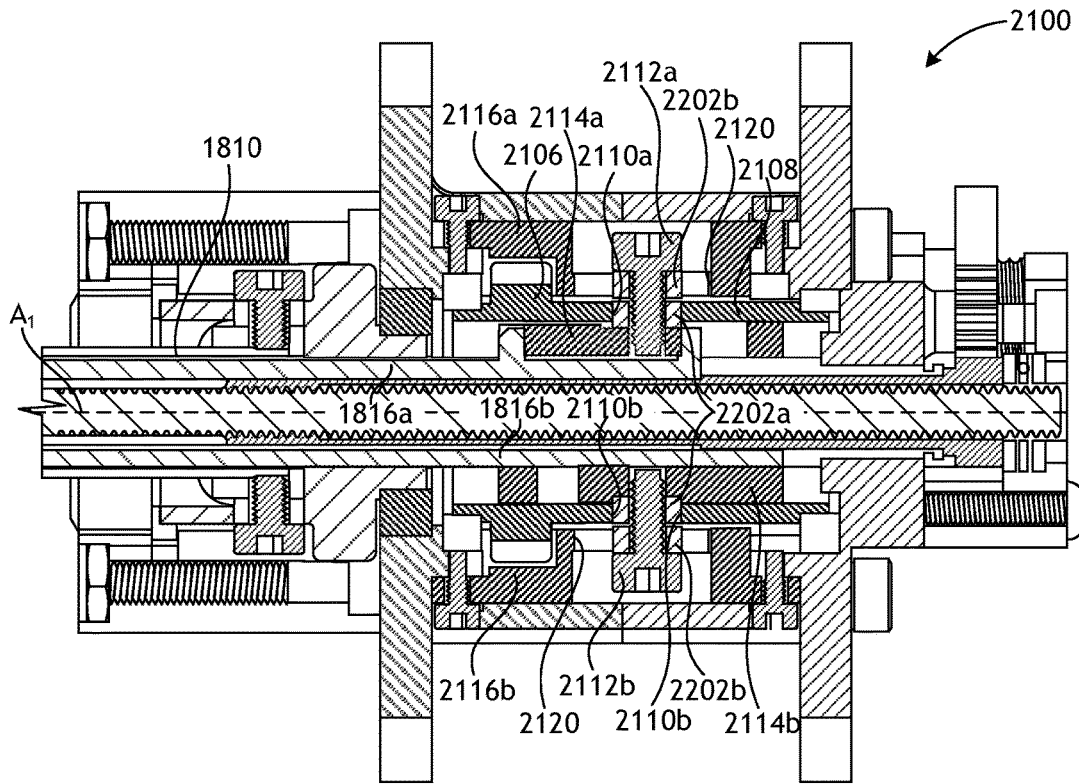
FIG. 23 is a cross-sectional side view of the carriage of FIGS. 21A-21B.

FIG. 23 is a cross-sectional side view of the carriage 2100. As illustrated, the first and second carriers 2114a,b radially interpose the inner grounding shaft 1810 and the articulation barrel 2108, as mentioned above. Moreover, the first carrier 2114a is operatively coupled to or otherwise mated with the first drive member 1816a, and the second carrier 2114b is operatively coupled to or otherwise mated with the second drive member 1816b. The follower pins 2112a,b extend through the slots 2120 in the articulation torque bars 2116a,b and corresponding cam profiles 2110a,b, respectively, to be coupled to the associated carriers 2114a,b. In some embodiments, the follower pins 2112a,b may be threaded to the corresponding carriers 2114a,b, but may alternatively be secured to the carriers 2114a,b in other ways, such as through an interference (shrink) fit, welding, an adhesive, a snap fit, or any combination thereof. In other embodiments, the follower pins 2112a,b may be merely received within corresponding apertures defined in the carriers 2114a,b, and not necessarily fixed thereto, without departing from the scope of the disclosure.

As illustrated, the first bearings 2202a bear against the inner walls of the corresponding cam profiles 2110a,b, and the second bearings 2202b are able to bear against the inner walls of the slot 2120 defined in the corresponding torque articulation bars 2116a,b. Placing the head of the follower pins 2112a,b in the slots 2120 may help ensure that all of the motion of the interconnected carrier 2114a,b is linear instead of rotational as the follower pins 2112a,b traverse the cam profiles 2110a,b, respectively. Consequently, to negate lateral twisting of the follower pins 2112a,b, the follower pins 2112a,b are received within the slots 2120, which restrict rotational movement of the follower pins 2112a,b.

While actuating the activation mechanism 2104, the drive gear 1806 (FIGS. 21A-21B, 22A-22B) drives the driven gear 2106 and thereby rotates the articulation barrel 2108 about the longitudinal axis $A_1$. As the articulation barrel 2108 rotates, the follower pins 2112a,b are urged to traverse the cam profiles 2110a,b, respectively, and the corresponding carriers 2114a,b are urged in equal but opposite axial directions along the longitudinal axis $A_1$ because of the oppositely angled cam profiles 2110a,b. Depending on the rotation direction of the drive gear 1806, the carriers 2114a,b may be drawn axially toward each other or moved axially away from each other.

Opposite axial movement of the first and second carriers 2114a,b relative to the inner grounding shaft 1810 correspondingly moves the drive members 1816a,b in the same opposite axial directions and, thereby, articulates the end effector 1604 (FIGS. 16 and 17B). In at least one embodiment, the first and second carriers 2114a,b antagonistically operate such that one of the carriers 2114a,b pulls one of the drive members 1816a,b proximally while the other carrier 2114a,b simultaneously pushes the other drive member 1816a,b distally. As the carriers 2114a,b are drawn axially toward each other, the end effector 1604 will articulate in a first direction, and as the carriers 2114a,b are moved axially away from each other, the end effector 1604 will articulate in a second direction opposite the first direction.

Firing Mechanism on Translating System

Figure 24:
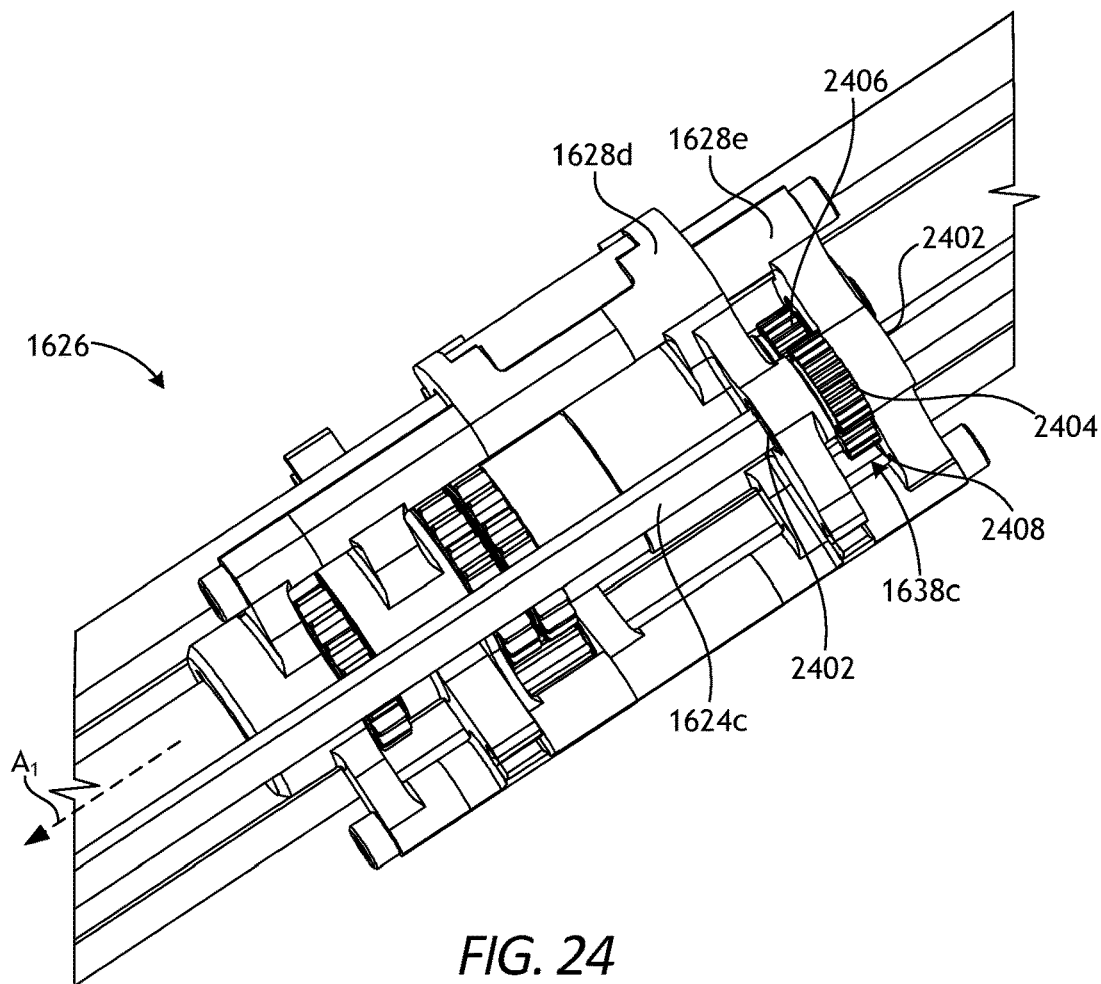
FIG. 24 is another enlarged isometric view of the carriage of FIG. 16.

FIG. 24 is another enlarged isometric view of the carriage 1626 of FIG. 16, and further provides an enlarged view of the third activating mechanism 1638c briefly described above. As mentioned above, the third spline 1624c can be operatively coupled to the third activating mechanism 1638c such that rotating the third spline 1624c (via rotation of the fourth drive input 1636d of FIGS. 16 and 17B) will correspondingly actuate the third activating mechanism 1638c and thereby cause the cutting element (knife) at the end effector 1604 (FIGS. 16, 17B, 19) to "fire". As discussed above, "firing" the end effector 1604 refers to advancing or retracting the cutting element (knife), depending on the rotational direction of the third spline 1624c.

As illustrated, the third spline 1624c extends longitudinally through coaxially aligned apertures 2402 defined in the fourth and fifth layers 1628d,e of the carriage 1626. A drive gear 2404 may be coupled to the third spline 1624c and configured to rotate as the third spline 1624c rotates. As illustrated, the drive gear 2404 may be located between adjacent portions of the fourth and fifth layers 1628d,e. In some embodiments, the drive gear 2404 may comprise a separate component part disposed about the third spline 1624c and capable of translating (sliding) along the third spline 1624c as the carriage 1626 moves along the longitudinal axis $A_1$. In other embodiments, however, the third spline 1624c may be shaped and otherwise configured to operate as the drive gear 2404 to advantageously reduce the number of component parts.

The drive gear 2404 may be configured to drive an input gear 2406 also mounted to the carriage 1626 and forming part of the third activating mechanism 1638c. In some embodiments, the drive gear 2404 may be positioned to directly intermesh with the input gear 2406 and thereby directly drive the input gear 2406 as the third spline 1624c rotates. In other embodiments, however, an idler gear 2408 may interpose the drive gear 2404 and the input gear 2406 and may otherwise transfer torque from the drive gear 2404 to the input gear 2406 via an intermeshed gearing arrangement.

Figure 25:
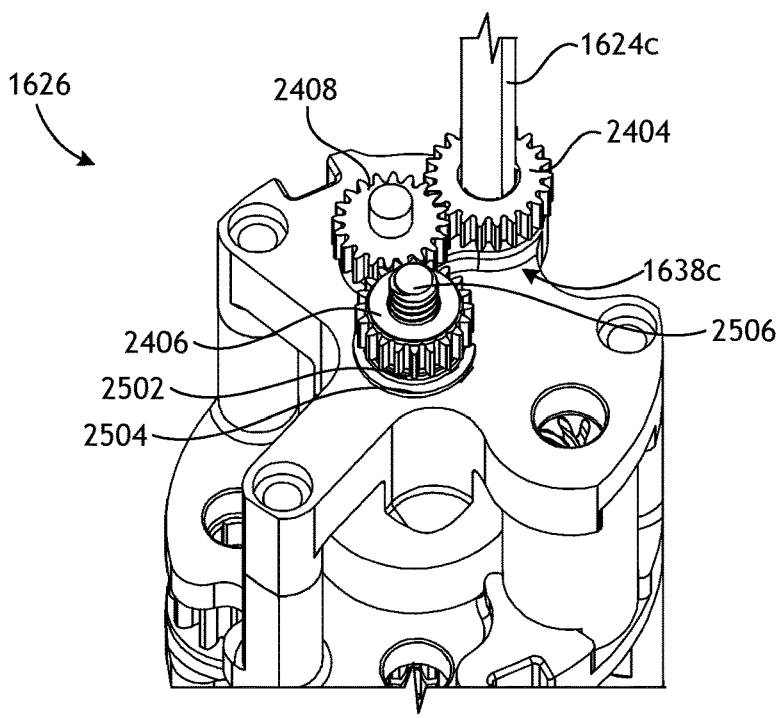
FIG. 25 is an enlarged view of the proximal end of the carriage and the third activating mechanism of FIG. 24.

FIG. 25 is an enlarged view of the proximal end of the carriage 1626 and the third activating mechanism 1638c. Various parts of the carriage 1626 are omitted in FIG. 25, such as the fifth layer 1628e, to enable a fuller view of the third activating mechanism 1638c. As illustrated, the drive gear 2404 is coupled to or forms part of the third spline 1624c and intermeshes with the idler gear 2408, which correspondingly intermeshes with the input gear 2406. In other embodiments, however, the drive gear 2404 may alternatively directly contact and drive the input gear 2406, without departing from the scope of the disclosure.

As described in more detail below, the input gear 2406 may be rotatably secured to the carriage 1626 with a channel retainer 2502 (only partially visible), and the channel retainer 2502 may be axially fixed to the carriage 1626 with a locking mechanism 2504. In the illustrated embodiment, the locking mechanism 2504 is depicted as a c-ring or an e-ring, but may alternatively comprise any other device or mechanism capable of axially fixing the channel retainer 2502 to the carriage 1626.

The third activating mechanism 1638c further includes a firing rod 2506 longitudinally extendable through the carriage 1626. In at least one embodiment, as illustrated, the firing rod 2506 may also extend at least partially through the input gear 2406. The firing rod 2506 extends along the longitudinal axis $A_1$ (FIG. 24) toward the end effector 1604 (FIGS. 16, 17B, 19) and is operatively coupled to the cutting element (knife) such that longitudinal movement of the firing rod 2506 correspondingly moves the knife in the same direction. In some embodiments, the firing rod 2506 extends to the end effector 1604 and directly couples to the knife. In other embodiments, however, the firing rod 2506 is coupled to a firing member (not shown) at some point between the carriage 1626 and the end effector 1604, and the firing member extends to the end effector 1604 to directly couple to the knife. In either scenario, actuation of the third activating mechanism 1638c causes the knife to "fire", i.e., advance or retract, depending on the rotational direction of the third spline 1624c.

Figure 26:
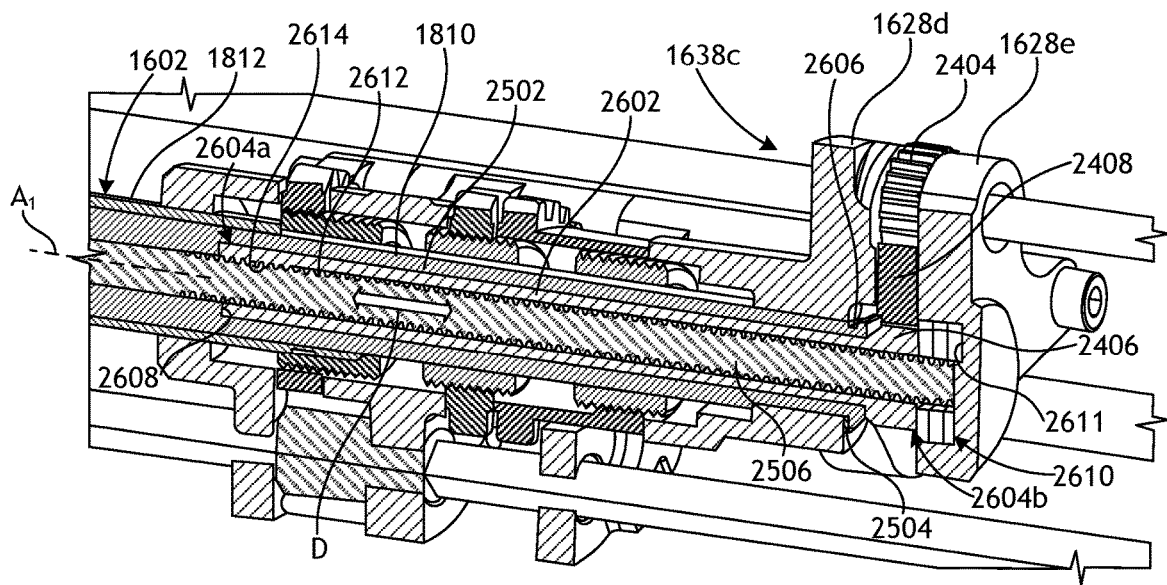
FIG. 26 is an isometric, cross-sectional side view of the third activating mechanism of FIGS. 24 and 25, according to one or more embodiments.

FIG. 26 is an isometric, cross-sectional side view of the third activating mechanism 1638c, according to one or more embodiments. As illustrated, the drive gear 2404 is intermeshed with the idler gear 2408, which correspondingly intermeshes with the input gear 2406. Alternatively, as mentioned above, the drive gear 2404 may directly intermesh with the input gear 2406.

The input gear 2406 may include or may otherwise be coupled to an elongate cylindrical body 2602 that has a first or "distal" end 2604a and a second or "proximal" end 2604b opposite the first end 2604a. As illustrated, the input gear 2406 is located at or near the second end 2604b. The elongate cylindrical body 2602 extends distally from the input gear 2406 within the shaft 1602 and, more particularly, within the inner grounding shaft 1810, which is at least partially arranged within the closure tube 1812. The channel retainer 2502 also extends within the inner grounding shaft 1810 and helps rotatably secure the input gear 2406 and the elongate cylindrical body 2602 to the carriage 1626. As illustrated, the channel retainer 2502 may comprise a cylindrical member sized to receive the elongate cylindrical body 2602 within its interior. The channel retainer 2502 may be axially fixed to the carriage 1626 with the locking mechanism 2504, which may be received within a groove 2606 defined on the proximal end of the channel retainer 2502.

The channel retainer 2502 may provide or otherwise define an inner radial shoulder 2608 configured to engage the first end 2604a of the elongate cylindrical body 2602 and thereby prevent the elongate cylindrical body 2602 from moving distally. At the second end 2604b of the elongate cylindrical body 2602, the channel retainer 2502 bears against one axial side (i.e., the distal end) of the input gear 2406, while one or more thrust bearings 2610 (three shown) bear against the opposite axial side (i.e., the proximal end) of the input gear 2406. In one or more embodiments, the thrust bearings 2610 may be received within a pocket 2611 defined in the fifth layer 1628e, and secured in place as the fifth layer 1628e is coupled to the fourth layer 1628d. Consequently, the input gear 2406 is secured axially in place between the channel retainer 2502 and the thrust bearings 2610 but simultaneously allowed to rotate about the longitudinal axis $A_1$. The thrust bearings 2610 may be configured to assume axial loading on the input gear 2406 as the third activating mechanism 1638c is actuated. The thrust bearings 2610 may also prove advantageous in reducing rotational friction of the input gear 2406 while driving (firing) the firing rod 2506.

Some or all of the firing rod 2506 may provide or otherwise define external threads 2612 configured to threadably engage internal threads 2614 provided at or near the first end 2604a of the elongate cylindrical body 2602. In example operation of the third activating mechanism 1638c, the third spline 1624c is rotated (via rotation of the fourth drive input 1636d of FIGS. 16 and 17B) and the drive gear 2404 correspondingly rotates to drive the input gear 2406 (either directly or through the idler gear 2408). Rotating the input gear 2406 correspondingly rotates the elongate cylindrical body 2602 in the same angular direction, which drives the internal threads 2614 of the body 2602 against the external threads 2612 of the firing rod 2506, and thereby advances or retracts the firing rod 2506 along the longitudinal axis $A_1$, as indicated by the arrows D. Longitudinal movement of the firing rod 2506 correspondingly moves the knife in the same direction at the end effector 1604 (FIGS. 16, 17B, 19).

Figure 27:
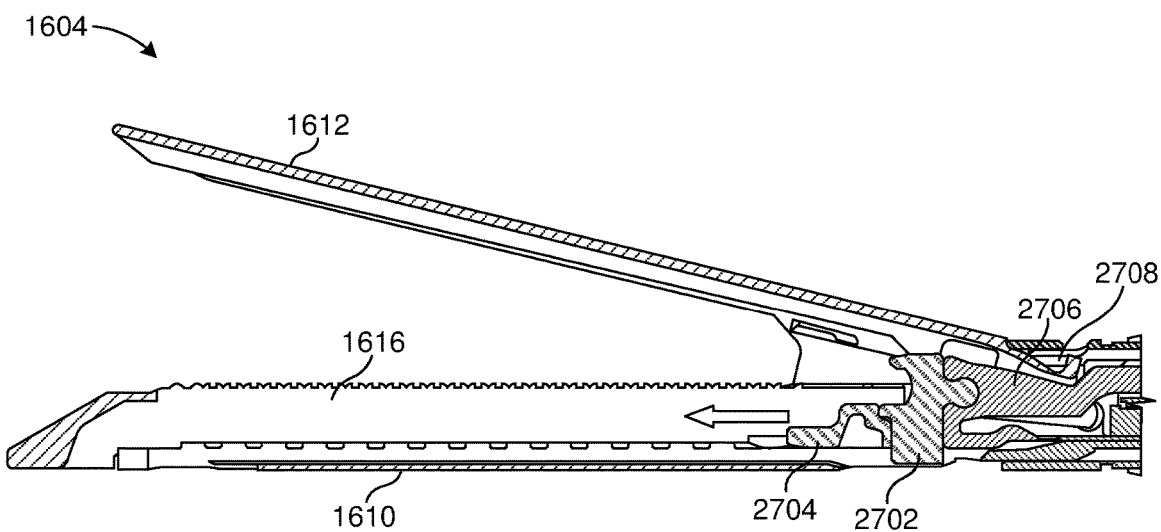
FIG. 27 is an enlarged cross-sectional view of the end effector of FIG. 16, according to one or more embodiments.

Referring to FIG. 27, with continued reference to FIG. 26, depicted is an enlarged cross-sectional view of the end effector 1604, according to one or more embodiments. As mentioned above, the end effector 1604 includes opposing jaws 1610, 1612 movable between open and closed positions, and the jaws 1610, 1612 are depicted in FIG. 27 in the open position. The end effector 1604 may further include a knife 2702 that can be linearly displaced within the slot 1616 defined in the second jaw 1610 to cut tissue grasped between the jaws 1610, 1612. As the knife 2702 advances distally within the slot 1616, a sled or camming wedge 2704 simultaneously engages a plurality of staples (not shown) contained within the first jaw 1610 (e.g., within a staple cartridge) and urges (cams) the staples into deforming contact with the opposing anvil surfaces (e.g., pockets) provided on the second jaw 1612. Properly deployed staples help seal opposing sides of the transected tissue.

As illustrated, the knife 2702 is operatively coupled to a firing member 2706 that extends proximally (i.e., to the right in FIG. 27) and is operatively coupled to the firing rod 2506 of FIGS. 25-26 at its proximal end. In other embodiments, however, the knife 2702 may be directly coupled to the firing rod 2506, without departing from the scope of the disclosure. Actuation of the firing rod 2506, as generally described above, causes the firing member 2706 to advance and retract and correspondingly advance and retract the knife 2702 so that it can transect tissue grasped between the jaws 1610, 1612. Distal movement of the firing member 2706 also correspondingly moves the camming wedge 2704 to deploy the staples, as described above.

In some embodiments, movement of the firing rod 2506 (FIGS. 25-26) in the distal direction may also cause the jaws 1610, 1612 to close. More specifically, in one or more embodiments, the rod 2506 (or the firing member 2706) or the knife 2702 may include a feature or structure (not shown) configured to engage an anvil 2708 provided on the upper jaw 1612. In such embodiments, as the firing rod 2506 is advanced distally, the feature or structure will axially engage the angled surface of the anvil 2708 and force the second jaw 1612 to close. This approach is commonly referred to as "knife-based" closure, and in such embodiments, the jaws 1610, 1612 may be spring biased to the open position when the knife 2702 is fully retracted. In other embodiments, however, as the firing rod 2506 is advanced distally, the closure tube 1812 (FIG. 26) may be simultaneously advanced in the same direction to engage the anvil 2708 and force the second jaw 1612 to close. This approach is commonly referred to as "tube-based" closure.

Clamping Mechanism on a Translating System

Figure 28A:
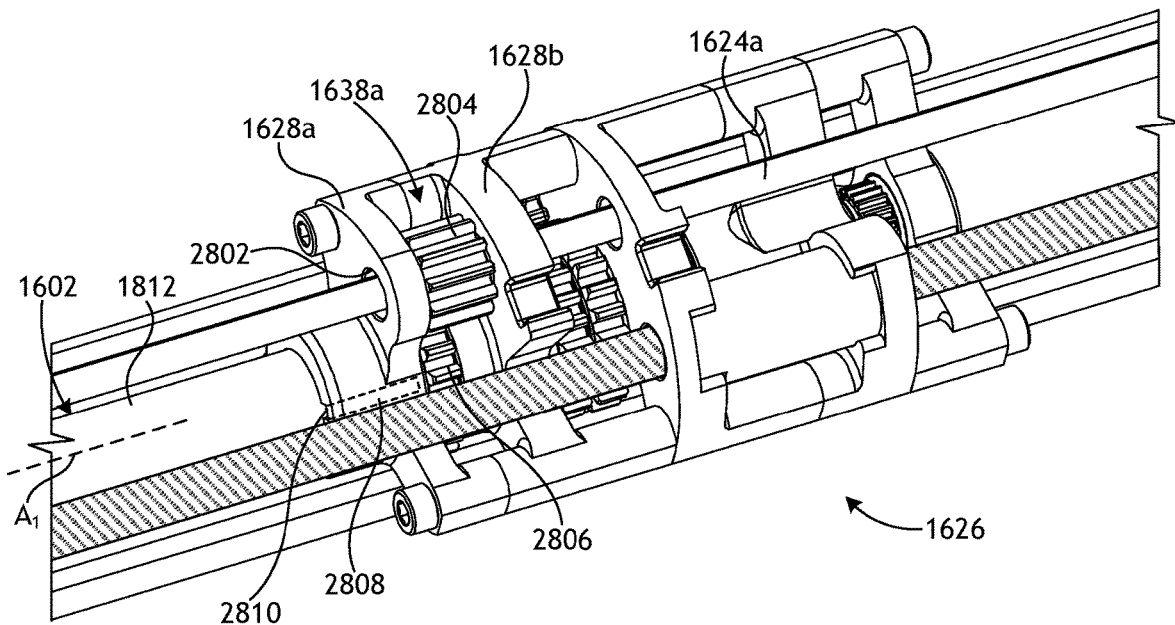
FIG. 28A is an enlarged isometric view of another embodiment of the carriage of FIG. 16.

FIG. 28A is an enlarged isometric view of another embodiment of the carriage 1626 of FIG. 16, and further provides an enlarged view of at least one embodiment of the first activating mechanism 1638a briefly described above. As mentioned herein, the first activating mechanism 1638a may be actuated or otherwise activated to open or close the jaws 1610, 1612 (FIGS. 16 and 17B) at the end effector 1604 (FIGS. 16 and 17B). More specifically, the first spline 1624a may be operatively coupled to the first activating mechanism 1638a such that rotating the first spline 1624a (via rotation of the second drive input 1636b of FIGS. 16 and 17B) will correspondingly actuate the first activating mechanism 1638a and thereby open or close the jaws 1610, 1612, depending on the rotational direction of the first spline 1624a.

As illustrated, the first spindle 1624a extends longitudinally through coaxially aligned apertures 2802 (only one visible) defined in the first and second layers 1628a,b of the carriage 1626. A drive gear 2804 may be included with the first spindle 1624a and located between adjacent portions of the first and second layers 1628a,b. The first spindle 1624a may exhibit a cross-sectional shape matable with a corresponding inner shape of the drive gear 2804 such that rotation of the first spindle 1624a correspondingly drives the drive gear 2804 in rotation. In some embodiments, the drive gear 2804 may comprise a separate component part slidably disposed about the outer surface of the first spindle 1624a. In such embodiments, as the carriage 1626 moves along the longitudinal axis $A_1$ (FIG. 16), the drive gear 2804 will correspondingly move along the length of the first spindle 1624a as captured between the first and second layers 1628a,b. In such embodiments, the apertures 2802 may include or otherwise define bearing surfaces (e.g., between the face of the drive gear 2804 and the layers 1628a,b and/or between an outer diameter collar of the drive gear 2804 and the inner diameter of the apertures 2820) to help reduce friction as the carriage 1626 traverses the first spindle 1624a. In other embodiments, however, the first spindle 1624a may be shaped and otherwise configured to operate as a drive gear. In such embodiments, the drive gear 2804 may be omitted to advantageously reduce the number of component parts.

The first activating mechanism 1638a may include a driven gear 2806, and the drive gear 2804 may be positioned on the carriage 1626 to engage or otherwise intermesh with the driven gear 2806. In other embodiments, however, one or more intermediate gears (e.g., idler gears) may interpose the drive gear 2804 and the driven gear 2806. Accordingly, as the first spline 1624a is rotated, the drive gear 2804 is able to drive the driven gear 2806 in rotation and thereby actuate the first activating mechanism 1638a. As illustrated, the driven gear 2806 may also be located between adjacent portions of the first and second layers 1628a,b of the carriage 1626.

The first activating mechanism 1638a may further include a key 2808 (shown in dashed lines) provided or otherwise defined on the outer surface of the shaft 1602 and, more particularly, on the outer surface of the closure tube 1812 of the shaft 1602. The key 2808 may be received within a slot 2810 defined in the carriage 1626 and, more particularly, in the first layer 1628a. In the illustrated embodiment, the key 2808 is depicted as an elongate member or protrusion, and the slot 2810 may define an opening sized to receive the key 2808. Actuating the first activating mechanism 1638a causes the closure tube 1812 to translate along the longitudinal axis $A_1$, which correspondingly causes the key 2808 to translate longitudinally within the slot 2810. With the key 2808 received within the slot 2810, the closure tube 1812 is prevented from rotating during longitudinal movement of the closure tube 1812 resulting from actuation of the first activating mechanism 1638a.

Figure 28B:
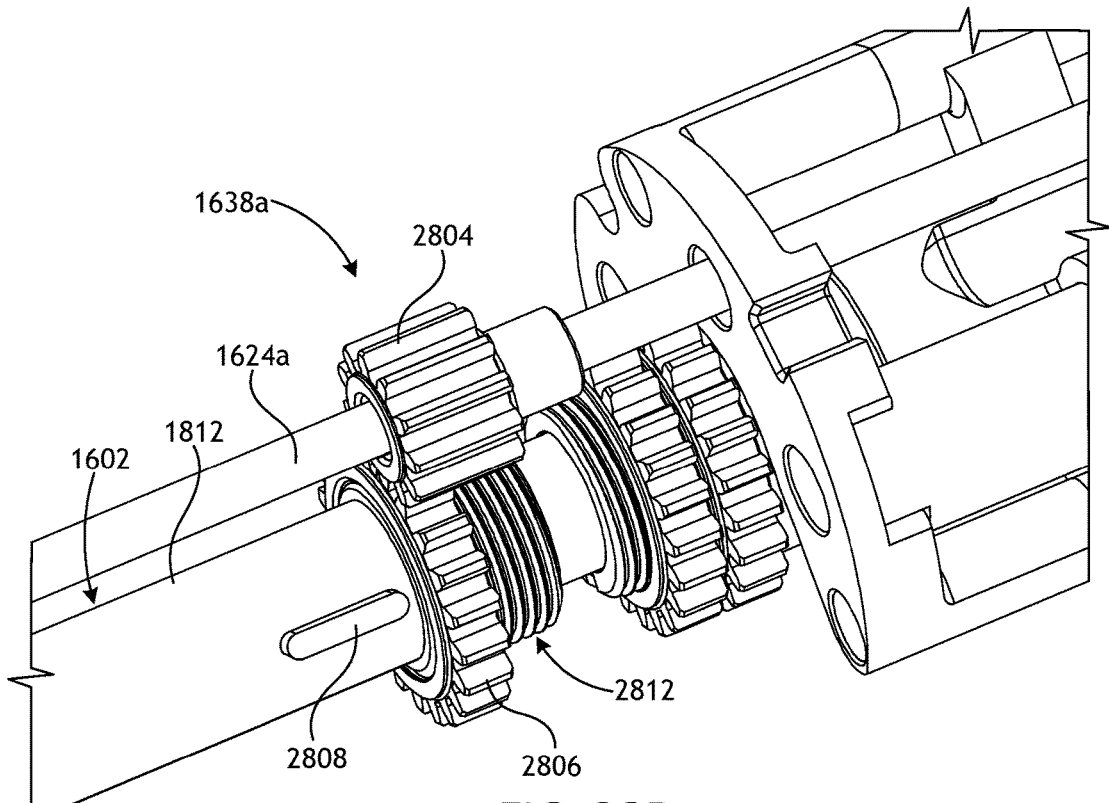
FIG. 28B is an enlarged isometric view of the first activating mechanism of FIG. 28A, according to one or more embodiments.

FIG. 28B is an enlarged isometric view of the first activating mechanism 1638a, according to one or more embodiments. Various parts of the carriage 1626, including the first and second layers 1626a,b (FIG. 28A), are omitted in FIG. 28B to enable a fuller view of the first activating mechanism 1638a. As illustrated, the driven gear 2806 may comprise an annular structure that extends about the closure tube 1812 of the shaft 1602, and the key 2808 is depicted as coupled to or otherwise defined on the outer surface of the closure tube 1812. Moreover, the gear teeth of the driven gear 2806 intermesh with gear teeth of the drive gear 2804 to enable the drive gear 2804 to rotate the driven gear 2806 when the first spline 1624a is rotated.

The first activating mechanism 1638a may further include a carrier 2812 arranged at the proximal end of the closure tube 1812. The driven gear 2806 is internally threaded and configured to threadably engage external threads defined by the carrier 2812. Consequently, as the drive gear 2804 rotates, the driven gear 2806 correspondingly rotates and moves the closure tube 1812 along the longitudinal axis $A_1$ (FIG. 28A) via the threaded engagement between the driven gear 2806 and the carrier 2812. Depending on the rotation direction of the drive gear 2804, the closure tube 1812 may be driven distally (i.e., to the left in FIG. 28B) or proximally (i.e., to the right in FIG. 28B).

In some embodiments, the carrier 2812 may form an integral part of the closure tube 1812 and thereby constitute the proximal end of the shaft 1602. In such embodiments, the proximal end of the shaft 1602 may be threaded to form the carrier 2812. In other embodiments, however, the carrier 2812 may comprise a separate component part arranged at the proximal end of the closure tube 1812. In such embodiments, the carrier 2812 may be configured to receive the proximal end of the closure tube 1812 and may radially interpose a portion of the closure tube 1812 and the driven gear 2806. In either scenario, movement of the carrier 2812 along the longitudinal axis $A_1$ (FIG. 28A), will correspondingly move the closure tube 1812 in the same axial direction.

Figure 28C:
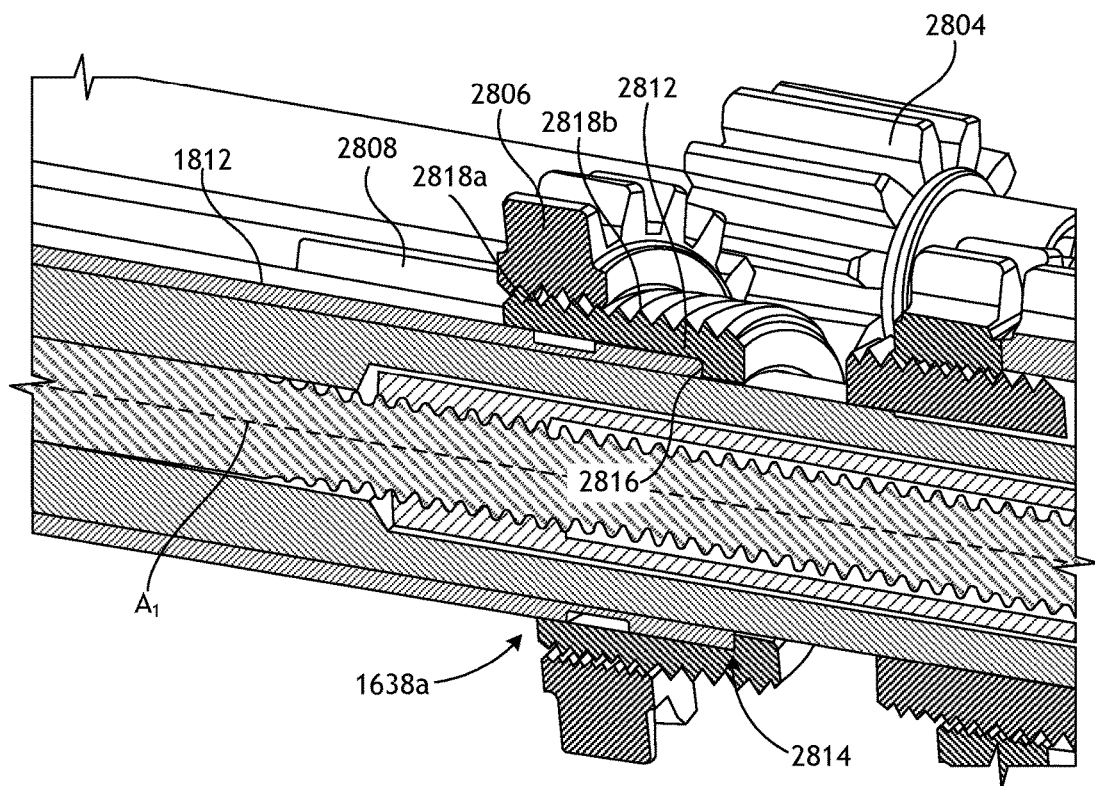
FIG. 28C is an isometric, cross-sectional side view of the first activating mechanism of FIGS. 28A-28B.

FIG. 28C is an isometric, cross-sectional side view of the first activating mechanism 1638a, according to one or more embodiments. In the illustrated embodiment, the carrier 2812 comprises a separate component part arranged at a proximal end 2814 of the closure tube 1812 and radially interposes a portion of the closure tube 1812 and the driven gear 2806. In such embodiments, the carrier 2812 may define an inner radial shoulder 2816 engageable with the proximal end 2814 of the closure tube 1812. As mentioned above, however, the carrier 2812 may alternatively form an integral part of the closure tube 1812 at the proximal end 2814, without departing from the scope of the disclosure.

The driven gear 2806 defines internal threading 2818a matable with external threading 2818b defined on the outer surface of the carrier 2812. As the driven gear 2806 is driven to rotate about the longitudinal axis $A_1$, the threaded engagement between the internal and external threadings 2818a,b causes the carrier 2812 to axially advance or retract along the longitudinal axis $A_1$, and correspondingly advance or retract the closure tube 1812 in the same axial direction. As the carrier 2812 advances distally (i.e., to the left in FIG. 28C), the inner radial shoulder 2816 bears against the proximal end 2814 of the closure tube 1812 and thereby forces the closure tube 1812 in the same distal direction. Advancing the closure tube 1812 distally forces the jaws 1610, 1612 (FIGS. 16 and 17B) to close, and retracting the closure tube 1812 proximally (i.e., to the right in FIG. 28C) allows the jaws 1610, 1612 to open.

In some embodiments, the thread pitch of the internal and external threadings 2818a,b and/or the gear ratio between the drive and driven gears 2804, 2806 may be altered or otherwise optimized to change load and speed needs for moving the closure tube 1812. This may prove advantageous since jaw closing typically has two functions: 1) grasping tissue for manipulation, which may require more precision movements (e.g., low load, speed control, precision, etc.), and 2) applying the tissue compression requirement to transect tissue and form staples (e.g., high load). The speed of the last stage of compression is key for the stabilization of the tissue as the fluid in the tissue is evacuated and compression is optimized for stapling and transection. Accordingly, the speed of compression should be slow, and slower than general motion of a jaw closing in the air. Moreover, as the closure tube 1812 advances or retracts, the key 2808 will slidably engage the slot 2810 (FIG. 28A) defined in the first layer 1628a (FIG. 28A) of the carriage 1626 (FIG. 28A) and thereby prevent the closure tube 1812 from rotating while moving longitudinally. This may be advantageous allowing only axial translation of the closure tube 1812 as the first activating mechanism 1638a is actuated.

Figure 29:
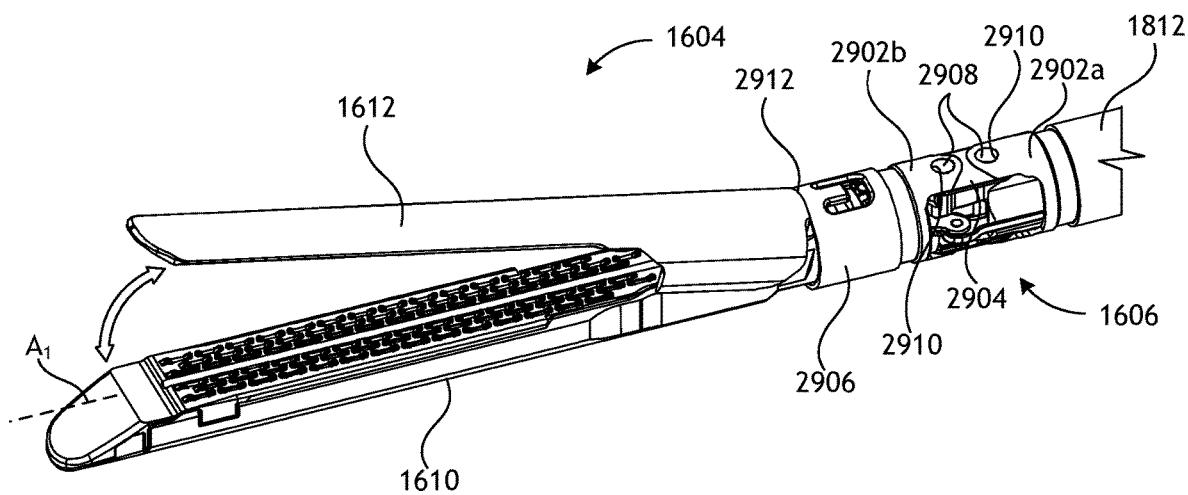
FIG. 29 is an enlarged view of the end effector and the wrist of FIG. 16, according to one or more embodiments.

Referring to FIG. 29, with continued reference to FIG. 28C, depicted is an enlarged view of the end effector 1604 and the wrist 1606, according to one or more embodiments. As illustrated, the wrist 1606 may include a first or "proximal" clevis 2902a, a second or "distal" clevis 2902b, and a closure link 2904 configured to operatively couple the proximal and distal devises 2902a,b across the wrist 1606. The proximal clevis 2902a may be coupled to or otherwise form part of the distal end of the closure tube 1812, and the distal clevis 2902b may be coupled to or otherwise form part of a closure ring 2906.

Axial movement of the closure tube 1812 along the longitudinal axis $A_1$, as generally described above, correspondingly moves the proximal clevis 2902a in the same axial direction, and the closure link 2904 is configured to transmit the axial load through (across) the wrist 1606 to close the jaws 1610, 1612 of the end effector 1604. More specifically, the closure link 2904 defines a pair of protrusions 2908 configured to mate with corresponding apertures 2910 defined in each of the proximal and distal devises 2902a,b. The closure link 2904 may transmit the closure load or translation of the closure tube 1812 from the distal clevis 2902b to the proximal clevis 2902a and the closure ring 2906 will correspondingly push or pull on the upper jaw 1612 to open or close the upper jaw 1612. To close the upper jaw 1612, the closure ring 2906 is forced against a shoulder 2912 at or near the back of the upper jaw 1612, which urges the upper jaw 1612 to pivot down and to the closed position. To open the upper jaw 1612, the closure ring 2906 is retracted proximally by retracting the closure tube 1812, and the closure ring 2906 helps pull the upper jaw 1612 back toward the open position. Alternatively, the upper jaw 1612 may be spring loaded and biased to the open position, and retracting the closure ring 2906 removes loading on the shoulder 2912, which allows the spring force to move the upper jaw 1612 to the open position.

Figure 30A:
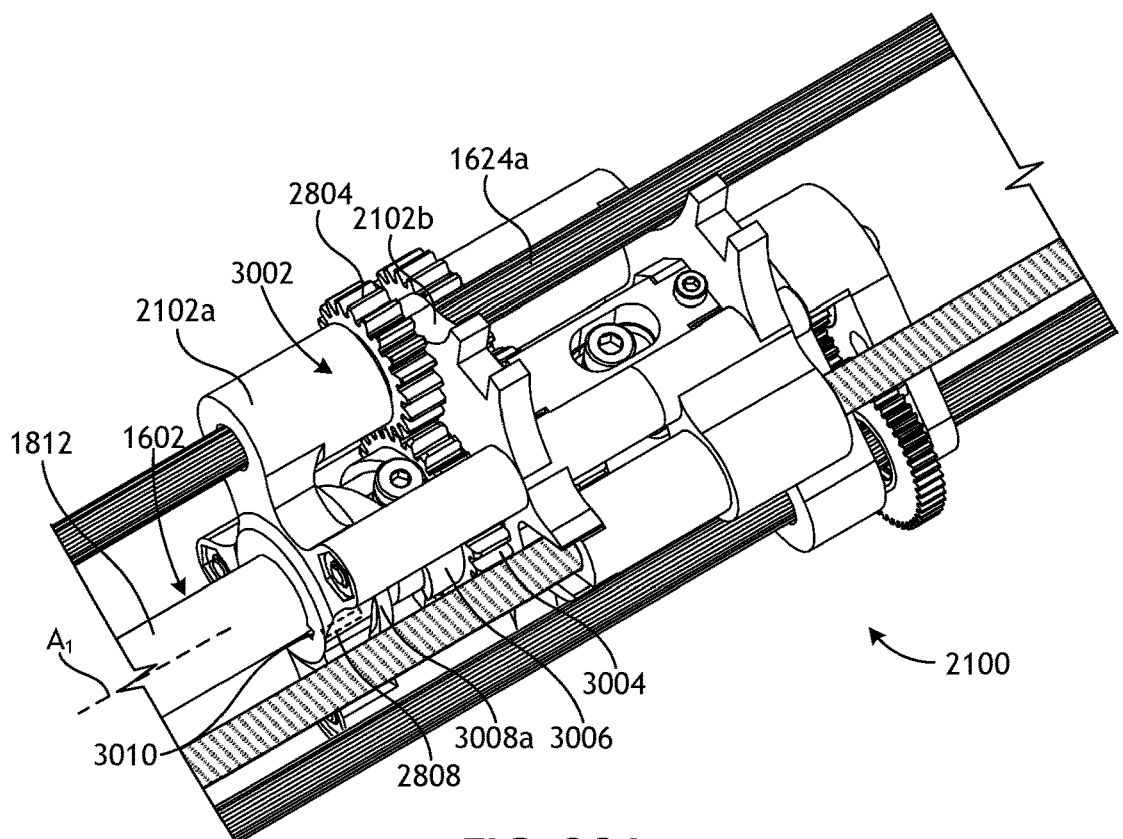
FIG. 30A is another enlarged isometric top view of the carriage of FIGS. 21A and 21B, according to one or more additional embodiments.

FIG. 30A is an enlarged isometric top view of the carriage 2100 of FIGS. 21A-21B, according to one or more additional embodiments. In the illustrated embodiment, the carriage 2100 includes an activating mechanism 3002 similar in some respects to the first activating mechanism 1638a of FIGS. 28A-28C. Similar to the first activating mechanism 1638a, for example, the activating mechanism 3002 may be actuated through rotation of the first spline 1624a and is operable to open or close the jaws 1610, 1612 (FIGS. 16, 17B, and 29) of the end effector 1604 (FIGS. 16, 17B, and 29). More specifically, the first spline 1624a may be operatively coupled to the activating mechanism 3002 such that rotating the first spline 1624a (e.g., via rotation of the second drive input 1636b of FIGS. 16 and 17B) correspondingly actuates the activating mechanism 3002 and thereby causes the closure tube 1812 of the shaft 1602 to advance or retract along the longitudinal axis $A_1$.

The activating mechanism 3002 includes a driven gear 3004, and the drive gear 2804 of the first spline 1624a may be positioned to intermesh with the driven gear 3004 such that rotation of the drive gear 2804 will correspondingly rotate the driven gear 3004 in the same direction. As illustrated, the driven gear 3004 may be coupled to or otherwise form part of a closure barrel 3006. As the spline 1624b is rotated, the drive gear 2804 drives the driven gear 3004 and causes the closure barrel 3006 to rotate about the longitudinal axis $A_1$.

The closure barrel 3006 may be positioned in the carriage 2100 between the first and second layers 2102a,b. One or more thrust bearings may be arranged at one or both axial ends of the closure barrel 3006 to help assume axial loading on the closure barrel 3006 as the activating mechanism 3002 operates. In the illustrated embodiment, one or more first thrust bearings 3008a (one shown) are arranged at the distal end of the closure barrel 3006 and may interpose the closure barrel 3006 and the first layer 2102a. In one or more embodiments, one or more additional thrust bearings (not shown) may be arranged at the proximal end of the closure barrel 3006 and interpose the closure barrel 3006 and a portion of the second layer 2102b, without departing from the scope of the disclosure. The thrust bearings 3008a may prove advantageous in reducing rotational friction as the closure barrel 3006 rotates.

The activating mechanism 3002 may further include the key 2808 (shown in dashed lines) provided or otherwise defined on the outer surface of the closure tube 1812. The key 2808 may be received within a slot 3010 defined in the first layer 2102a of the carriage 2100. Actuating the activating mechanism 3002 causes the closure tube 1812 to translate along the longitudinal axis $A_1$, which correspondingly causes the key 2808 to translate longitudinally within the slot 3010 and thereby help prevent the closure tube 1812 from rotating during longitudinal movement of the closure tube 1812.

Figure 30B:
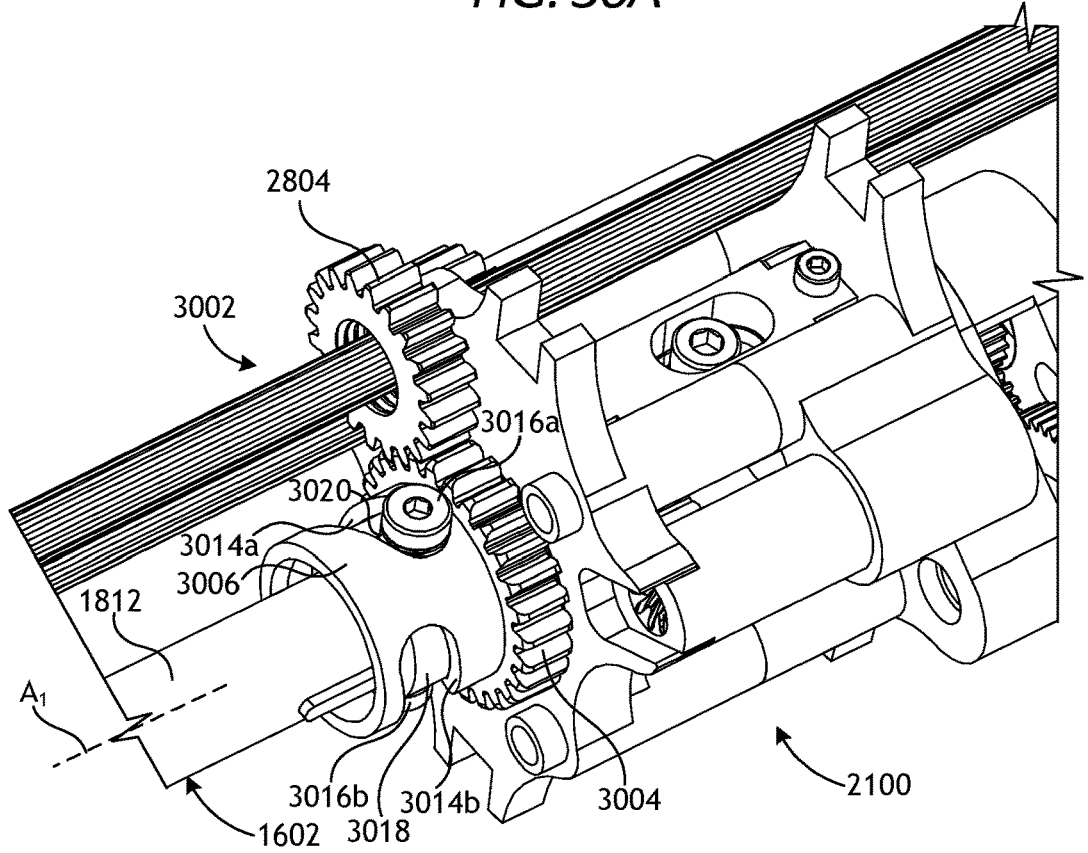
FIG. 30B is an enlarged view of the activating mechanism of FIG. 30A, according to one or more embodiments.

FIG. 30B is an enlarged isometric view of the activating mechanism 3002, according to one or more embodiments. Various component parts of the carriage 2100 are omitted in FIG. 30B, such as the first layer 2102a (FIG. 30A), to enable a fuller view of various parts of the activation mechanism 3002. As illustrated, the closure barrel 3006 may comprise a generally cylindrical structure that extends about the shaft 1602 and, more particularly, about the closure tube 1812. The closure barrel 3006 defines or otherwise provides one or more cam slots or profiles, shown in FIG. 30B as a first cam profile 3014a and a second cam profile 3014b. Each cam profile 3014a,b extends a distance about the circumference of the closure barrel 3006 (e.g., in a generally helical pattern). While the closure barrel 3006 provides two cam profiles 3014a,b, it is contemplated herein to only include one cam profile, without departing from the scope of the disclosure.

As illustrated, the activating mechanism 3002 further includes a first follower pin 3016a and a second follower pin 3016b. The first and second follower pins 3016a,b extend through the first and second cam profiles 3014a,b, respectively, and are operatively coupled (directly or indirectly) to the proximal end of the closure tube 1812. In the illustrated embodiment, the first and second follower pins 3016a,b are each coupled to a carrier 3018 arranged at the proximal end of the closure tube 1812. In some embodiments, the carrier 3018 may form an integral part of the closure tube 1812 and thereby constitute the proximal end of the closure tube 1812. In other embodiments, however, the carrier 3018 may comprise a separate component part arranged at the proximal end of the closure tube 1812. In such embodiments, the carrier 3018 may be configured to receive the proximal end of the closure tube 1812 and may radially interpose a portion of the closure tube 1812 and the closure barrel 3006. In either scenario, movement of the carrier 3018 along the longitudinal axis $A_1$, will correspondingly move the closure tube 1812 in the same axial direction.

As the drive gear 2804 drives the driven gear 3004, the closure barrel 3006 correspondingly rotates about the longitudinal axis $A_1$, thus urging the follower pins 3016a,b to traverse the cam profiles 3014a,b, respectively. As the follower pins 3016a,b traverse the cam profiles 3014a,b, the carrier 3018 is moved along the longitudinal axis $A_1$ and the closure tube 1812 is urged in the same axial direction. Depending on the rotation direction of the drive gear 2804, the carrier 3018 and the closure tube 1812 may be moved distally (i.e., to the left in FIG. 30B) or proximally (i.e., to the right in FIG. 30B) and thereby close or open the jaws 1610, 1612 (FIGS. 16, 17B, and 29) of the end effector 1604 (FIGS. 16, 17B, and 29).

In some embodiments, as illustrated, one or both of the follower pins 3016a,b may including one or more bearings 3020 (one visible), and the shaft of each follower pin 3016a,b extends through the bearings 3020. The bearings 3020 may be configured to bear against the inner walls of the cam profiles 3014a,b as the closure barrel 3006 rotates and the follower pins 3016*a,b* traverse the cam profiles 3014*a,b*, respectively. The bearings 3020 help reduce friction during actuation. Alternatively, or in addition thereto, one or both of the follower pins 3016*a,b* may exhibit a surface finish or include a coating that reduces friction. In at least one embodiment, for instance, one or both of the follower pins 3016*a,b* may be coated with a lubricant or lubricious substance, such as polytetrafluoroethylene (PTFE or TEFLON®) or an ultrahigh molecular weight (UMHL) polymer.

Figure 30C:
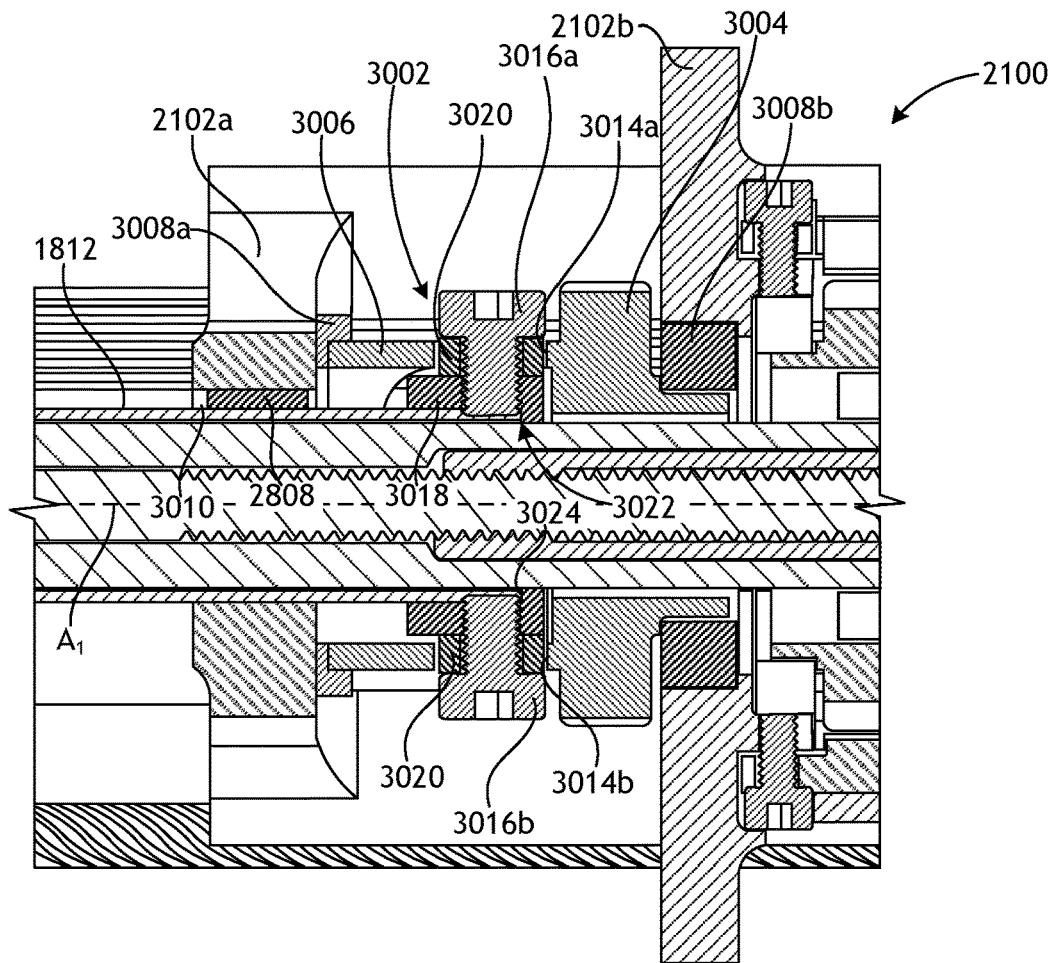
FIG. 30C is a cross-sectional side view of a portion of the carriage of FIGS. 30A-30B and the activation mechanism of FIGS. 30A-30B.

FIG. 30C is a cross-sectional side view of a portion of the carriage 2100 and the activation mechanism 3002. As illustrated, the closure barrel 3006 is positioned between the first and second layers 2102*a,b*. The first thrust bearing 3008*a* is arranged at the distal end of the closure barrel 3006 and interpose the closure barrel 3006 and the first layer 2102*a*, and one or more second thrust bearings 3008*b* (one shown) may be arranged at the proximal end of the closure barrel 3006 and interpose the closure barrel 3006 and a portion of the second layer 2102*b*. The thrust bearings 3008*a,b* help assume axial loading on the closure barrel 3006 and reduces rotational friction as the closure barrel 3006 rotates.

In the illustrated embodiment, the carrier 3018 comprises a separate component part arranged at a proximal end 3022 of the closure tube 1812 and radially interposes a portion of the closure tube 1812 and the closure barrel 3006. In such embodiments, the carrier 3018 may define an inner radial shoulder 3024 engageable with the proximal end 3022 of the closure tube 1812. As mentioned above, however, the carrier 3028 may alternatively form an integral part of the closure tube 1812 at the proximal end 3022.

The follower pins 3016*a,b* extend through the corresponding cam profiles 3014*a,b*, respectively, to be coupled to the carrier 3018. In some embodiments, the follower pins 3016*a,b* may be threaded to the corresponding carrier 3018, but may alternatively be secured to the carrier 3018 in other ways, such as through an interference (shrink) fit, welding, an adhesive, a snap fit, or any combination thereof. In other embodiments, the follower pins 3016*a,b* may be merely received within corresponding apertures defined in the carrier 3018, and not necessarily fixed thereto, without departing from the scope of the disclosure. As illustrated, the bearings 3020 are able to bear against the inner walls of the corresponding cam profiles 3014*a,b*.

While actuating the activation mechanism 3002, the drive gear 2804 (FIGS. 30A-3B) drives the driven gear 3004 and thereby rotates the closure barrel 3006 about the longitudinal axis $A_1$. As the closure barrel 3006 rotates, the follower pins 3016*a,b* traverse the cam profiles 3014*a,b*, respectively, and the carrier 3018 and the closure tube 1812 are correspondingly urged to move axially along the longitudinal axis $A_1$. Depending on the rotation direction of the drive gear 2804, the carrier 3018 and the closure tube 1812 may be moved distally (i.e., to the left in FIG. 30C) or proximally (i.e., to the right in FIG. 30C) and thereby close or open the jaws 1610, 1612 (FIGS. 16, 17B, and 29) of the end effector 1604 (FIGS. 16, 17B, and 29). Moreover, as the closure tube 1812 advances or retracts, the key 2808 will slidably engage the slot 3010 defined in the first layer 2102*a* of the carriage 2100 and thereby prevent the closure tube 1812 from rotating. This may be advantageous in preventing the closure tube 1812 from rotating and only allowing axial translation of the closure tube 1812 as the activating mechanism 3002 is actuated.

Figure 31:
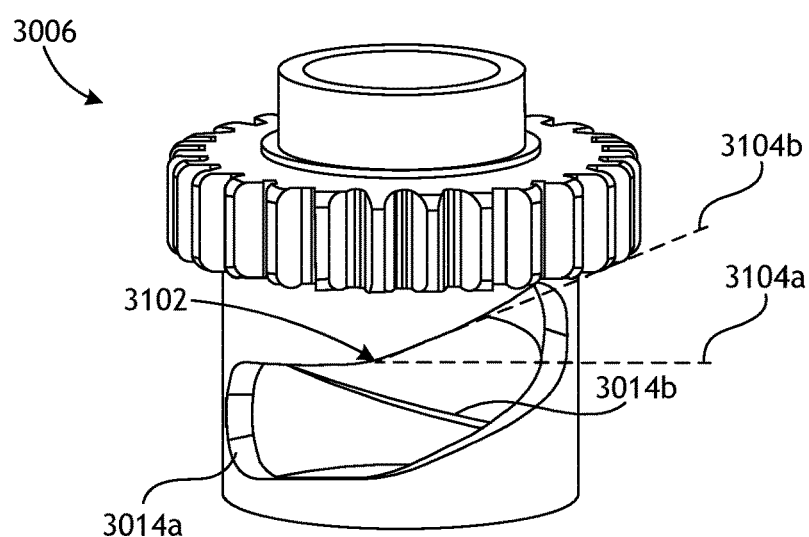
FIG. 31 is an isometric view of an example embodiment of the closure barrel of FIGS. 30A-30C, according to one or more embodiments.

FIG. 31 is an isometric view of an example embodiment of the closure barrel 3006, according to one or more embodiments. Each cam profile 3014*a,b* may comprise a slot that extends generally helically about a portion of the circumference of the closure barrel 3006. Accordingly, the cam profiles 3014*a,b* may be characterized as helical cam slots and the follower pins 3016*a,b* may be characterized as linear cam followers. The cam profiles 3014*a,b* may prove advantageous in making the system easier to back-drive and open or close the jaws 1610, 1612 (FIGS. 16, 17B, and 29) manually, as needed.

In some embodiments, each cam profile 3014*a,b* may comprise a straight slot extending helically at a constant angle or slope about the circumference of the closure barrel 3006. In such embodiments, the movement and force applied to the carrier 3018 and converted into an axial load on the closure tube 1812 (FIGS. 30A-30C) will be constant during actuation of the activation mechanism 3002 (FIGS. 30A-30C).

In other embodiments, however, one or both of the cam profiles 3014*a,b* may not be entirely straight but may alternatively diverge at one or more inflection points 3102 along the helical length (path) of the cam profile 3014*a,b*. More specifically, at the inflection point 3102, the cam profiles 3014*a,b* may change from extending a first distance about the circumference of the closure barrel 3006 at a first slope 3104*a* to a second distance at a second slope 3104*b*, where the second slope 3104*b* comprises a more or less aggressive path as compared to the first slope 3104*a*. A higher or lower angle or slope of the cam profile 3014*a,b* will correspondingly alter the mechanical advantage obtained as the follower pins 3016*a,b* traverse the cam profiles 3014*a,b* and act on the interconnected carrier 3018. This can result in higher axial loads being applied to the closure tube 1812 (FIGS. 30A-30B), which allows the jaws 1610, 1612 (FIGS. 16, 17B, and 29) to clamp down with enhanced force when needed. More particularly, and as mentioned above, jaw closing functions to grasp tissue for manipulation, which may require more precision movements, and applying compressive forces to the tissue, which requires higher loads. The varying slopes 3104*a,b* may help the jaws 1610, 1612 operate more effectively, as needed.

Translation Through Tool Drive

Figure 32:
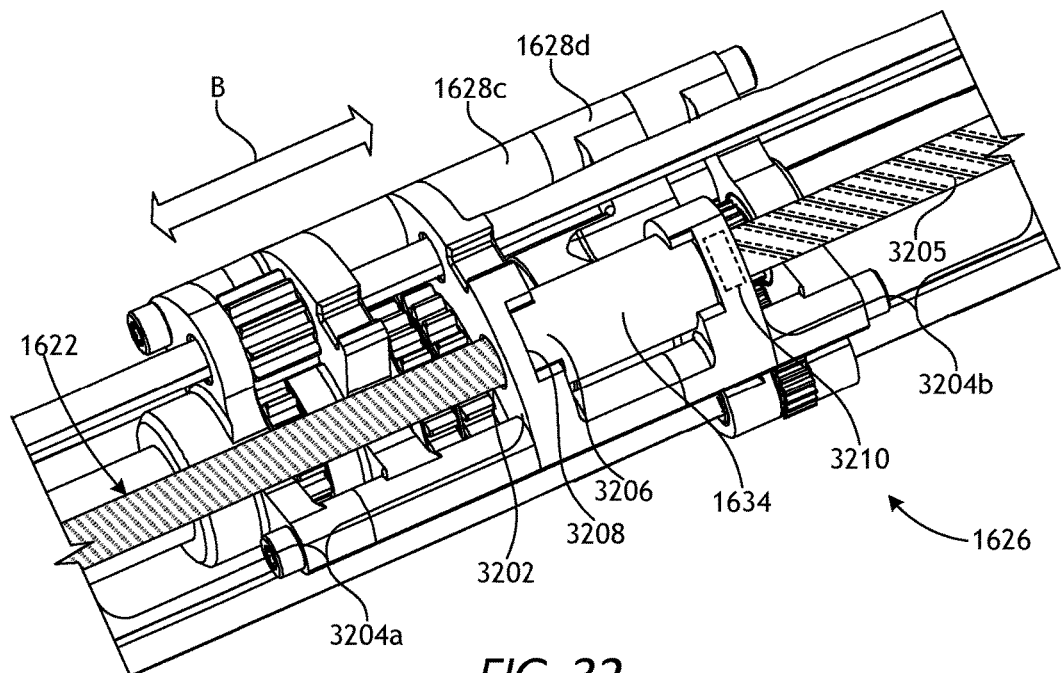
FIG. 32 is another enlarged isometric view of the carriage of FIG. 16.

FIG. 32 is another enlarged isometric view of the carriage 1626 of FIG. 16. As discussed with reference to FIG. 16, the shaft 1602 is coupled to and extends distally from the carriage 1626 and penetrates the first end 1618*a* (FIG. 16) of the drive housing 1614 (FIG. 16). Moreover, the carriage 1626 is movable between the first and second ends 1618*a,b* (FIG. 16) along the longitudinal axis $A_1$ to advance or retract the end effector 1604 (FIG. 16) relative to the drive housing 1614, as indicated by the arrows B (i.e., z-axis translation).

In one or more embodiments, as briefly discussed above, axial translation of the carriage 1626 may be accomplished through the use and mechanical interaction of the lead screw 1622 and the carriage nut 1634. As illustrated, the carriage 1626 may be at least partially mounted to the lead screw 1622 by having the lead screw 1622 extend through one or more portions of the carriage 1626, such as adjacent portions of the third and fourth layers 1628*c,d*. In the illustrated embodiment, the lead screw 1622 extends through coaxially aligned apertures 3202 (only one shown) defined in adjacent portions of the third and fourth layers 1628*c,d*.

The carriage 1626 is configured to traverse the axial length of the lead screw 1622 by mechanical interaction with the carriage nut 1634. More particularly, the outer surface of the lead screw 1622 defines outer helical threading and the carriage nut 1634 defines corresponding internal helical threading (not shown) matable with the outer helical threading of the lead screw 1622. The carriage nut 1634 is immovably secured to the carriage 1626 such that rotation of the lead screw 1622 causes the carriage nut 1634 to convert the rotational force of the lead screw 1622 into an axial load applied to the carriage 1626. Consequently, the carriage nut 1634 is urged to traverse the outer helical threading of the lead screw 1622 and thereby advance or retract the carriage 1626 along the longitudinal axis $A_1$ in the direction(s) B. As the carriage 1626 moves along the longitudinal axis $A_1$, the end effector 1604 (FIG. 16) correspondingly advances or retracts relative to the drive housing 1614. Depending on the rotational direction of the lead screw 1622, the carriage 1626 and the end effector 1604 may be moved distally (i.e., to the left in FIG. 32) or proximally (i.e., to the right in FIG. 32).

In some embodiments, the outer helical threading of the lead screw 1622 may be uniform (constant) along the entire length of the lead screw 1622. In such embodiments, the outer helical threading will be provided (defined) at a single common pitch between both ends of the lead screw 1622. In other embodiments, however, the pitch of the outer helical threading may vary along portions of the lead screw 1622. As illustrated, for example, a first portion 3204a of the lead screw 1622 may provide outer helical threading defined at a first pitch, while a second portion 3204b of the lead screw 1622 may provide outer helical threading defined at a second pitch different from the first pitch. In the illustrated embodiment, the second pitch defined on the second portion 3204b is more aggressive as compared to the first pitch defined on the first portion 3204a. As a result, while the lead screw 1622 is rotated at a constant speed, the carriage 1626 will move along the longitudinal axis $A_1$ at a faster speed while traversing the second portion 3204b as compared to traversing the first portion 3204a. This may prove advantageous in allowing the operator to advance the end effector (FIG. 16) toward a surgical site faster along select portions of the lead screw 1622.

The lead screw 1622 may be made of a variety of rigid materials including, but not limited to, a plastic (e.g., an extruded polymer), a metal (e.g., aluminum, stainless steel, brass, etc.), a composite material (e.g., carbon fiber, fiberglass, etc.), or any combination thereof. The lead screw 1622 may exhibit a surface finish or include a coating that reduces friction against the carriage nut 1634 when the carriage 1626 is under loading, i.e., twisting or compressive loads. In at least one embodiment, for instance, the outer helical threading of the lead screw 1622 may be coated with a lubricant or lubricious substance 3205, such as polytetrafluoroethylene (PTFE or TEFLON®), or may otherwise comprise an anodized surface.

In some embodiments, as illustrated, the carriage nut 1634 may comprise a separate component part mounted to the lead screw 1622 and secured to the carriage 1626, such as between adjacent portions of the third and fourth layers 1628c,d. In such embodiments, the carriage nut 1634 may provide or otherwise define an anti-rotation feature 3206 matable with a corresponding feature 3208 defined on the carriage 1626. The anti-rotation feature 3206 may be configured to transfer rotational loading assumed by the carriage nut 1634 through rotation of the lead screw 1622 to the carriage 1626. As a result, the rotational loading can be converted into axial loading that helps move the carriage 1626 along the longitudinal axis $A_1$. In the illustrated embodiment, the anti-rotation feature 3206 comprises a flange and the feature 3208 comprises a pocket or recess configured to receive the flange.

In other embodiments, however, the carriage nut 1634 may form an integral part of the carriage 1626. In such embodiments, one or both of the third and fourth layers 1628c,d may operate as the carriage nut 1634. More specifically, the carriage nut 1634 may be arranged within one or both of the co-axially aligned apertures 3202, as indicated by the dashed box 3210. Alternatively, one or both of the co-axially aligned apertures 3202 may be internally threaded to mate with the outer helical threading of the lead screw 1622. In such embodiments, rotation of the lead screw 1622 will correspondingly drive the carriage 1626 distally or proximally as threadably interacting with the threaded aperture(s) 3202.

Figure 33A:
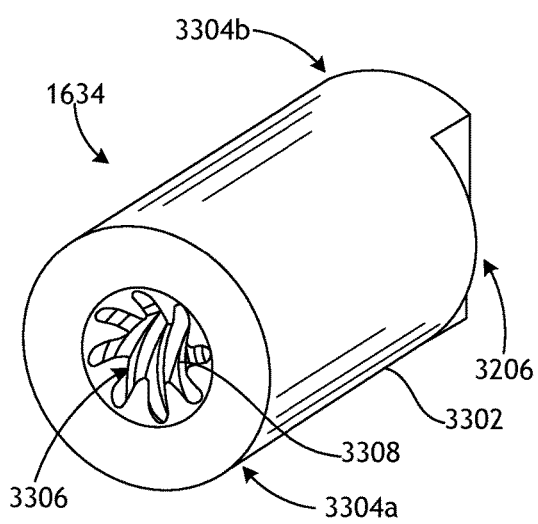
FIGS. 33A and 33B are isometric end views of the carriage nut of FIGS. 16 and 32, according to one or more example embodiments.
Figure 33B:
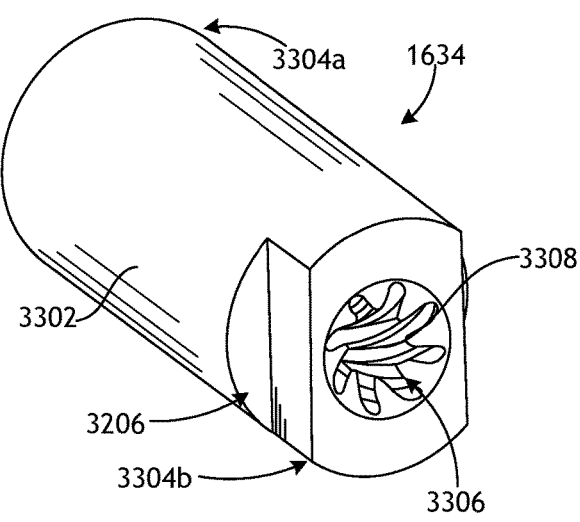

FIGS. 33A and 33B are opposing isometric end views of the carriage nut 1634, according to one or more embodiments. As illustrated, the carriage nut 1634 provides a generally cylindrical body 3302 having a first end 3304a and a second end 3304b opposite the first end 3304a. A central conduit 3306 may be defined in the body 3302 and extend between the first and second ends 3304a,b. As illustrated, internal helical threading 3308 may be defined on the inner wall of the central conduit 3306 and may be configured to threadably mate with the external helical threading defined on the lead screw 1622 (FIG. 32).

In some embodiments, one or both of the ends 3304a,b may provide or otherwise define the anti-rotation feature 3206 configured to prevent the carriage nut 1634 from rotating while traversing the lead screw (FIG. 32). In the illustrated embodiment, the anti-rotation feature 3206 is provided at the second end 3304b, but could alternatively be provided at the first end 3304a or both ends 3304a,b. Once the anti-rotation feature 3206 is received within the corresponding feature 3208 (FIG. 32) defined on the carriage 1626 (FIG. 32), the carriage nut 1634 will be prevented from rotating relative to the carriage 1626, which allows the rotational force from the lead screw 1622 to be transferred through the carriage nut 1634 to the carriage 1626 in the form of an axial load that causes axial movement of the carriage 1626.

Figure 34A:
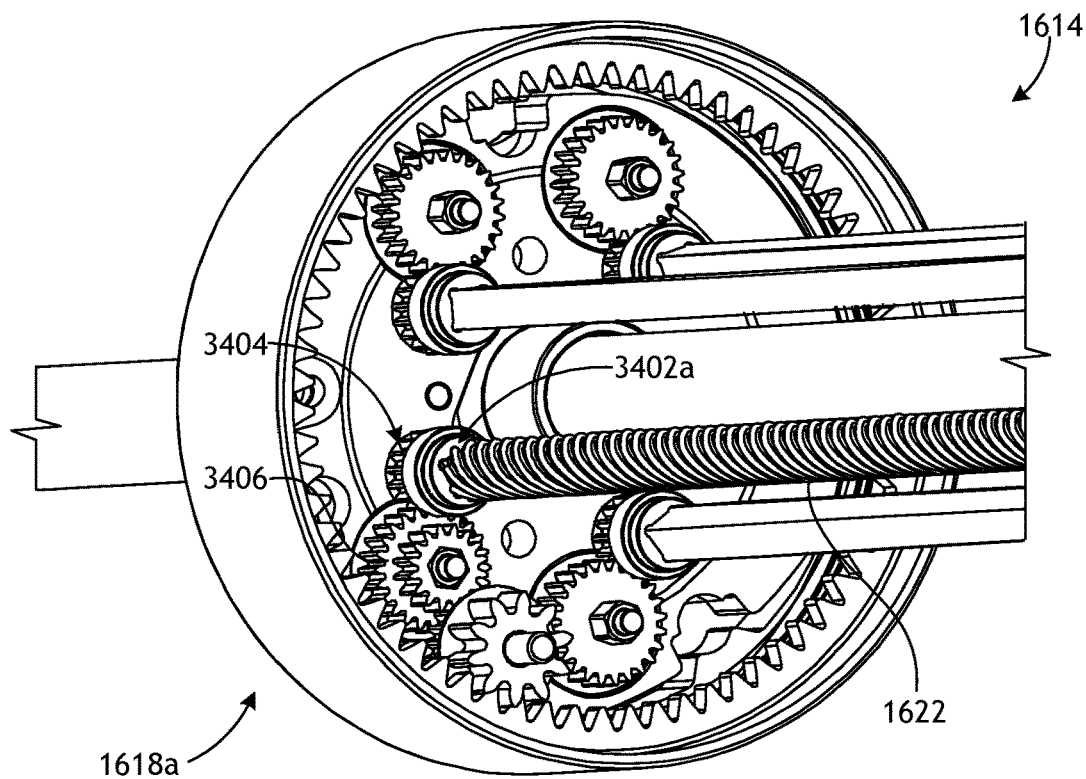
FIGS. 34A and 34B are isometric views of the first and second ends, respectively, of the handle of FIG. 16, according to one or more embodiments.
Figure 34B:
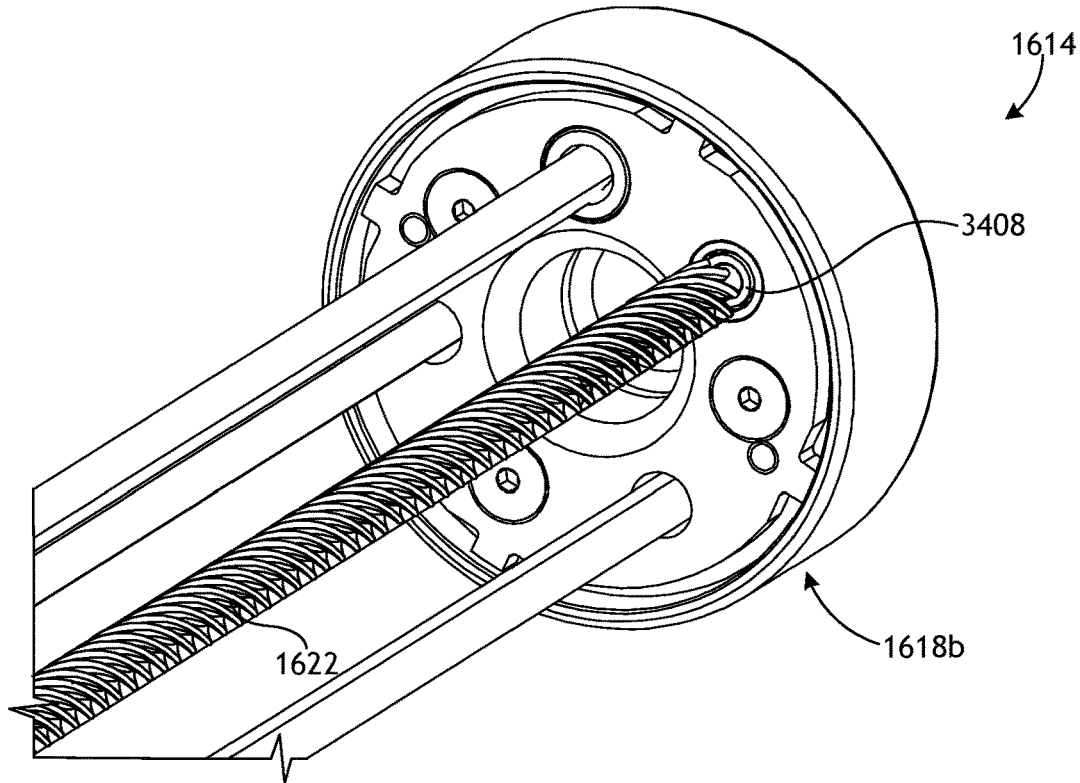

FIGS. 34A and 34B are isometric views of the first and second ends 1618a,b, respectively, of the drive housing 1614 of FIG. 16, according to one or more embodiments. The lead screw 1622 extends between and is rotatably mounted to the first and second ends 1618a,b of the drive housing 1614. More specifically, a first or "distal" end 3402a (FIG. 34A) of the lead screw 1622 is rotatably mounted to the first end 1618a of the drive housing 1614, and a second or "proximal" end 3402b (FIG. 34B) of the lead screw 1622 is rotatably mounted to the second end 1618b of the drive housing 1614. Each end 3402a,b of the lead screw 1622 is axially supported at the first and second ends 1618a,b, respectively to help prevent (minimize) linear movement of the lead screw 1622, while simultaneously allowing unrestricted rotational movement.

Referring to FIG. 34A, a driven gear 3404 is provided at or otherwise forms part of the distal end 3402a of the lead screw 1622. The driven gear 3404 is arranged to intermesh with a drive gear 3406 rotatably mounted at the first end 1618a of the drive housing 1614. The drive gear 3406 may form part of or may otherwise be operatively coupled to the first drive input 1636a (FIGS. 16 and 17B) such that rotation of the first drive input 1636a (via the first drive output 1724a of the instrument driver 1702 of FIGS. 17A-17B) correspondingly rotates the driven gear 3404, which causes rotation of the lead screw 1622. In other embodiments, the driven gear 3404 may be driven by a combination of the first drive input 1636a and at least one additional drive input (not shown). Using an additional drive input may be required if the torsional forces are high and can be distributed between two inputs. In at least one embodiment, the first drive input 1636a may comprise a direct input into the lead screw 1622 versus an arranged intermeshing of gears.

Referring to FIG. 34B, the proximal end 3402b of the lead screw 1622 may be rotatably mounted to the second end 1618a of the drive housing 1614. In some embodiments, one or more thrust bearings 3408 may be arranged at the proximal end 3402b of the lead screw 1622 to reduce rotational friction of the lead screw 1622 as it rotates.

Figure 35:
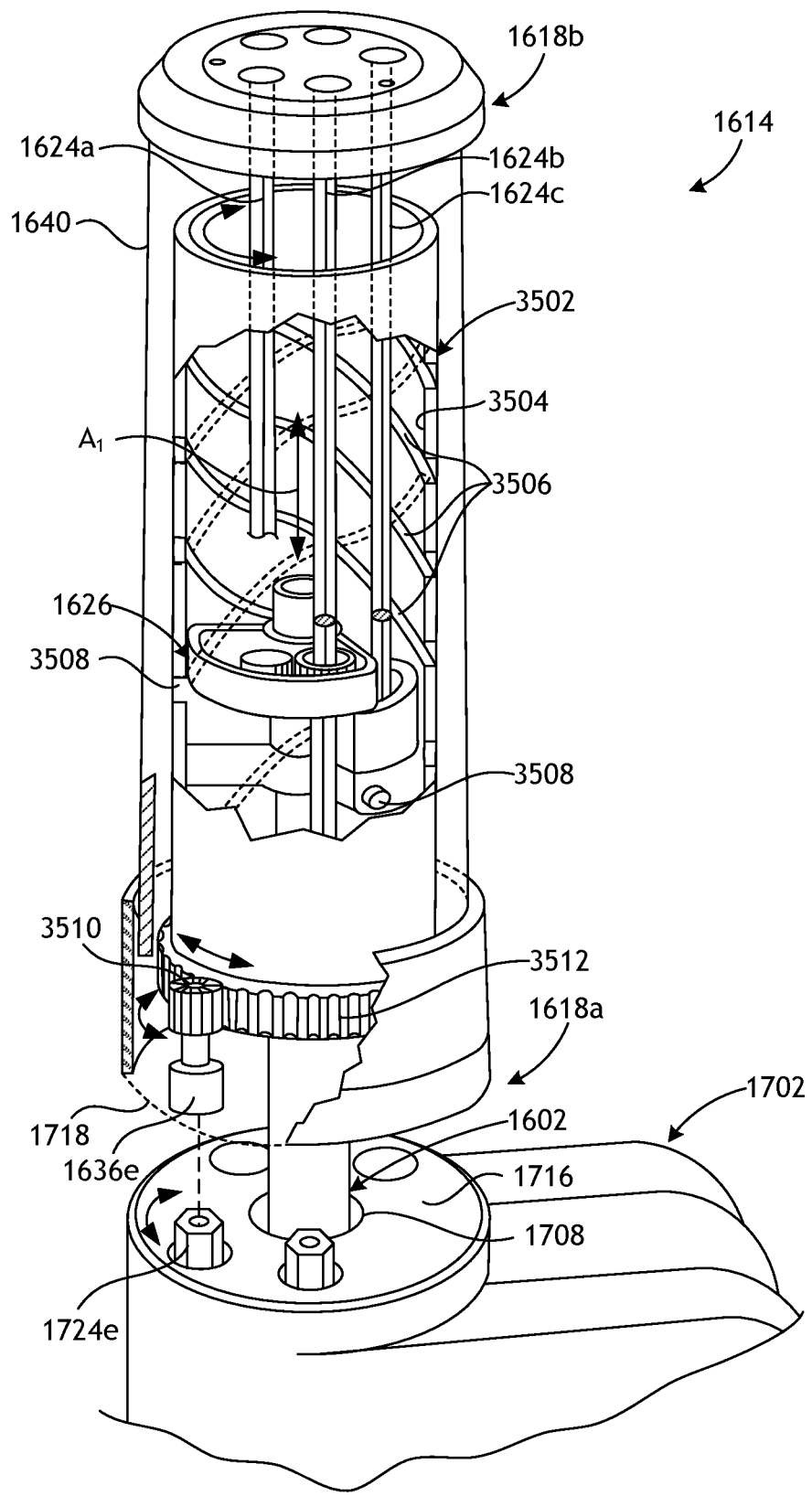
FIG. 35 is another example of the handle of FIG. 16, according to one or more additional embodiments.

FIG. 35 is another example of the drive housing 1614 of FIG. 16, according to one or more additional embodiments. As illustrated, the drive housing 1614 includes the first and second ends 1618a,b and the splines 1624a-c extending longitudinally between the first and second ends 1618a,b. The carriage 1626 is movably mounted to the splines 1624a-c and the shaft 1602 extends distally from the carriage 1626 through the first end 1618a of the drive housing 1614 and subsequently through the central aperture 1708 of the instrument driver 1702. The drive housing 1614 may be releasably coupled to the instrument driver 1702 by extending the shaft 1602 through the central aperture 1708 and mating the drive interface 1716 of the instrument driver 1702 to the driven interface 1718 of the drive housing 1614, as generally described above.

The carriage 1626 is movable between the first and second ends 1618a,b along the longitudinal axis $A_1$ and is thereby able to advance or retract the end effector 1604 (FIGS. 16 and 17B) relative to the drive housing 1614 in z-axis translation. In the illustrated embodiment, z-axis translation of the carriage 1626 may be accomplished using a cylindrical lead screw 3502 forming part of the drive housing 1614. As illustrated, the cylindrical lead screw 3502 comprises a hollow cylinder that exhibits a generally circular cross section. The cylindrical lead screw 3502 is operatively coupled to the first end 1618a of the drive housing 1614 and extends toward the second end 1618b. In some embodiments, as illustrated, the cylindrical lead screw 3502 stops short of the second end 1618b, but may alternatively terminate at the second end 1618b, without departing from the scope of the disclosure.

The cylindrical lead screw 3502 defines an interior 3504 sized to receive the splines 1624a-c and the carriage 1626. Moreover, one or more cam channels or profiles 3506 (three shown) may be defined on the inner surface of the interior 3504 and configured to receive corresponding follower pins 3508 (two visible) provided or otherwise defined on the outer periphery of the carriage 1626. In some embodiments, the follower pins 3508 may comprise tabs or protrusions extending radially outward from the outer periphery of the carriage 1626. The cam profiles 3506 form parallel helical paths that extend along all or a portion of the interior 3504, and the follower pins 3508 may be configured to traverse the cam profiles 3506 and thereby move the carriage 1626 in z-axis translation. More specifically, the cylindrical lead screw 3502 may be configured to rotate about the longitudinal axis $A_1$ relative to the carriage 1626, and as the cylindrical lead screw 3502 rotates, the follower pins 3508 will traverse the corresponding cam profiles 3506. The helical shape of the cam profiles 3506 urges the carriage 1626 to move proximally or distally in z-axis translation, depending on the rotational direction of the cylindrical lead screw 3502.

In the illustrated embodiment, the cylindrical lead screw 3502 may be rotated through actuation of a drive input associated with the drive housing 1614 and arranged in the first end 1618a. More particularly, the drive housing 1614 may include a fifth drive input 1636e matable with the fifth drive output 1724e of the instrument driver 1702. Once properly mated, the fifth drive input 1636e will share an axis of rotation with the fifth drive output 1724e to allow the transfer of rotational torque from the fifth drive output 1724e to the fifth drive input 1636e. A drive gear 3510 is rotatably mounted to the first end 1618a of the drive housing 1614 at the driven interface 1718. The drive gear 3510 may form part of or may otherwise be operatively coupled to the fifth drive input 1636e such that rotation of the fifth drive input 1636e via the fifth drive output 1724e rotates the drive gear 3510. The cylindrical lead screw 3502 includes a driven gear 3512 that intermeshes with the drive gear 3510 such that rotation of the drive gear 3510 correspondingly drives the driven gear 3512 and thereby rotates the cylindrical lead screw 3502 about the longitudinal axis $A_1$.

In some embodiments, as illustrated, the driven gear 3512 may comprise a ring gear defined on the outer surface of the cylindrical lead screw 3502. In other embodiments, however, the ring gear may alternatively be defined in the interior 3504 and the drive gear 3510 may be arranged to intermesh with the driven gear 3512 within the interior 3504, without departing from the scope of the disclosure.

In some embodiments, the cam profile(s) 3506 may be uniform (constant) along the axial length of the cylindrical lead screw 3502. In such embodiments, the cam profile(s) 3506 will be defined at a single common pitch (slope) between both ends of the cylindrical lead screw 3502. In other embodiments, however, the pitch of the cam profile(s) 3506 may vary along the axial length of the cylindrical lead screw 3502. For example, a first portion of the cam profile(s) 3506 may be defined at a first pitch, while a contiguous second portion of the cam profile(s) 3506 may be defined at a second pitch different from the first pitch. The second pitch may be more aggressive as compared to the first pitch, for instance. In such embodiments, without changing the angular velocity of the cylindrical lead screw 3502, the carriage 1626 will move faster in z-axis translation while traversing the second pitch as compared to traversing the first pitch. As will be appreciated, this may prove advantageous in allowing the operator to advance the end effector (FIG. 16) toward a surgical site faster along portions of the cylindrical lead screw 3502. More particularly, at the end of the insertion and/or retraction stroke, the profile(s) 3506 may be designed (defined) to mechanically slow down the speed of the carriage 1626 to prevent over travel damage as it approaches a hard stop. Moreover, at the end of the retraction stroke, the profile(s) 3506 may be designed (defined) to increase the speed of the carriage 1626 to reduce shaft reverse time. This will correspondingly increase the shaft insertion time when extending the shaft.

In the illustrated embodiment, the cylindrical lead screw 3502 is arranged within the shroud 1640 that extends between the first and second ends 1618a,b of the drive housing 1614. In at least one embodiment, however, the shroud 1640 may be omitted from the drive housing 1614. In other embodiments, the cylindrical lead screw 3502 and the shroud 1640 may comprise the same structure. In such embodiments, the cam profile(s) 3506 may be defined on the inner surface of the shroud 1640, and the shroud 1640 may rotate to facilitate z-axis translation of the carriage 1626, without departing from the scope of the disclosure.

While the cylindrical lead screw 3502 is described herein with reference to the cam profile(s) 3506 and follower pin(s) 3508, it is contemplated herein that the cylindrical lead screw 3502 may alternatively comprise a ball screw system, without departing from the scope of the disclosure. In such embodiments, the cylindrical lead screw 3502 may comprise a low friction, ball bearing filled lead screw system.

Fixed Roll Insertion Guide Structure

Figure 36A:
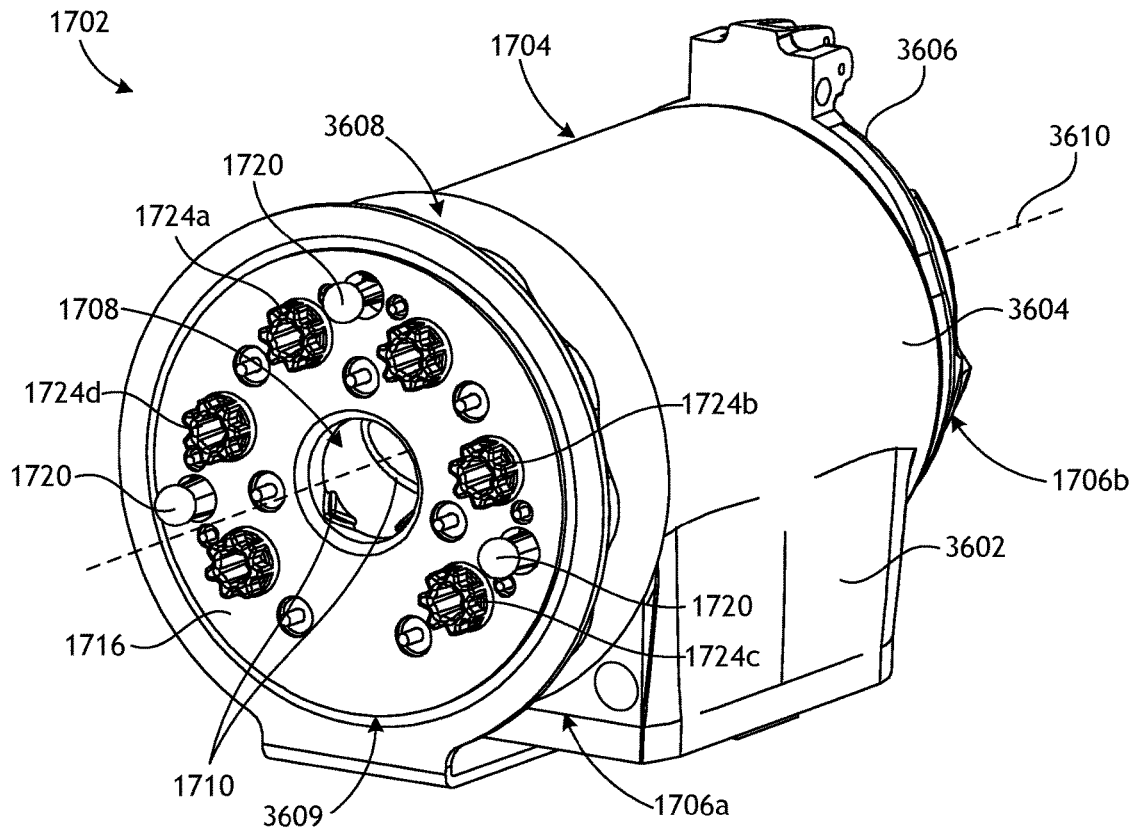
FIG. 36A is a perspective view of the instrument driver of FIGS. 17A and 17B.
Figure 36B:
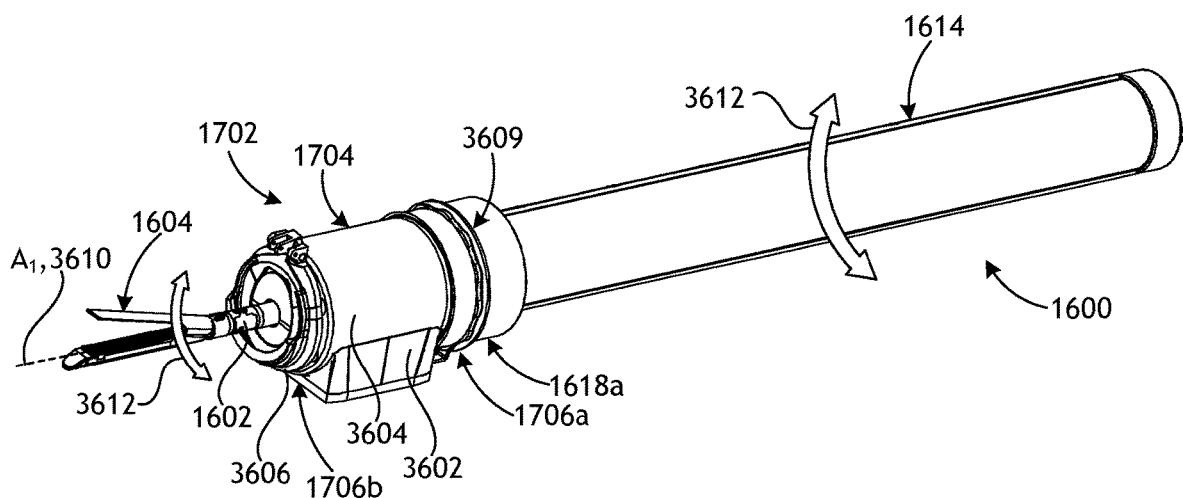
FIG. 36B is an isometric view of the surgical tool of FIG. 16 releasably coupled to the instrument driver, according to one or more embodiments.

FIG. 36A is a perspective view of the instrument driver 1702 of FIGS. 17A and 17B, and FIG. 36B is an isometric view of the surgical tool 1600 of FIG. 16 releasably coupled to the instrument driver 1702, according to one or more embodiments. As briefly discussed above, the instrument driver 1702 is configured to attach a surgical tool, such as the surgical tool 1600, to a surgical robotic arm (e.g., any of the robotic arms 104, 406 described herein). More specifically, the drive interface 1716 at the first end 1706a of the instrument driver 1702 is matable with the driven interface 1718 (FIG. 17B) provided at the first end 1618a of the drive housing 1614. The end effector 1604 and the shaft 1602 can penetrate the instrument driver 1702 by extending through the central aperture 1708 defined longitudinally through the body 1704 of the instrument driver 1702, and the alignment guides 1710 within the central aperture 1708 help angularly orient the surgical tool 1600 to the proper orientation relative to the instrument driver 1702.

In some embodiments, the drive housing 1614 may be mechanically coupled to the instrument driver 1702 by mating the interlocking features 1720 provided at the drive interface 1716 with the complementary-shaped pockets 1722 (FIG. 17B) provided on the driven interface 1718 (FIG. 17B) of the drive housing 1614. Moreover, the instrument driver 1702 includes the drive outputs 1724a-d that are matable with the drive inputs 1636a-d (FIG. 17B) of the drive housing 1614 such that, once properly mated, the drive inputs 1636a-d will share axes of rotation with the corresponding drive outputs 1724a-d to allow the transfer of rotational torque from the drive outputs 1724a-d to the corresponding drive inputs 1636a-d.

In the illustrated embodiment, the instrument driver 1702 includes a base 3602 that provides a location to removably mount the instrument driver 1702 to a surgical robotic arm of a surgical robotic system. As will be appreciated, the base 3602 may exhibit various geometries and sizes to properly mate with and mount to the robotic arm. Mechanical and electrical connections are provided from the robotic arm to the base 3602 and then to various mechanical and electrical components arranged within the instrument driver 1702 to manipulate and/or deliver power and/or signals from the robotic arm to the surgical tool 1600. Signals may include signals for pneumatic pressure, electrical power, electrical signals, and/or optical signals.

As illustrated, the body 1704 of the instrument driver 1702 provides an outer housing 3604 that can be fixedly attached to the base 3602. The outer housing 3604 extends generally between the first and second ends 1706a,b of the instrument driver 1702. In some embodiments, as illustrated, the outer housing 3604 can be generally cylindrical in shape. In other embodiments, however, the shape of the outer housing 3604 may vary depending on the application. The outer housing 3604 may be made of a variety of rigid materials including, but not limited to, metals, plastics, composite materials, or any combination thereof.

In some embodiments, the instrument driver 1702 may further include a sterile adapter 3606, 3608 that may be used to create a sterile boundary between the instrument driver 1702 and the surgical tool 1600. The sterile adapters 3606, 3608 comprise component parts located at opposing ends of the body 1704; the sterile adapter 3608 at the first end 1706a being referred as the "instrument sterile adapter," and the sterile adapted 3606 located at the second end 1706b being referred to as the "cannula sterile adapter." The sterile adapter 3606, 3608 may be configured to attach a surgical drape (not shown) to the instrument driver 1702 when the surgical tool 1600 is secured to the instrument driver 1702, and the surgical drape operates to separate the surgical tool 1600 and the patient from the instrument driver 1702 and the surgical robotics system. The sterile adapter 3606 may comprise two layers that essentially rotate along with the surgical tool 1600, and the surgical drape is positioned between the layers and does not roll with the sterile adapter 3606 and surgical tool 1600.

The drive interface 1716, the interlocking features 1720, and the drive outputs 1724a-d are all contained within or otherwise mounted to a tool drive assembly 3609 provided at the first end 1706a of the instrument driver 1702 and extending partially into the outer housing 3604. As described herein, the tool drive assembly 3609 is capable of rotating independent of the outer housing 3604 about a rotational axis 3610. When the surgical tool 1600 is mounted to the instrument driver 1702 at the tool drive assembly 3609, the longitudinal axis $A_1$ of the surgical tool 1600 coaxially aligns with the rotational axis 3610 of the tool drive assembly 3609. According to embodiments of the present disclosure, the tool drive assembly 3609 may be actuated to rotate and thereby correspondingly rotate or "roll" the entire surgical tool 1600 about its longitudinal axis $A_1$, as indicated by the arrows 3612 (FIG. 36B). Consequently, actuation of the tool drive assembly 3609 allows the entire surgical tool 1600, including the shaft 1602, the end effector 1604, and the drive housing 1614, to continuously roll about the longitudinal axis $A_1$ in either angular direction (i.e., clockwise or counter-clockwise) relative to the base 3602 and the outer housing 3604, which remain stationary. In contrast to other surgical tools where the shaft and the end effector are rotated independent of and relative to the remaining portions of the surgical tool, the shaft 1602, the end effector 1604, and the drive housing 1614 are fixed in rotation, which enables the entire surgical tool 1600 to rotate as a single, monolithic unit.

Figure 37A:
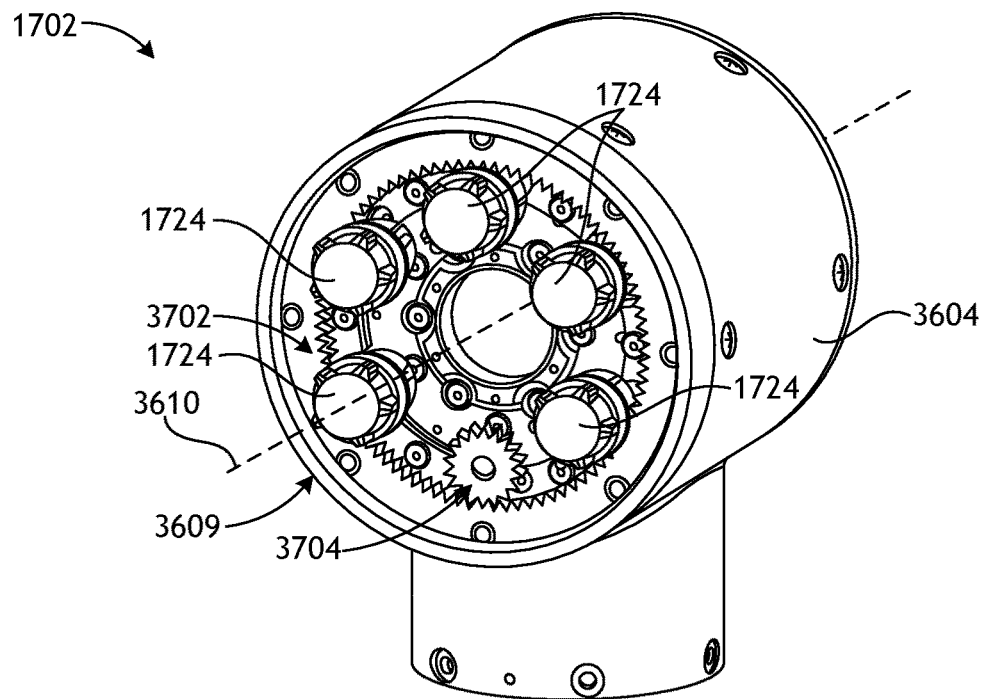
FIG. 37A is a schematic diagram of an example embodiment of the instrument driver of FIGS. 36A-36B, according to one or more embodiments.

FIG. 37A is a schematic diagram of an example embodiment of the instrument driver 1702 of FIGS. 36A-36B, according to one or more embodiments. Unlike the instrument driver 1702 depicted in FIGS. 36A-36B, the instrument driver 1702 of FIG. 37A includes five drive outputs 1724. Moreover, the drive interface 1716 (FIG. 36A) is omitted in FIG. 37A to enable viewing of the internal components of the tool drive assembly 3609 and its roll mechanism. As illustrated, the roll mechanism includes a stator gear 3702 and a rotor gear 3704 matable with the stator gear 3702, and each of the gears 3702, 3704 is positioned behind the drive interface 1716 (not shown). Actuation of the tool drive assembly 3609 causes the rotor gear 3704 to drive the stator gear 3702 and thereby continuously rotate or "roll" the tool drive assembly 3609 about the rotational axis 3610 in either angular direction.

More specifically, as illustrated, the stator gear 3702 may comprise a ring gear that defines gear teeth along an inner circumference, and the rotor gear 3704 is may comprise a circular gear positioned within the inner circumference of the stator gear 3702 and defining gear teeth along an outer circumference. The gear teeth of the stator gear 3702 have the same pitch as the gear teeth of the rotor gear 3704 such that the gear teeth are matable. Both gears 3702, 3704 may be made of a rigid material, such as a metal or a hard plastic.

The stator gear 3702 is fixedly attached to the tool drive assembly 3609, and the rotor gear 3704 is actuatable (rotatable) to induce rotation of the stator gear 3702, which, in turn, correspondingly rotates the tool drive assembly 3609, including the drive interface 1716 (FIG. 36A), the interlocking features 1720 (FIG. 36A), and the drive outputs 1724a-d (FIG. 36A). More particularly, the rotor gear 3704 is coupled to a drive mechanism (e.g., a motor) housed within the outer housing 3604 that causes the rotor gear 3704 to rotate in clockwise or counter-clockwise directions, as desired. The drive mechanism may receive signals from an integrated controller also arranged within the outer housing 3604. As the drive mechanism causes the rotor gear 3704 to rotate, the rotor gear 3704 travels along the gear teeth of the stator gear 3702, thereby causing the tool drive assembly 3609 to rotate. In this configuration, the rotor gear 3704 is capable of continuously rotating in either direction and thus allows the tool drive assembly 3609 to achieve infinite roll about the rotational axis 3610, and thereby simultaneously causing the surgical tool 1600 (FIG. 36B) to rotate or "roll".

Figure 37B:
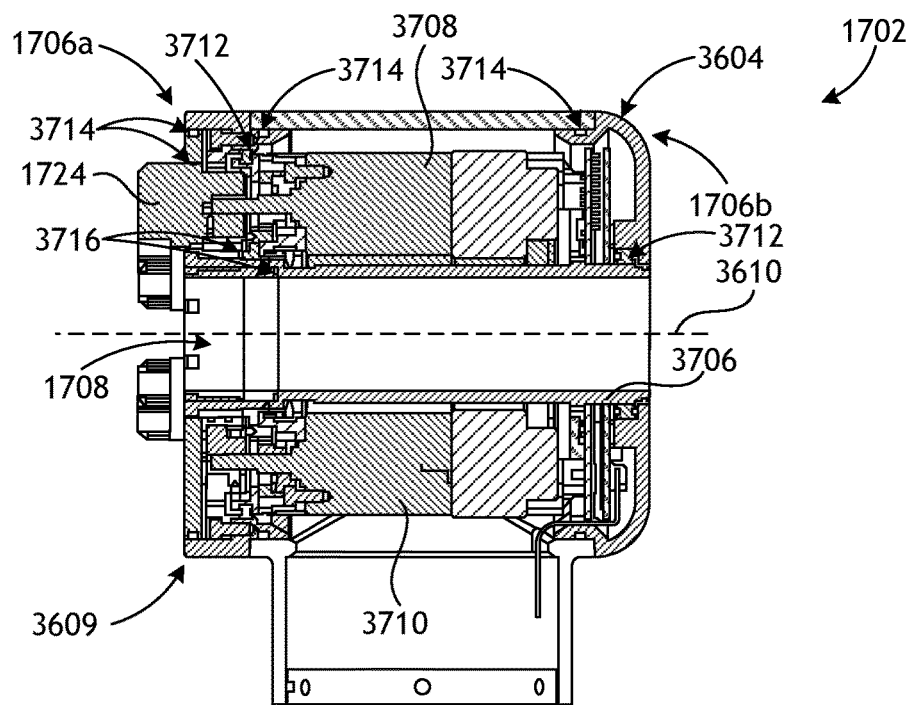
FIG. 37B is a cross-sectional view of the instrument driver of FIG. 37A, according to one or more embodiments.

FIG. 37B is a cross-sectional side view of the tool driver 1702 of FIG. 37A, according to one or more embodiments. As illustrated, the tool drive assembly 3609 is operatively coupled to or otherwise defines an inner conduit 3706 that defines the central aperture 1708 such that rotation of the tool drive assembly 3609 simultaneously rotates the inner conduit 3706 about the rotational axis 3610 in the same direction. As described above, the central aperture 1708 receives the shaft 1602 (FIG. 36B) of the surgical tool 16 (FIG. 36B). This configuration allows the surgical tool 1600 to be continuously rotated or rolled about the rotational axis 3610 in either direction with minimal or no restrictions. One or more actuators 3708 (one shown), alternately referred to as "motor stacks", are arranged about the inner conduit 3706 and rotatable therewith as the tool drive assembly 3609 rotates. The actuators 3708 are designed to drive the rotation of the drive outputs 1724. The tool drive assembly 3609 may further include a drive motor 3710 configured to drive the rotation of the tool drive assembly 3609 within the outer housing 3604.

The tool drive assembly 3609 may further provide or otherwise include a plurality of bearings 3712. Each bearing 3712 comprises a mechanical component configured to reduce friction between adjacent moving parts and facilitate rotation around the rotational axis 3610. More specifically the bearings 3712 allow the tool drive assembly 3609 to rotate about the rotational axis 3610 relative to the outer housing 3604, which remains generally stationary. One bearing 3712 alone is capable of supporting the radial or torsional loading as the tool drive assembly 3609 rotates within the outer housing 3604. In the illustrated embodiment, the instrument driver 1702 includes at least two bearings 3712 fixedly attached to the tool drive assembly 3609 such that a plurality of components (such as balls or cylinders) within the bearings 3712 contact the outer housing 3604. One of the bearings 3712 is arranged at or near the first end 1706a of the instrument driver 1702 and the other bearing 3712 is arranged at or near the second end 1706b. This configuration improves rigidity and support between the first end and the second ends of the tool drive assembly 3609 as the tool drive assembly 3609 rotates within the outer housing 3604. Alternate embodiments may include additional bearings that provide additional support along the length of the tool drive assembly 3609, such as along the length of the inner conduit 3706.

The tool drive assembly 3609 may also include a plurality of seals 3714 and gaskets 3716 configured to seal various surface interfaces to prevent fluids from entering the outer housing at the given interface. The seals 3714, for example, may be arranged at various radial interfaces between the outer housing 3604 and the tool drive assembly 3609, and the gaskets 3716 may be arranged at various axial interfaces between the outer housing 3604 and the tool drive assembly 3609. The seals 3714 and the gaskets 3716 may be made of strong elastomeric materials (e.g., rubber). In some embodiments, one or more of the seals 3714 may comprise O-rings, for example, but may alternatively comprise any other suitable type of sealing element. As will be appreciated, this configuration and placement of the seals 3714 and gaskets 3716 helps to maintain sterility of the components within the instrument driver 1702 during a surgical procedure.

Figure 37C:
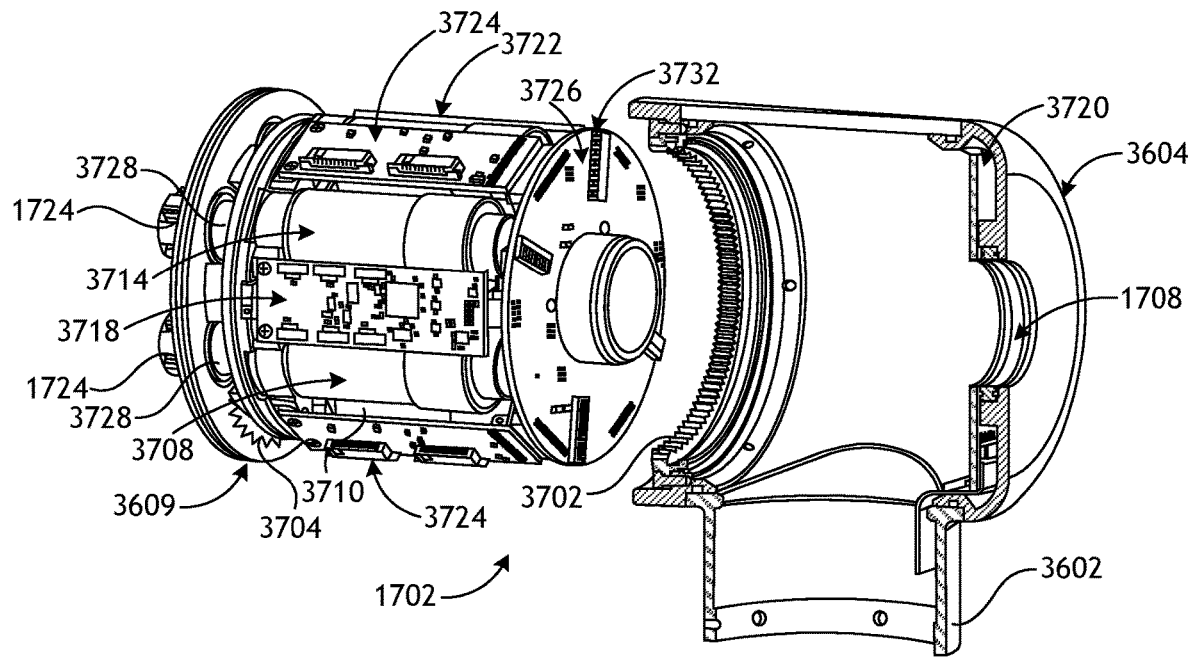
FIG. 37C illustrates a partially exploded, perspective view of the internal mechanical and electrical components of the instrument driver of FIG. 37A, according to one or more embodiments.

FIG. 37C illustrates a partially exploded, perspective view of the internal mechanical and electrical components of the instrument driver 1702, according to one or more embodiments. The internal mechanical and electrical components of the instrument driver 1702 include a plurality of the actuators 3708, the drive motor 3710 (partially visible), a torque sensor (not shown), a torque sensor amplifier 3718, a slip ring 3720, a plurality of encoder boards 3722, a plurality of motor power boards 3724, and an integrated controller 3726.

Each actuator 3708 may be coupled to a corresponding drive output 1724 via a drive shaft 3728. In the illustrated embodiment, the instrument driver 1702 includes five drive outputs 1724 and thus five actuators 3708. The drive shaft 3728 may be a keyed shaft such that it includes a plurality of grooves to allow the drive shaft 3728 to securely mate to a corresponding drive output 1724. The actuator 3708 causes the drive shaft 3728 to rotate in a clockwise or counter-clockwise direction, thereby causing the respective drive output 1724 to similarly rotate. In some embodiments, the drive shaft 3728 may be torsionally rigid but spring compliant, thus allowing the drive shaft 3728 and the corresponding drive output 1724 to rotate and also axially retract and protract within the tool drive assembly 3609. Each actuator 3708 may receive electrical signals from the integrated controller 3726 indicating the direction and amount to rotate the drive shaft 3728.

The drive motor 3710 is configured to drive the rotation of the tool drive assembly 3609 within the outer housing 3604. The drive motor 3710 may be structurally equivalent to one of the actuators 3708, except that it is operatively coupled to the rotor gear 3704 and designed to drive the stator gear 3702 and thereby rotate the tool drive assembly 3609 relative to the outer housing 3604, as generally described above. The drive motor 3710 causes the rotor gear 3704 to rotate in a clockwise or counter-clockwise direction, thereby causing the rotor gear 3704 to travel about the gear teeth of the stator gear 3702. This configuration allows the tool drive assembly 3609 to continuously roll or rotate without being hindered by potential wind-up of cables or pull-wires. The drive motor 3710 may receive electrical signals from the integrated controller 3726 indicating the direction and amount to rotate the rotor gear 3704.

The torque sensor measures the amount of torque produced on the rotating tool drive assembly 3609. In some embodiments, the torque sensor may be capable of measuring torque in both clockwise and counter-clockwise directions. The torque sensor amplifier 3718 comprises circuitry for amplifying the signal that measures the amount of torque produced on the rotating tool drive assembly 3609. In some embodiments, the torque sensor is mounted to the drive motor 3710.

Figure 37D:
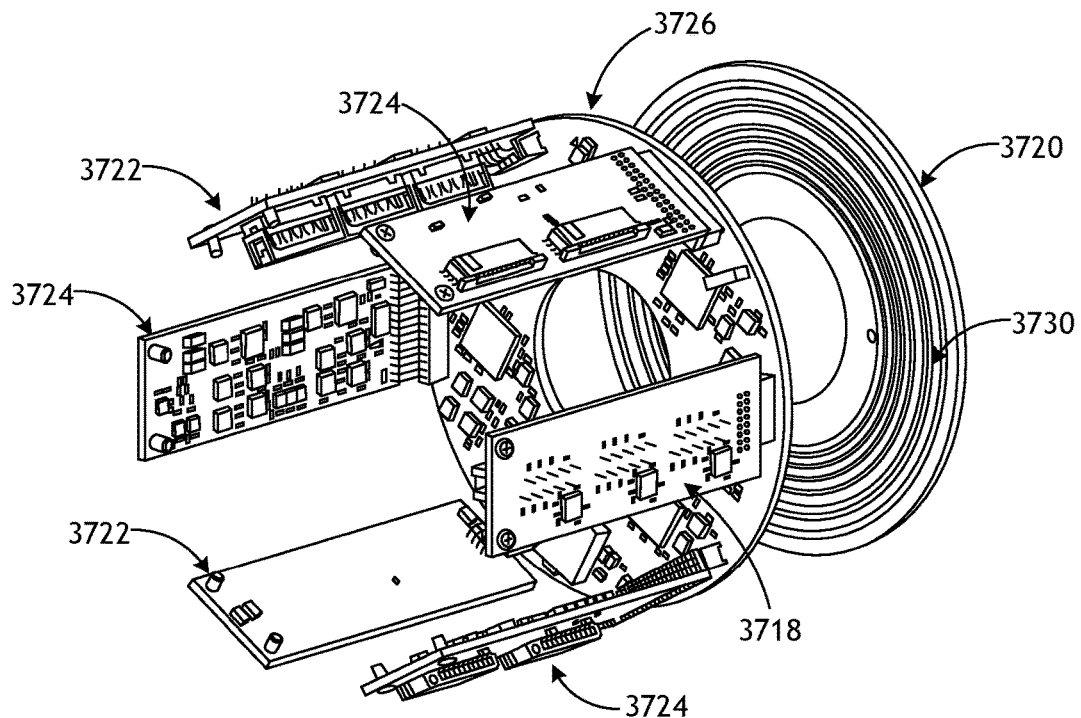
FIG. 37D is a partially exploded, perspective view of the internal electrical components of the instrument driver of FIG. 37A, according to one or more embodiments.

Referring to FIG. 37D, with continued reference to FIG. 37C, illustrated is a partially exploded, perspective view of the internal electrical components of the instrument driver 1702, according to one or more embodiments. The slip ring 3720 facilitates the transfer of electrical power and signals from a stationary structure to a rotating structure. More specifically, in the illustrated embodiment, the slip ring 3720 is structured as a ring including a central hole that is configured to align with the central aperture 1708 of the tool drive assembly 3609. A first side of the slip ring 3720 includes a plurality of concentric grooves 3730 while a second, opposite side of the slip ring 3720 includes a plurality of electrical components for the electrical connections provided from the robotic arm and the base 3602.

The slip ring 3720 is secured to the outer housing 3604 at a specific distance from portions of the tool drive assembly 3609 to allocate space for electrical connections and interaction. The plurality of concentric grooves 3730 are configured to mate with a plurality of brushes 3732 attached to the integrated controller 3726, which operates as the computing device within the tool drive assembly 3609. Contact between the grooves 3730 and the brushes 3732 enables the transfer of electrical power and signals from the robotic arm to the slip ring 3720, and from the slip ring 3720 to the integrated controller 3726. As a result of the received signals, the integrated controller 3726 is then configured to send various signals to respective components within the tool drive assembly 3609 to cause operation of the surgical tool 1600 (FIG. 36B).

The plurality of encoder boards 3722 read and process the signals received through the slip ring 3720 from the surgical robotic system. Signals received from the surgical robotic system may include signals indicating the amount and direction of rotation of the surgical tool 1600 (FIG. 36B), signals indicating the amount and direction of rotation of the end effector 1604 (FIG. 36B), signals operating a light source on the surgical tool 1600, signals operating a video or imaging device on the surgical tool 1600, and other signals designed to operate various functionalities of the surgical tool 1600. The configuration of the encoder boards 3722 allows the entire signal processing to be performed completely in the tool drive assembly 3609. The plurality of motor power boards 3724 each comprises circuitry for providing power to the actuators 3708. In some embodiments, the functions of the encoder boards 3722 and the integrated controller 3726 may be distributed in a different manner than is described here, such that the encoder boards 3722 and the integrated controller 3726 may perform the same functions or some combination thereof.

In the illustrated embodiment, the tool drive assembly 3609 includes two encoder boards 3722, the torque sensor amplifier 3718, and three motor power boards 3724. These components are secured to the integrated controller 3726 and extend perpendicularly from the integrated controller 3726. This configuration provides room for the actuators 3708 and the drive motor 3710 to be positioned within the confines of the tool drive assembly 3609.

Figure 38:
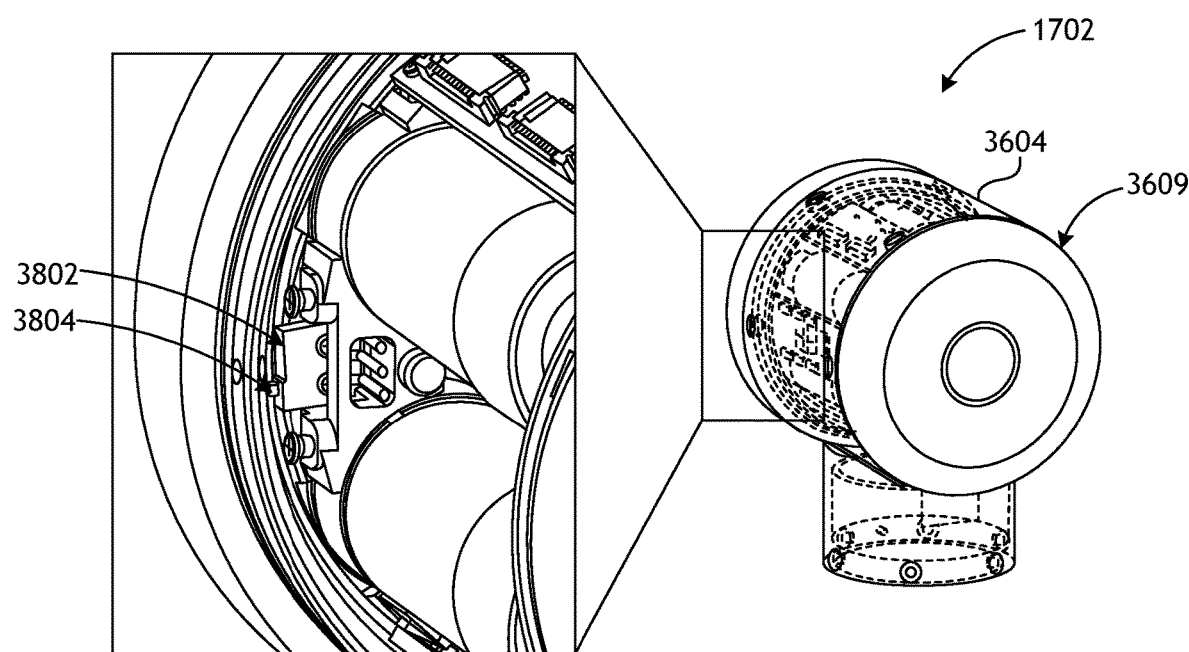
FIG. 38 is a zoomed-in, perspective view of various electrical components of the instrument driver of FIG. 37A, according to one or more embodiments.

FIG. 38 is a zoomed-in, perspective view of various electrical components of the instrument driver 1702, according to one or more embodiments. More specifically, the enlarged, zoomed-in view depicts component parts that facilitate roll indexing of the tool drive assembly 3609. Roll indexing monitors the angular position of the tool drive assembly 3609 relative to the outer housing 3604 such that the position and angular orientation of the surgical tool 1600 (FIG. 36B) may be known in real-time by the surgical robotics system. As illustrated, the roll indexing mechanism includes a micro switch 3802 and one or more bosses 3804 (one shown). The micro switch 3802 may be arranged on the tool drive assembly 3609, and the boss(es) 3804 may be positioned on the outer housing 3604 and configured to contact the micro switch 3802 as the tool drive assembly 3609 rotates and brings the micro switch into proximity of the boss(es) 3804. Once contact between the micro switch 3802 and the boss(es) 3804 occurs, the micro switch 3802 is activated and records the time and angular orientation of the tool drive assembly 3806. Each boss 3804 serves as a single reference point for the micro switch 3802 about the inner circumference of the outer housing 3604.

In other embodiments, the instrument driver 1702 may include other means to determine rotational position, such as through the use of a dedicated servo operatively coupled to the rotational drive motor 3710 (FIGS. 37B-37C). Alternatively, absolute rotational position could be determined by using an annular ring encoder, as generally known by those skilled in the art.

Robotic Instrument with Torsion Cable Drives for Carriage-Based Architecture

Figure 39A:
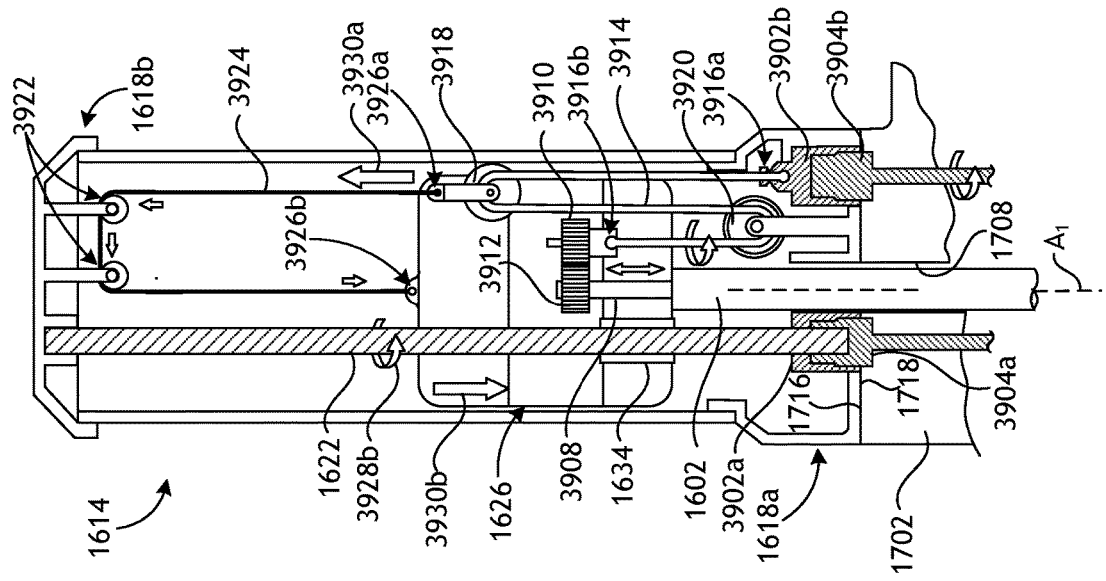
FIGS. 39A and 39B are partial cross-sectional side views of another example of the handle of FIG. 16, according to one or more additional embodiments.
Figure 39B:
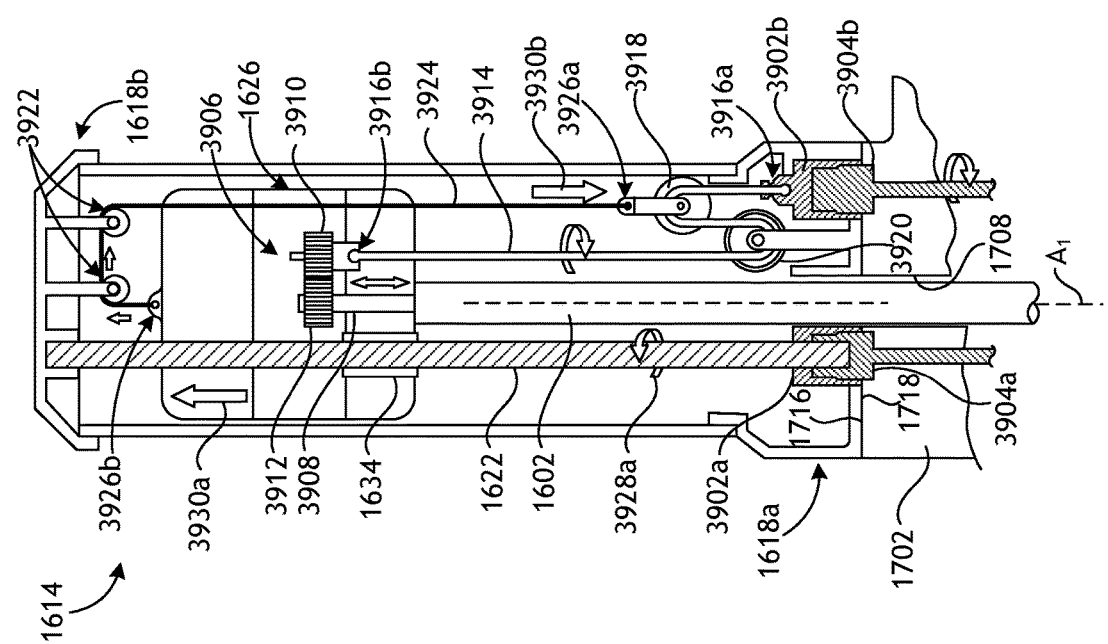

FIGS. 39A and 39B are partial cross-sectional side views of another example of the drive housing 1614 of FIG. 16, according to one or more additional embodiments. As illustrated, the drive housing 1614 includes the first and second ends 1618a,b, and the instrument driver 1702 can be removably coupled to the drive housing 1614 at the first end 1618a. The lead screw 1622 extends longitudinally between the first and second ends 1618a,b, and the carriage 1626 is movably mounted to the lead screw 1622 at the carriage nut 1634 to allow the carriage 1626 to traverse the lead screw 1622 along the longitudinal axis $A_1$. The shaft 1602 extends distally from the carriage 1626 through the first end 1618a of the drive housing 1614 and subsequently through the central aperture 1708 of the instrument driver 1702 (when mounted). The drive housing 1614 may be releasably coupled to the instrument driver 1702 by extending the shaft 1602 through the central aperture 1708 and mating the drive interface 1716 of the instrument driver 1702 to the driven interface 1718 of the drive housing 1614, as generally described above.

In the illustrated embodiment, the driven interface 1718 of the drive housing 1614 includes a first drive input 3902a and a second drive input 3902b, and the drive interface 1716 includes a first drive output 3904a and a second drive output 3904b. The drive inputs 3902a,b may be substantially similar to the drive inputs 1636a-d of FIGS. 16 and 17B, and the drive outputs 3904a,b may be substantially similar to the drive outputs 1724a-d of FIG. 17B. Accordingly, the drive inputs 3902a,b may be matable with the drive outputs 3904a,b such that movement (rotation) of a given drive output 3904a,b correspondingly moves (rotates) the associated drive input 3902a,b. While only two drive inputs 3902a,b and two drive outputs 3904a,b are depicted, more or less than two may be included in the drive housing 1614, without departing from the scope of the disclosure.

The first drive input 3902a is operatively coupled to the lead screw 1622 such that rotation of the first drive input 3902a (via rotation of the first drive output 3904a) correspondingly rotates the lead screw 1622 in the same angular direction. As the lead screw 1622 rotates, the carriage nut 1634 is urged to axially traverse the lead screw 1622 and simultaneously advance or retract the carriage 1626 along the longitudinal axis $A_1$, depending on the rotational direction of the lead screw 1622. Moreover, as the carriage 1626 advances or retracts, the shaft 1602 and the end effector 1604 (FIGS. 16 and 17A-17B) arranged at the distal end of the shaft 1602 correspondingly moves distally or proximally (i.e., z-axis translation).

In the illustrated embodiment, an activating mechanism 3906 is housed in or otherwise forms part of the carriage 1626, and the second drive input 3902b is operatively coupled to the activating mechanism 3906 such that rotation of the second drive input 3902b (via rotation of the second drive output 3904b) causes the activating mechanism 3906 to actuate (operate). The activating mechanism 3906 may be similar to any of the activating mechanisms 1638a-c described herein with reference to FIG. 16 and other figures. Accordingly, the activating mechanism 3906 may be operable to carry out one or more functions of the end effector 1604 (FIGS. 16 and 17A-17B), such as opening or closing the jaws 1610, 1612 (FIGS. 16 and 17A-17B), articulating the end effector 1604 at the wrist 1606 (FIG. 16), or advancing or retracting the knife 2702 (FIG. 27) at the end effector 1604. In the illustrated embodiment, actuating the activating mechanism 3906 may cause a firing rod 3908 (similar to the firing rod 2506 of FIGS. 25 and 26) to move along the longitudinal axis $A_1$ and correspondingly move the knife 2702 in the same direction, thus causing the knife 2702 to "fire".

As illustrated, the activating mechanism 3906 may include a drive gear 3910 rotatably mounted to the carriage 1626 and configured to drive a driven gear 3912 also rotatably mounted to the carriage 1626. The drive and driven gears 3910, 3912 may each define gear teeth and, in some embodiments, the drive gear 3910 may be positioned to directly intermesh with the driven gear 3912. In other embodiments, however, one or more idler gears (not shown) may interpose the drive gear 3910 and the driven gear 3912 and may otherwise transfer torque from the drive gear 3910 to the driven gear 3912 via an intermeshed gearing arrangement. The driven gear 3912 may be operatively coupled to the firing rod 3908 such that rotation of the driven gear 3912 (via rotation of the drive gear 3912) causes the firing rod 3908 to translate along the longitudinal axis $A_1$ and thereby cause an associated cutting element or knife to fire.

In order to transmit torsional (rotational) forces or loading from the second drive input 3902b to the activating mechanism 3906 and, more particularly, to the drive gear 3910, the drive housing 1614 may further include a torsion cable 3914 that extends between the second drive input 3902b and the drive gear 3910. The torsion cable 3914 may comprise a flexible wire or filament having a first end 3916a coupled to the second drive input 3902b and a second end 3916b coupled to the drive gear 3910. The torsion cable 3914 may be capable of transmitting torsional loads from the first end 3916a, as driven by rotation (actuation) of the second drive input 3902b, to the second end 3916b and thereby cause the drive gear 3910 to rotate.

A basic example of the torsion cable 3914 is the type of cable traditionally used in vehicle speedometer or tachometer systems; a cable that is flexible, but strong enough to transmit torque from one end to the opposite end even when extending in a non-linear path. The torsion cable 3914 may be made of a variety of materials including, but not limited to, stainless steel and tungsten.

The torsion cable 3914 has a fixed length, and to allow torque to be transmitted between the first and second ends 1916a,b, the torsion cable 3914 must be maintained in constant tension during operation. To accomplish this, the drive housing 1614 may further include a constant tension or tensioning system that includes a tension pulley 3918, a stationary pulley 3920, one or more carriage pulleys 3922, and a carriage cable 3924. As illustrated, the stationary pulley 3920 is coupled or anchored to the drive housing 1614 at or near the first end 1618a, and the torsion cable 3914 is routed through the tension and stationary pulleys 3918, 3920 in the general path/shape of an "S" curve. More specifically, the torsion cable 3914 is coupled to and extends from the second drive input 3902b and is routed around the tension pulley 3918 to extend toward the stationary pulley 3920. The torsion cable 3914 is then routed around the stationary pulley 3920 and extends to the drive gear 3910 where it is fixed. Any torsional loading assumed by the torsion cable 3914 at the first end 3916a, via rotation (actuation) of the second drive input 3902b, will be transmitted to the second end 3916b of the torsion cable 3914 through the tension and stationary pulleys 3918, 3920 to rotate the drive gear 3910 and thereby cause the activating mechanism 3906 to actuate (operate); e.g., to perform various instrument specific functions, such as knife firing, jaw opening and closing, energy activation, wristed motions, etc.

The tension pulley 3918 is suspended within the drive housing 1614 on the carriage cable 3924 to help maintain constant tension in the torsion cable 3914 during operation. More specifically, the carriage cable 3924 has a first end 3926a coupled to the tension pulley 3918 and a second end 3926b coupled to the carriage 1626. The carriage cable 3924 is routed through the carriage pulley(s) 3922, which may be coupled or anchored to the drive housing 1614, such as at or near the second end 1618b. In the illustrated embodiment, there are two carriage pulleys 3922, but there could alternatively be more or less than two carriage pulleys 3922, without departing from the scope of the disclosure. Because the second end 3916b of the torsion cable 3914 is coupled to and travels with the carriage 1626, extending the carriage cable 3914 between the carriage 1626 and the tension pulley 3918 forces the tension pulley 3918 and the carriage 1626 to move in opposite axial directions while simultaneously helping to maintain tension in the torsion cable 3914 during operation.

Example operation of the drive housing 1614 is now described with continued reference to FIGS. 39A-39B. In FIG. 39A, the lead screw 1622 is rotated in a first angular direction 3928a (via operation of the first drive input 3902a), which causes the carriage 1626 to move proximally, as indicated by the arrow 3930a. As the carriage 1626 moves proximally 3930a, the carriage cable 3924 is fed (routed) through the carriage pulley(s) 3922 and allows the tension pulley 3918 to descend distally, as indicated by the arrow 3930b. Since the second end 3916b of the torsion cable 3914 is coupled to the carriage 1626, the torsion cable 3914 is fed (routed) through the tension and stationary pulleys 3918, 3920 as the carriage 1626 moves proximally 3930a, and the tension pulley 3918 helps maintain the torsion cable 3914 in constant tension as it moves distally 3930b. Accordingly, constant tension is maintained in the torsion cable 3914 while the carriage 1626 moves proximally 3930a or while it remains stationary. Consequently, the activating mechanism 3906 may be operated at all times during operation of the drive housing 1614, such as when the carriage 1626 moves or is idle. In some embodiments, a channel or slot (not shown) may be defined within a sidewall or other portion of the drive housing 1614 to help guide the translational direction of the tension pulley 3918. In addition, a lite tension spring could be added to assist movement of the tension pulley 3918.

Similarly, in FIG. 39B, the lead screw 1622 is rotated in a second angular direction 3928b (via operation of the first drive input 3902a), opposite the first angular direction 3928a (FIG. 39A), which causes the carriage 1626 to move distally 3930b. As the carriage 1626 moves distally 3930b, the carriage cable 3924 is fed (routed) through the carriage pulley(s) 3922 and allows the tension pulley 3918 to ascend proximally 3930a. Since the second end 3916b of the torsion cable 3914 is coupled to the carriage 1626, the torsion cable 3914 is fed (routed) through the tension and stationary pulleys 3918, 3920 as the carriage 1626 moves distally 3930b, and the tension pulley 3918 helps maintain the torsion cable 3914 in constant tension as it moves proximally 3930a. Accordingly, constant tension is maintained in the torsion cable 3914 while the carriage 1626 moves distally 3930b or while it remains stationary. Moreover, as mentioned above, a channel or slot (not shown) may be defined within a sidewall or other portion of the drive housing 1614 to help guide the translational direction of the tension pulley 3918.

Figure 40B:
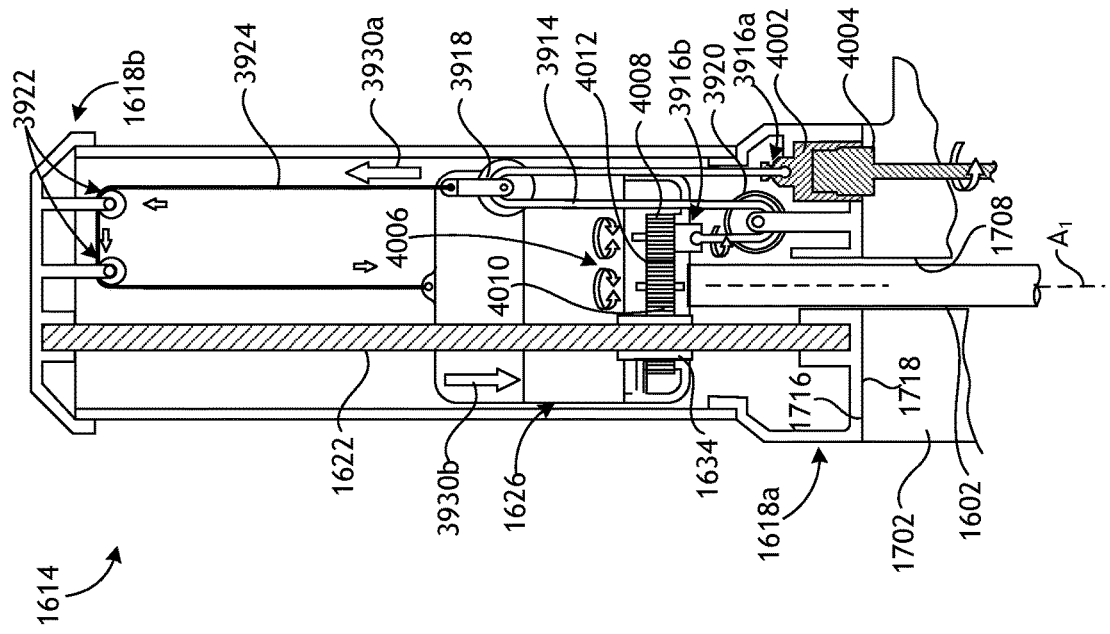
FIGS. 40A and 40B are partial cross-sectional side views of another example of the handle of FIG. 16, according to one or more additional embodiments.
Figure 40A:
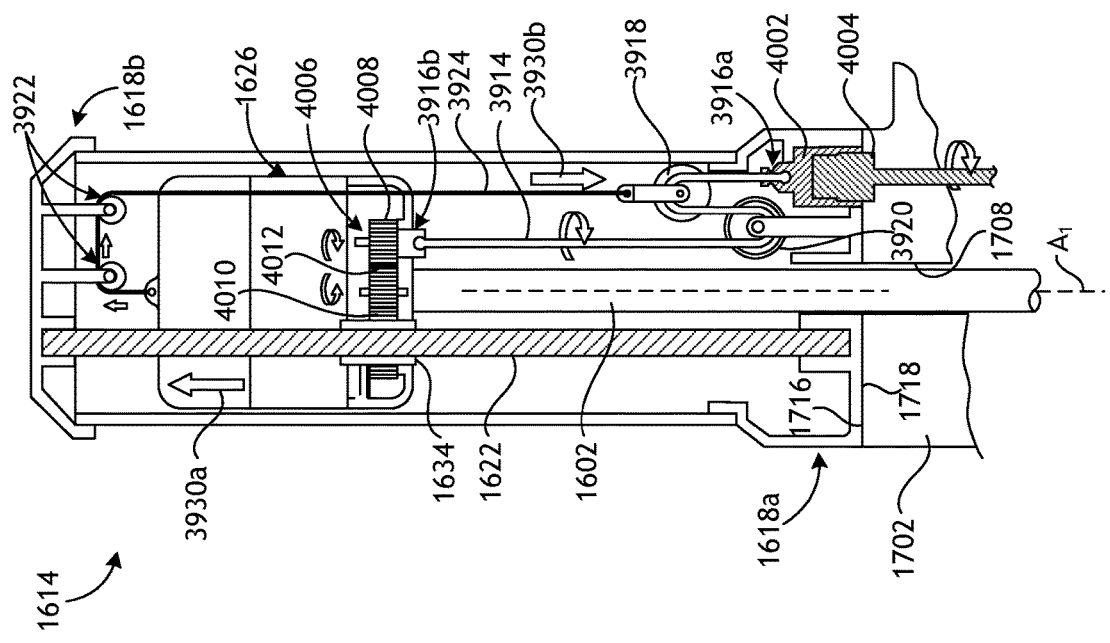

FIGS. 40A and 40B are partial cross-sectional side views of another example of the drive housing 1614 of FIG. 16, according to one or more additional embodiments. The drive housing 1614 of FIGS. 40A-40B is similar in some respects to the embodiment of the drive housing 1614 depicted in FIGS. 39A-39B and therefore may be best understood with reference thereto, where like numerals will correspond to similar components not described again. As illustrated, the drive housing 1614 includes the first and second ends 1618a,b, and the instrument driver 1702 can be removably coupled to the drive housing 1614 at the first end 1618a. The lead screw 1622 extends longitudinally between the first and second ends 1618a,b, and the carriage 1626 is movably mounted to the lead screw 1622 at the carriage nut 1634 to allow the carriage 1626 to traverse the lead screw 1622 along the longitudinal axis $A_1$. The shaft 1602 extends distally from the carriage 1626 through the first end 1618a of the drive housing 1614 and subsequently through the central aperture 1708 of the instrument driver 1702 (when mounted). The drive housing 1614 may be releasably coupled to the instrument driver 1702 by extending the shaft 1602 through the central aperture 1708 and mating the drive interface 1716 of the instrument driver 1702 to the driven interface 1718 of the drive housing 1614, as generally described above.

In the illustrated embodiment, the driven interface 1718 of the drive housing 1614 includes a drive input 4002 and the drive interface 1716 includes a drive output 4004. The drive input 4002 may be substantially similar to the drive inputs 1636a-d of FIGS. 16 and 17B, and the drive output 4004 may be substantially similar to the drive outputs 1724a-d of FIG. 17B. Accordingly, the drive input 4002 may be matable with the drive output 4004 such that movement (rotation) of the drive output 4004 correspondingly moves (rotates) the associated drive input 4002.

In the illustrated embodiment, an activating mechanism 4006 is housed in or otherwise forms part of the carriage 1626, and the drive input 4002 is operatively coupled to the activating mechanism 4006 such that rotation of the drive input 4002 (via rotation of the drive output 4004) causes the activating mechanism 4006 to actuate (operate). While the activating mechanism 4006 may be similar to any of the activating mechanisms 1638a-c described herein with reference to FIG. 16 and other figures, in the illustrated embodiment, the activating mechanism 4006 is configured to rotate the lead screw 1622 and thereby cause axial translation of the carriage 1626 along the longitudinal axis $A_1$.

More specifically, the activating mechanism 4006 includes a drive gear 4008 rotatably mounted to the carriage 1626 and configured to drive a driven gear 4010 also rotatably mounted to the carriage 1626. In some embodiments, the drive gear 4008 may be positioned to directly intermesh with the driven gear 4010. In other embodiments, however, one or more idler gears 4012 (one shown) may interpose the drive gear 4008 and the driven gear 4010 and may otherwise transfer torque from the drive gear 4008 to the driven gear 4010 via an intermeshed gearing arrangement. In some embodiments, the driven gear 4010 forms part of or is otherwise defined on the outer circumference of the carriage nut 1634 such that rotation of the driven gear 4010 correspondingly rotates the carriage nut 1634 relative to the lead screw 1622, which remains stationary. As the carriage nut 1634 rotates, the carriage 1626 is urged to move axially along the longitudinal axis $A_1$, depending on the rotational direction of the carriage nut 1634.

In order to transmit torsional (rotational) forces or loading from the drive input 4002 to the activating mechanism 4006 and, more particularly, to the drive gear 4008, the torsion cable 3914 extends between the drive input 4002 and the drive gear 4008. Moreover, the torsion cable 3914 is maintained in constant tension with the tensioning system described above with reference to FIGS. 39A-39B. More specifically, the torsion cable 3914 is coupled to and extends from the drive input 4002 and is routed around the tension pulley 3918 to extend toward the stationary pulley 3920. The torsion cable 3914 is then routed around the stationary pulley 3920 and extends to the drive gear 4008 where it is fixed. Any torsional loading assumed by the torsion cable 3914 at its first end 3916a, via rotation (actuation) of the drive input 4002, will be transmitted to its second end 3916b through the tension and stationary pulleys 3918, 3920 to rotate the drive gear 4008 and thereby cause the activating mechanism 4006 to actuate (operate).

Moreover, the tension pulley 3918 is again suspended within the drive housing 1614 on the carriage cable 3924 to help maintain constant tension in the torsion cable 3914 during operation. More specifically, the carriage cable 3924 extends from the tension pulley 3918, through the carriage pulley(s) 3922, and to the carriage 1626. Because the second end 3916b of the torsion cable 3914 is coupled to and travels with the carriage 1626, extending the carriage cable 3914 between the carriage 1626 and the tension pulley 3918 forces the tension pulley 3918 and the carriage 1626 to move in opposite axial directions while simultaneously helping to maintain tension in the torsion cable 3914 during operation.

Example operation of the drive housing 1614 is now described with continued reference to FIGS. 40A-40B. In FIG. 40A, the torsion cable 3914 is rotated in a first angular direction (via operation of the drive input 4002), which causes the drive gear 4008 to rotate and thereby rotate the driven gear 4010. Rotating the driven gear 4010 correspondingly rotates the carriage nut 1634 relative to the stationary lead screw 1622, which urges the carriage 1626 to move proximally 3930a along the lead screw 1622. As the carriage 1626 moves proximally 3930a, the carriage cable 3924 is fed (routed) through the carriage pulley(s) 3922 and allows the tension pulley 3918 to descend distally 3930b. Since the second end 3916b of the torsion cable 3914 is coupled to the carriage 1626, the torsion cable 3914 is fed (routed) through the tension and stationary pulleys 3918, 3920 as the carriage 1626 moves proximally 3930a, and the tension pulley 3918 helps maintain the torsion cable 3914 in constant tension as it moves distally 3930b.

Similarly, in FIG. 40B, the torsion cable 3914 is rotated in a second angular direction (via operation of the drive input 4002) opposite the first angular direction, which causes the drive gear 4008 to rotate and thereby rotate the driven gear 4010. Rotating the driven gear 4010 correspondingly rotates the carriage nut 1634 relative to the stationary lead screw 1622, which urges the carriage 1626 to move distally 3930b along the lead screw 1622. As the carriage 1626 moves distally 3930b, the carriage cable 3924 is fed (routed) through the carriage pulley(s) 3922 and allows the tension pulley 3918 to ascend proximally 3930a. Since the second end 3916b of the torsion cable 3914 is coupled to the carriage 1626, the torsion cable 3914 is fed (routed) through the tension and stationary pulleys 3918, 3920 as the carriage 1626 moves distally 3930b, and the tension pulley 3918 helps maintain the torsion cable 3914 in constant tension as it moves proximally 3930a.

Figure 40C:
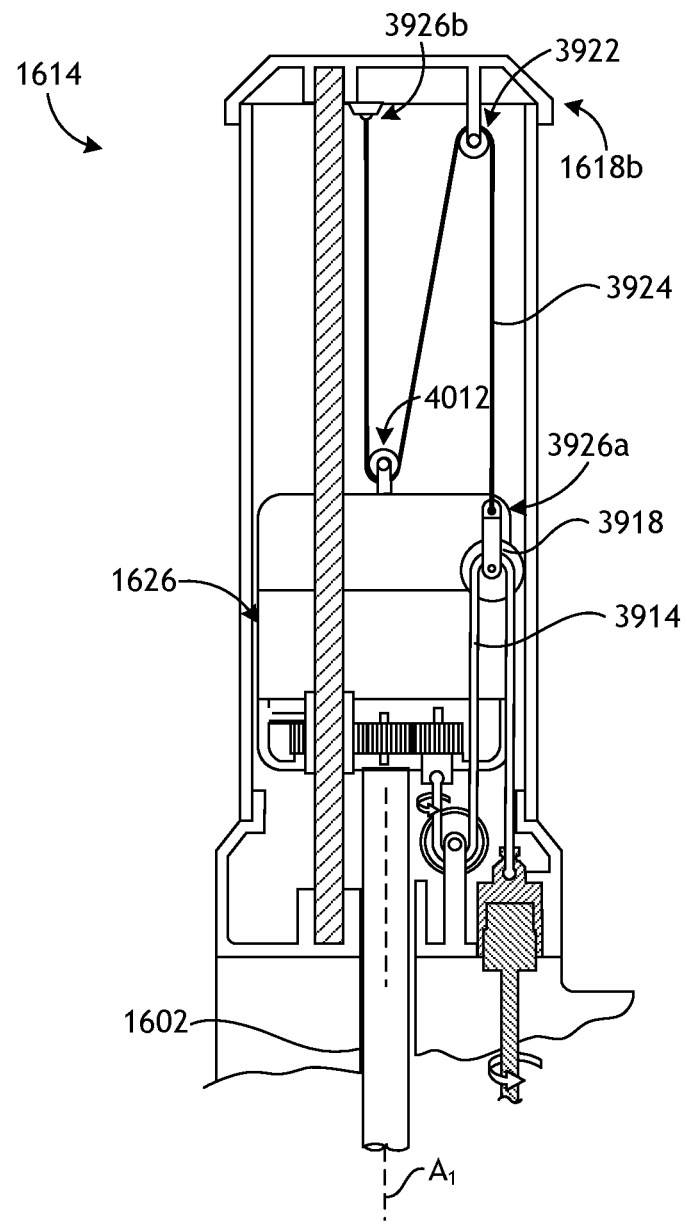
FIG. 40C is an alternative embodiment of the drive housing of FIGS. 40A-40B.

FIG. 40C is an alternative embodiment of the drive housing 1614 of FIGS. 40A-40B, but could alternatively be applicable to the drive housing 1614 of 39A-39B, without departing from the scope of the disclosure. As with the embodiment of FIGS. 40A-40B, the tension pulley 3918 is suspended within the drive housing 1614 at the first end 3926a of the carriage cable 3924 to help maintain constant tension in the torsion cable 3914 during operation. Moreover, the carriage cable 3924 is routed around the carriage pulley 3922. Unlike the embodiment of FIGS. 40A-40B, however, the carriage cable 3924 is further routed around a mounted pulley 4012 coupled or fixed to the carriage 1626 and the second end 3926b of the carriage cable 3924 is fixed to the drive housing 1614, such as at or near the second end 1618b thereof. Including the mounted pulley 4012 results in three routed lengths of the carriage cable 3924, which equals three routed lengths of the torsion cable 3914. This helps to ensure that the same length is paid out as is consumed by axial translation the shaft 1602.

Figure 41B:
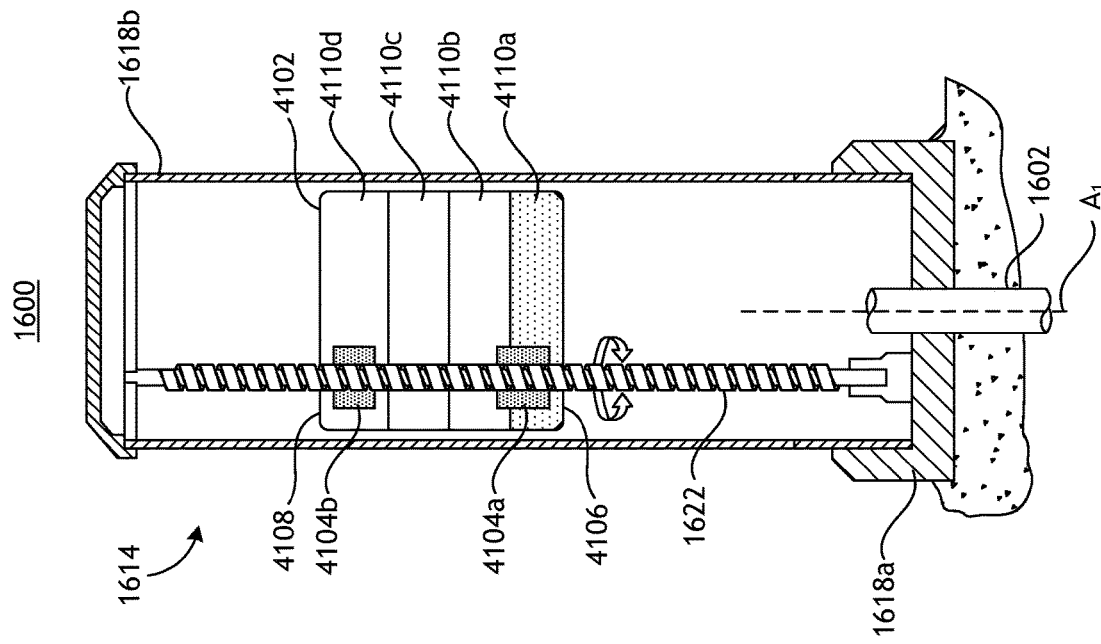
FIGS. 41A-41C are partial cross-sectional side views of alternative embodiments of the drive housing of FIG. 16, according to one or more additional embodiments.
Figure 41A:
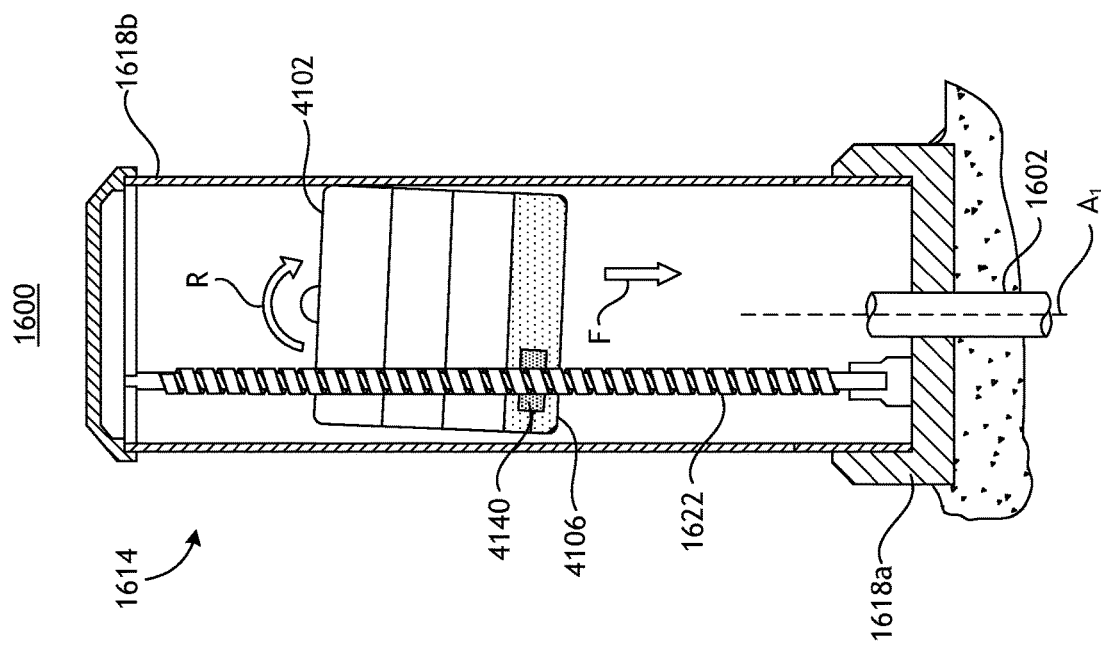
Figure 41C:
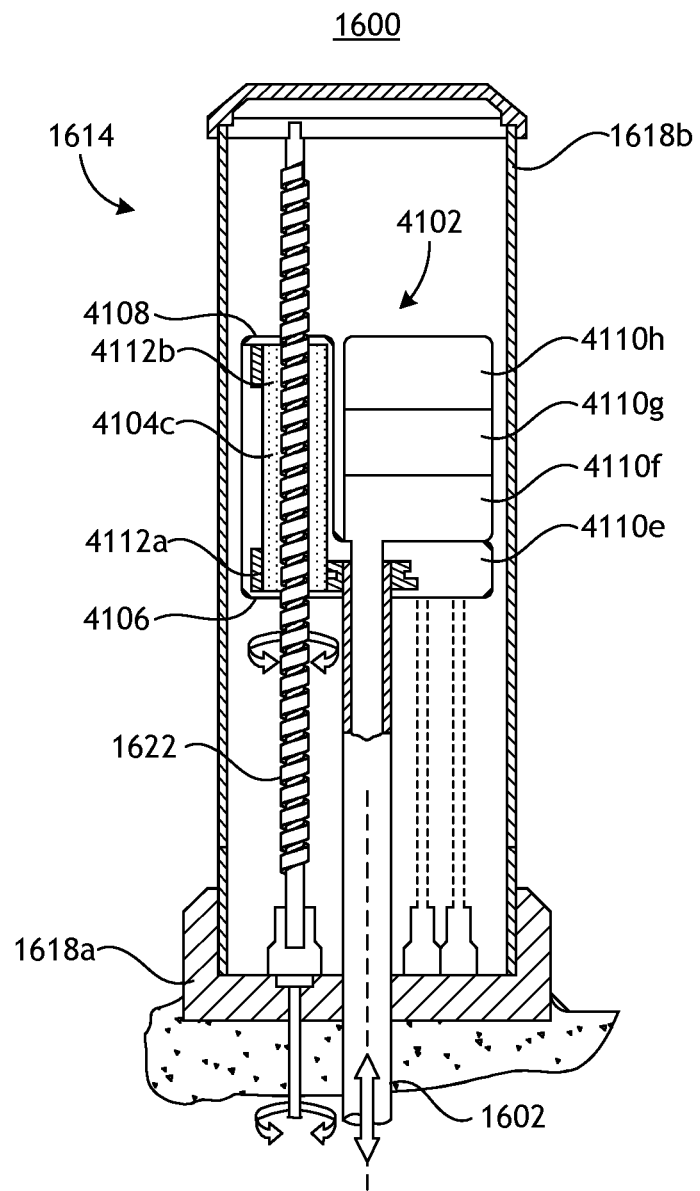

FIGS. 41A-41C are partial cross-sectional side views of alternative embodiments of the drive housing 1614 of FIG. 16, according to one or more additional embodiments. In the illustrated embodiments, the drive housing 1614 includes a carriage 4102 similar in some respects to the carriage 1626 of FIG. 16. For instance, the carriage 4102 is movable the between first and second ends 1618a,b of the drive housing 1614 along the longitudinal axis $A_1$ (i.e., z-axis translation), and the shaft 1602 extends distally from the carriage 4102. Accordingly, as the carriage 4102 moves along the longitudinal axis $A_1$, the carriage 4102 is thereby able to advance or retract an end effector (e.g., the end effector 1604 of FIG. 16) attached to the distal end of the shaft 1602 relative to the drive housing 1614.

In FIG. 41A, the carriage 4102 includes a carriage nut 4104 rotatably mounted to the lead screw 1622. The carriage nut 4104 may be similar in some respects to the carriage nut 1634 of FIG. 16. For instance, the carriage nut 4104 defines corresponding internal helical threading (not shown) matable with the outer helical threading of the lead screw 1622 and, as a result, rotation of the lead screw 1622 causes the carriage nut 4104 to traverse the lead screw 1622 and simultaneously cause the carriage 4102 to advance or retract along the longitudinal axis $A_1$, and correspondingly advance or retract the shaft 1602.

The carriage nut 4104 is located at or near a distal end 4106 of the carriage 4102. During operation of the drive housing 1614, such as activating various functions of the end effector 1604 (FIG. 16), the carriage 4102 may experience various torsional and axial forces F that cause the carriage 4102 to rotate or shift in the direction R. Shifting the carriage 4102 in the direction R can bind or inhibit the movement of the carriage 4102 along the drive housing 1614. According to embodiments of the present disclosure, the carriage 4102 may be stabilized and rotation in the direction R minimized or eliminated by having portions of the carriage nut 4104 located at or near the distal and proximal ends of the carriage 4102. In such embodiments, the carriage 4102 may be mounted to the lead screw 1622 at two or more spaced-apart locations or otherwise spanning a substantial length of the carriage 4102, as described in greater detail below.

In FIG. 41B, the carriage 4102 includes at least two carriage nuts operable to increase the stability of the carriage 4102, i.e., minimize twisting and rotation of the carriage 4102 about the lead screw 1622. More specifically, the carriage 4102 may include a first carriage nut 4104a and a second carriage nut 4104b. The first carriage nut 4104a may be positioned at or near the distal end 4106 of the carriage 4102 and the second carriage nut 4104b is positioned at or near a proximal end 4108 of the carriage 4102. The carriage nuts 4104a,b are each mounted to the rotatable lead screw 1622 and are each supported by the carriage 4102 in a spaced apart relationship, generally located on opposite ends of the carriage 4102.

In embodiments where the carriage 4102 is composed of a plurality of layers, a carriage nut may be present on at least two layers for facilitating translation of the carriage in response to rotation of the lead screw 1622. In FIG. 41B, for example, the carriage 4102 includes four stacked layers, depicted as a first layer 4110a, a second layer 4110b, a third layer 4110c, and a fourth layer 4110d. While four layers are illustrated, it is to be appreciated that the number of layers of the carriage 4102 may be more or less than four, without departing from the scope of the disclosure. The first layer 4110a may be alternately referred to as the "distal layer 4110a," and the fourth layer 4110d may be alternately referred to as the "proximal layer 4110d". In such embodiments, the first carriage nut 4104a may be coupled to the distal layer 4110a and the second carriage nut 4104b may be coupled to the proximal layer 4110d. While not shown, it is contemplated herein to include additional carriage nuts coupled to the other layers, e.g., the second and third layers 4110b,c.

In some embodiments, as illustrated, the first carriage nut 4104a may be coupled to or otherwise encompass or span portions of two or more layers of the carriage 4102. In FIG. 41B, the first carriage nut 4104a is depicted as being coupled to or otherwise supported by the distal layer 4110a, but also extends into the adjacent second layer 4110b. Accordingly, in some embodiments, the first carriage nut 4104a may extend across two layers 4110a, 4110b and the second carriage nut 4104b may be secured to a single layer 4110d.

In FIG. 41C, the carriage 4102 includes a platform layer 4110e that supports a plurality of other layers, shown as layers 4110f, 4110g, and 4110h. In the illustrated embodiment, a portion of the platform layer 4110e extends generally between the distal and proximal ends 4106, 4108 of the carriage 4102, but may alternatively extend only a portion of the distance between the distal and proximal ends 4106, 4108, or may extend further than the distance between the distal and proximal ends 4106, 4108, without departing from the scope of the disclosure.

In the illustrated embodiment, the carriage 4102 includes an elongated carriage nut 4104c that substantially extends from the distal end 4106 to the proximal end 4108 of the carriage 4102. The carriage nut 4104c is mounted to the platform layer 4110e and is thus responsible for the translation of the coupled carriage layers 4110e-h along the lead screw 1622. In some embodiments, the carriage nut 4104 may extend along the entire axial length of the platform layer 4110e, but may alternatively extend along only a portion of the axial length of the platform layer 4110e. Although not illustrated, it is contemplated that a second layer in a stack of two or more layers may incorporate an elongated carriage nut, similar to the elongated nut 4104, having a proximal portion 4112a and a distal portion 4112b and supporting a first layer distally, and a third layer proximally.

4. Implementing Systems and Terminology.

Implementations disclosed herein provide systems, methods and apparatus for instruments for use with robotic systems. It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

As used herein, the terms "generally" and "substantially" are intended to encompass structural or numeral modification which do not significantly affect the purpose of the element or number modified by such term.

To aid the Patent Office and any readers of this application and any resulting patent in interpreting the claims appended herein, applicants do not intend any of the appended claims or claim elements to invoke 35 U.S.C. 112(f) unless the words "means for" or "step for" are explicitly used in the particular claim.

The foregoing previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A robotic surgical tool, comprising:
    a drive housing having a first end and a second end;
    at least one spline extending between the first and second ends and including a drive gear that rotates with rotation of the at least one spline;
    a carriage movably mounted to the at least one spline;
    an elongate shaft having a proximal end coupled to the carriage and extending from the carriage through the first end;
    an end effector arranged at a distal end of the elongate shaft;
    a wrist that interposes the end effector and the distal end of the shaft; and
    an activating mechanism housed in the carriage and operatively coupled to the drive gear such that rotation of the drive gear correspondingly actuates the activating mechanism and thereby causes the wrist to articulate the end effector in at least one plane, wherein the activating mechanism comprises:
        first and second carriers extending at least partially about the shaft, the first carrier being operatively coupled to a first drive member extending to the wrist, and the second carrier being operatively coupled to a second drive member extending to the wrist;
        a first transfer gear extending about the shaft and defining internal threads, the first carrier radially interposing the shaft and the first transfer gear and defining external threads matable with the internal threads of the first transfer gear; and
        a second transfer gear extending about the shaft and defining internal threads, the second carrier radially interposing the shaft and the second transfer gear and defining external threads matable with the internal threads of the second transfer gear,
    wherein actuation of the activating mechanism causes the first carrier and the first drive member to move along the shaft in a first axial direction and further causes the second carrier and the second drive member to move along the shaft in a second axial direction, wherein the first and second axial directions are equal and opposite,
    wherein the first and second transfer gears are matable with the drive gear such that rotation of the drive gear simultaneously rotates the first and second transfer gears, and
    wherein the internal threads of the first and second transfer gears are threaded in opposite directions such that rotating the first and second transfer gears causes the first and second carriers to move in equal but opposite axial directions along the shaft.

2. The robotic surgical tool of claim 1, further comprising:
    a drive input arranged at the first end and operatively coupled to the at least one spline such that rotation of the drive input correspondingly rotates the at least one spline and the drive gear,
    wherein the robotic surgical tool is capable of engaging an instrument driver arranged at an end of a robotic arm and matable with the drive housing at the first end, the instrument driver providing a drive output matable with the drive input such that rotation of the drive output correspondingly rotates the drive input and thereby actuates the activating mechanism.

3. The robotic surgical tool of claim 2, wherein the shaft extends through the instrument driver via a central aperture defined longitudinally through the instrument driver.

4. The robotic surgical tool of claim 1, wherein the carriage comprises at least a first layer and a second layer arranged in series, and wherein the drive gear is arranged between portions of the first and second layers and slidably disposed about the at least one second spline.

5. The robotic surgical tool of claim 1, wherein distal ends of the first and second drive members antagonistically operate at the end effector to articulate the end effector in the at least one plane.

6. The robotic surgical tool of claim 1, wherein a gap is provided between the first and second carriers to allow the first and second carriers to move toward and away from each other during actuation of the activating mechanism.

7. The robotic surgical tool of claim 1, wherein the end effector is selected from the group consisting of a surgical stapler, a tissue grasper, surgical scissors, an advanced energy vessel sealer, a clip applier, a needle driver, a babcock including a pair of opposed grasping jaws, bipolar jaws, a suction irrigator, an endoscope, a laparoscope, and any combination thereof.

8. A method, comprising:
locating a robotic surgical tool adjacent a patient, the robotic surgical tool comprising:
a drive housing having opposing first and second ends and at least one spline extending between the first and second ends and including a drive gear that rotates with rotation of the at least one spline;
a carriage movably mounted to the at least one spline;
an elongate shaft having a proximal end coupled to the carriage and extending from the carriage and penetrating the first end;
an end effector arranged at a distal end of the elongate shaft;
a wrist that interposes the end effector and the distal end of the shaft; and
an activating mechanism housed in the carriage and operatively coupled to the drive gear, the activating mechanism including
a first carrier extending at least partially about the shaft and operatively coupled to a first drive member that extends to the wrist;
a second carrier extending at least partially about the shaft and operatively coupled to a second drive member that extends to the wrist;
a first transfer gear extending about the shaft and defining internal threads, the first carrier radially interposing the shaft and the first transfer gear and defining external threads matable with the internal threads of the first transfer gear; and
a second transfer gear extending about the shaft and defining internal threads, the second carrier radially interposing the shaft and the second transfer gear and defining external threads matable with the internal threads of the second transfer gear;
rotating the at least one spline and the drive gear by actuating a drive input arranged at the first end and operatively coupled to the at least one spline and thereby actuating the activating mechanism as the drive gear rotates;
causing the first carrier and the first drive member to move along the shaft in a first axial direction;
causing the second carrier and the second drive member to move along the shaft in a second axial direction, where the first and second axial directions are equal and opposite;
mating the drive gear with the first and second transfer gears;
rotating the drive gear and thereby simultaneously rotating the first and second transfer gears, wherein the internal threads of the first and second transfer gears are threaded in opposite directions; and
causing the first and second carriers to move in equal but opposite axial directions along the shaft as the first and second transfer gears rotate.

9. The method of claim 8, further comprising:
mating an instrument driver with the drive housing at the first end, the instrument driver being arranged at an end of a robotic arm;
mating a drive output of the instrument driver with the drive input as the instrument driver is mated to the drive housing; and
actuating the drive output to rotate the drive input and thereby actuate the activating mechanism.

10. The method of claim 9, wherein mating the instrument driver with the drive housing at the first end comprises extending the shaft, the end effector, and the wrist through a central aperture defined longitudinally through the instrument driver.

11. The method of claim 8, further comprising antagonistically operating distal ends of the first and second drive members at the end effector and thereby articulating the end effector in at least one plane.

* * * * *